US008158596B2

(12) United States Patent
Liu et al.

(10) Patent No.: US 8,158,596 B2
(45) Date of Patent: Apr. 17, 2012

(54) MATERIALS AND METHODS FOR FOXP3 TUMOR SUPPRESSION

(75) Inventors: Yang Liu, Ann Arbor, MI (US); Pan Zheng, Ann Arbor, MI (US); Xing Chang, Ann Arbor, MI (US); Lizhong Wang, Ann Arbor, MI (US); Runhua Liu, Ann Arbor, MI (US); Yin Wang, Ann Arbor, MI (US); Yan Liu, Ann Arbor, MI (US); Tao Zuo, Columbus, OH (US)

(73) Assignee: The Regents of the University of Michigan, Ann Arbor, MI (US)

( * ) Notice: Subject to any disclaimer, the term of this patent is extended or adjusted under 35 U.S.C. 154(b) by 605 days.

(21) Appl. No.: 12/119,158

(22) Filed: May 12, 2008

(65) Prior Publication Data
US 2009/0325868 A1 Dec. 31, 2009

Related U.S. Application Data

(60) Provisional application No. 60/917,488, filed on May 11, 2007.

(51) Int. Cl.
A61K 48/00 (2006.01)
A01N 63/00 (2006.01)

(52) U.S. Cl. ..................... 514/44 R; 424/93.1
(58) Field of Classification Search .............. 514/44 R; 424/93.1
See application file for complete search history.

(56) References Cited

U.S. PATENT DOCUMENTS 5,449,752 A  9/1995 Fujii et al.
2003/0170648 A1  9/2003 Khattri et al.

FOREIGN PATENT DOCUMENTS

EP  0612728  8/1994
WO  WO-2004/022104  3/2004
WO  WO-2006/138478  12/2006

OTHER PUBLICATIONS

Karanikas et al (J Transl Med, 6: 19: 1-8).*
Voskoglou-Nomikos et al (Clinical Cancer Research, 2003, 9, 4227-4239).*
Kelland et al (European Journal of Cancer, 2004, 40, 827-836).*
Merlo et al (J Clin Oncol, 27(1): 1746-1752, 2009).*
International Preliminary Report of Patentability, PCT/US2008/063419, dated Nov. 17, 2009.
ASHP Handbook on Injectable Drugs, 4th ed., pp. 622-630 (1986).
Banker et al. (Eds.),Pharmaceutics and Pharmacy Practice. J. B. Lippincott Company, Philadelphia, PA. 238-50 (1982).
Bennett et al., The immune dysregulation, polyendocrinopathy, enteropathy, X-linked syndrome (IPEX) is caused by mutations of FOXP3. Nat. Genet. 27: 20-1 (2001).
Brunkow et al., Disruption of a new forkhead/winged-helix protein, scurfin, results in the fatal lymphoproliferative disorder of the scurfy mouse. Nat. Genet. 27: 68-73 (2001).
Eng et al., Early castration reduces prostatic carcinogenesis in transgenic mice. Urology. 54: 1112-9 (1999).
Fontenot et al.. Foxp3 programs the development and function of CD4+CD25+ regulatory T cells. Nat. Immunol. 4: 330-6 (2003).
Garcia de Palazzo et al., Immunohistochemical detection of c-erbB-2 expression by neoplastic human tissue using monospecific and bispecific monoclonal antibodies. Int. J. Biol. Markers. 8: 233-9 (1993).
Kelly et al., The role of c-myc in the proliferation of normal and neoplastic cells. J. Clin. Immunol. 5: 65-77 (1985).
Maguire et al., The neu (c-erbB-2) oncogene. Semin. Oncol. 6: 148-55 (1989).
Nakayama et al., Ubiquitin ligases: cell-cycle control and cancer. Nat. Rev. Cancer. 6: 369-81 (2006).
Piao et al., Frequent loss Xq25 on the inactive X chromosome in primary breast carcinomas is associated with tumor grade and axillary lymph node metastasis. Genes Chromosomes Cancer. 33: 262-9 (2002).
Roncuzzi et al., Loss of heterozygosity at pseudoautosomal regions in human breast cancer and association with negative hormonal phenotype. Cancer Genet. Cytogenet. 135: 173-6 (2002).
Schechter et al., The neu oncogene: an erb-B-related gene encoding a 185,000-Mr tumour antigen. Nature. 312: 513-6 (1984).
Spatz et al., X-chromosome genetics and human cancer. Nat. Rev. Cancer, 4: 617-29 (2004).
Todorovic-Rakovic et al., Comparison between immunohistochemistry and chromogenic in situ hybridization in assessing HER-2 status in breast cancer. Pathol. Int. 55: 318-23 (2005).
Wildin et al., X-linked neonatal diabetes mellitus, enteropathy and endocrinopathy syndrome is the human equivalent of mouse scurfy. Nat. Genet. 27: 18-20 (2001).
Wooster et al., Identification of the breast cancer susceptibility gene BRCA2. Nature. 378: 789-92 (1995).
Xu e al., Evidence for a prostate cancer susceptibility locus on the X chromosome. Nat. Genet. 20: 175-9 (1998).

(Continued)

Primary Examiner — Thaian N Ton
Assistant Examiner — Magdalene Sgagias
(74) Attorney, Agent, or Firm — Marshall, Gerstein & Borun LLP

(57) ABSTRACT

Provided herein are methods of treating a cancer in a subject comprising administering a FOXP3 protein, a nucleic acid encoding a FOXP3 protein, or an inducing compound which induces FOXP3 protein expression. Methods of altering a phenotype of a cancer cell or tumor cell, methods of inhibiting growth of such cells, and methods of inducing apoptosis of these cells are also provided herein. These methods comprise contacting the cell with a FOXP3 protein, a nucleic acid encoding a FOXP3 protein, or an inducing compound which induces FOXP3 protein expression. Further provided herein are diagnostic methods, comprising comparing the expression or structure of a FOXP3 protein or FOXP3 gene in a test sample to that of a normal or prior sample. A method of screening a test compound for anti-cancer activity comprising administering to cells the test compound and measuring FOXP3 protein or FOXP3 gene expression is moreover provided herein.

9 Claims, No Drawings

OTHER PUBLICATIONS

Ziegler, FOXP3: of mice and men. *Annu. Rev. Immunol.* 24: 209-26 (2006).
Zuo et al., FOXP3 is a novel transcriptional repressor for the breast cancer oncogene SKP2. *J. Clin. Invest.* 117: 3765-73 (2007).
Bofin et al., Detection and quantitation of HER-2 gene amplification and protein expression in breast carcinoma. *Am. J. Clin. Pathol.* 122: 110-9 (2004).
Chang et al., The Scurfy mutation of FoxP3 in the thymus stroma leads to defective thymopoiesis. *J. Exp. Med.* 202: 1141-51 (2005).
Chatila et al., JM2, encoding a fork head-related protein, is mutated in X-linked autoimmunity-allergic disregulation syndrome. *J. Clin. Invest.* 106: R75-81 (2000).
Chen et al., Cutting edge: Broad expression of the FoxP3 locus in epithelial cells: a caution against early interpretation of fatal inflammatory diseases following in vivo depletion of FoxP3-expressing cells. *J. Immunol.* 180: 5163-6 (2008).
Dai et al., Evolving gene/transcript definitions significantly alter the interpretation of GeneChip data. *Nucl. Acids Res.* 33: e175 (2005).
de Felipe, Skipping the co-expression problem: the new 2A "CHYSEL" technology. *Genet. Vaccines and Ther.* 2: 13 (2004).
Floess et al., Epigenetic control of the foxp3 locus in regulatory T cells. *PLOS. Biol.* 5: e38 (2007).
Fontenot et al., Regulatory T cell lineage specification by the forkhead transcription factor foxp3. *Immunity.* 22: 329-41 (2005).
Godfrey et al., Fatal lymphoreticular disease in the scurfy (sf) mouse requires T cells that mature in a sf thymic environment: potential model for thymic education. *Proc. Natl. Acad. Sci. USA.* 88: 5528-32 (1991).
Godfrey et al., Transplantation of T cell-mediated, lymphoreticular disease from the scurfy (sf) mouse. *Am. J. Pathol.* 145: 281-6 (1994).
Jimenez et al., Determination of Her-2/Neu status in breast carcinoma: comparative analysis of immunohistochemistry and fluorescent in situ hybridization. *Mod. Pathol.* 13: 37-45 (2000).
Kallioniemi et al., ERBB2 amplification in breast cancer analyzed by fluorescence in situ hybridization. *Proc. Natl. Acad. Sci. USA.* 89: 5321-5 (1992).
Kim et al., CREB/ATF-dependent T cell receptor-induced FoxP3 gene expression: a role for DNA methylation. *J. Exp. Med.* 204: 1543-51 (2007).
Knudson, Mutation and cancer: statistical study of retinoblastoma. *Proc. Natl. Acad. Sci. USA.* 68: 820-3 (1971).
Kristiansen et al., High incidence of skewed X chromosome inactivation in young patients with familial non-BRCA1/BRCA2 breast cancer. *J. Med. Genet.* 42: 877-80 (2005).
Miki et al., A strong candidate for the breast and ovarian cancer susceptibility gene BRCA1. *Science.* 266: 66-71 (1994).
Reimold et al., Chondrodysplasia and neurological abnormalities in ATF-2-deficient mice. *Nature.* 379: 262-5 (1996).
Richardson et al., X chromosomal abnormalities in basal-like human breast cancer. *Cancer Cell.* 9: 121-32 (2006).
Samuels et al., High frequency of mutations of the PIK3CA gene in human cancers. *Science.* 304: 554 (2004).
Slamon et al., Human breast cancer: correlation of relapse and survival with amplification of the HER-2/neu oncogene. *Science.* 235: 177-82 (1987).
Slamon et al., Use of chemotherapy plus a monoclonal antibody against HER2 for metastatic breast cancer that overexpresses HER2. *N. Engl. J. Med.* 344: 783-92 (2001).
Wang et al., Control of inducible chemoresistance: enhanced anti-tumor therapy through increased apoptosis by inhibition of NF-kappaB. *Nat. Med.* 5: 412-17 (1999).
Weinstein, Cancer. Addiction to oncogenes—the Achilles heal of cancer. *Science.* 297: 63-4 (2002).
Wooster, Breast and ovarian cancer. *N. Engl. J. Med.* 348: 2339-47 (2003).
Xing et al., The ets protein PEA3 suppresses HER-2/neu overexpression and inhibits tumorigenesis. *Nat. Med.* 6: 189-95 (2000).
Yaziji et al., HER-2 testing in breast cancer using parallel tissue-based methods. *JAMA.* 291: 1972-7 (2004).
Genbank accession No. EF419427, *Felis catus* FoxP3 mRNA, complete cds, released Feb. 28, 2007.
Genback accession No. ABN79272, FoxP3 [*Felis catus*], released Feb. 28, 2007.
Genbank accession No. DQ387959, *Mus musculus* scurfin (Foxp3) mRNA, complete cds, released Feb. 28, 2007.
Genbank accession No. ABD52722, scurfin [*Mus musculus*], released Feb. 28, 2007.
Genbank accession No. DQ322170, *Bos taurus* forkhead/winged helix transcription factor 3 (Foxp3) mRNA, complete cds, released Jan. 15, 2006.
Genbank accession No. ABC59848, forkhead/winged helix transcription factor 3 [*Bos taurus*], released Jan. 15, 2006.
Genbank accession No. AY841945, *Peromyscus maniculatus* forkhead box P3 (Foxp3) mRNA, partial cds, released Dec. 26, 2004.
Genbank accession No. DQ010327, *Homo sapiens* forkhead box P3 (FOXP3) mRNA, complete cds, alternatively spliced, released May 10, 2005.
Genbank accession No. AAY27088, forkhead box P3 [*Homo sapiens*], released May 10, 2005.
Genbank accession No. NM_001045933, *Bos taurus* forkhead box P3 (FOXP3), mRNA, released May 10, 2005.
Genbank accession No. AY357713, *Mus musculus* strain NOD/LtJ forkhead box P3 (Foxp3) mRNA, complete cds, released Jan. 1, 2004.
Genbank accession No. AAR11306, forkhead box P3 [*Mus musculus*], released Jan. 1, 2004.
Genbank accession No. AY357712, *Mus musculus* strain C57BL/6 forkhead box P3 (Foxp3) mRNA, complete cds, released Jan. 1, 2004.
Genbank accession No. AAR11305, forkhead box P3 [*Mus musculus*], released Jan. 1, 2004.
Genbank accession No. AY376065, *Macaca fascicularis* foxp3 mRNA, complete cds, released Sep. 22, 2003.
Genbank accession No. AAQ82647, foxp3 [*Macaca fascicularis*], released Sep. 22, 2003.
Genbank accession No. AF277994, *Mus musculus* scurfin (Foxp3) gene, complete cds, released Jan. 24, 2001.
Genbank accession No. AAG53608, scurfin [*Mus musculus*], released Jan. 24, 2001.
Genbank accession No. AF277993, *Homo sapiens* scurfin (FOXP3) mRNA, complete cds, released Aug. 8, 2005.
Genbank accession No. AAG53607, scurfin [*Homo sapiens*], released Aug. 8, 2005.
Genbank accession No. AF277992, *Mus musculus* scurfin (Foxp3) mRNA, complete cds; alternatively spliced, released Aug. 18, 2005.
Genbank accession No. AAG53606, scurfin [*Mus musculus*], released Aug. 18, 2005.
Genbank accession No. NM_054039, *Mus musculus* forkhead box P3 (Foxp3), mRNA, released Aug. 18, 2005.
Genbank accession No. NP_473380, forkhead box P3 [*Mus musculus*], released Aug. 18, 2005.
Genbank accession No. AF277991, *Mus musculus* scurfin (Foxp3) mRNA, complete cds; alternatively spliced, released Aug. 18, 2005.
Genbank accession No. AAG53605, scurfin [*Mus musculus*], released Aug. 18, 2005.
Genbank accession No. AAW28860, forkhead box P3 [*Peromyscus maniculatus*], released Dec. 26, 2004.
Nucleotide GSS submission: DQ045675, *Pan troglodytes* FOXP3 gene, Virtual Transcript, partial sequence, genomic survey sequence, released Jun. 2, 2005.
Nucleotide GSS submission: DQ045674, *Homo sapiens* FOXP3 gene, Virtual Transcript, partial sequence, genomic survey sequence, released Jun. 2, 2005.
Genbank accession No. NC_000023, *Homo sapiens* chromosome X, reference assembly, complete sequence, released Aug. 29, 2002.
Genbank accession No. BQ184335.1, *Homo sapiens* cDNA clone, mRNA sequence, released Apr. 30, 2002.
Genbank accession No. DB342786.1, DB342786 THYMU2 *Homo sapiens* cDNA clone THYMU2005410 3-, mRNA sequence, released Oct. 21, 2005.
Genbank accession No. NM_014009, *Homo sapiens* forkhead box P3 (FOXP3), transcript variant 1, mRNA—curated from Genbank accession Nos. AF277993, BQ184335.1, and DB342786.1, Jul. 12, 2011.

Genbank accession No. NP_054728, *Homo sapiens* forkhead box P3 (FOXP3)—protein sequence translation of Genbank accession No. NM_014009, Jul. 12, 2011.

Genbank accession No. NM_001032918, *Macaca mulatta* forkhead box P3 (FOXP3), mRNA, released Sep. 28, 2004.

Genbank accession No. XP_001143169, Predicted: forkhead box P3 [*Pan troglodytes*], released Dec. 6, 2003.

Genbank accession No. XM_001143169, Predicted: *Pan troglodytes* forkhead box P3 (FOXP3), mRNA, released Dec. 6, 2003.

Banham et al., FOXP1 a novel candidate tumor suppressor gene on chromosome 3p. *Cancer Detection Prevent.* (2000).

Bennett et al., The immune dysregulation, polydocrinopathy, enteropathy, X-linked syndrome (IPEX) is caused by mutations of FOXP3. *Nat. Genet.* 27: 20-1 (2001).

Bovenzi et al., Antineoplastic antion of 5-aza-2'deoxycytidine and histone deacetylase inhibitor and their effect on the expression of retinoic acid receptor beta and estrogen receptor alpha genes in breast carcinoma cells. *Cancer Chemother. Pharmacol.* 48: 71-6 (2001).

Gupta et al., Expression of FOXP3 and vascular endothelial growth factor in human breat cancer: Its correlation with angiogenesis and disease progression. *EJC Supplements.* 4: 126 (2006).

Katoh et al., Human FOX gene family (Review). *International J. Oncol.* 25: 1495-1500 (2004).

Mastrangelo et al., A phase I study of emetine hydrochloride (NSC 33669) in solid tumors. *Cancer* May 1973. 31: 1170-5 (1973).

Zuo Tao et al., FOX3 is an X-linked breast cancer suppressor gene and an important repressor of the HER-2/ErbB2 oncogene. *Cell.* 129: 1275-86 (2007).

Zuo Tao et al., FOXP3 is a novel transcriptional repressor for the breast cancer oncogene SKP2. *J. Clin. Invest.* 117: 3765-73 (2007).

International Search Report, European Patent Office, PCT/US2008/063419, dated Feb. 13, 2009.

* cited by examiner

US 8,158,596 B2

MATERIALS AND METHODS FOR FOXP3 TUMOR SUPPRESSION

CROSS REFERENCE TO RELATED APPLICATIONS

This patent application claims the benefit of U.S. Provisional Patent Application No, 60/917,488, filed on May 11, 2007.

GRANT FUNDING

This invention was made with government support under Grant Nos. AI52342, CA58033, and CA120901 awarded by the National Institutes of Health and Grant Nos. W81XWH-06-1-0366 and W81XWH-07-1-0169 awarded by the Army Medical Research and Material Command (Department of Defense). The government has certain rights in the invention.

INTRODUCTION

Identification of BRCA1 and BRCA2 genes marks a key advance in understanding the genetic defects responsible for breast cancer (Miki et al., Science 266: 66-71 (1994); and Wooster et al., Nature 378: 789-792 (1995)). Several other genes, such as TP53, PIK3CA and PTEN, have also been implicated in familial and sporadic cancers (Samuels et al., Science 304: 554 (2004); and Wooster, The New England Journal of Medicine 348: 2339-2347 (2003)). However, the genetic defects for breast cancer have yet to be fully elucidated.

There is an important distinction between autosomal and X-linked genes in that many genes in the latter category are subject to X-inactivation, making it easier to fulfill Knudson's two-hit theory (Knudson, Proc Natl Acad Sci USA 68: 820-823 (1971)). As such, X-linked tumor suppressor genes can potentially be more important because loss of heterozygosity (LOH) or mutation of a single allele can in effect functionally silence the gene (Spatz et al., Nat Rev Cancer 4: 617-629 (2004)). Essentially all tumor suppressor genes are autosomal (Spatz et al., Nat Rev Cancer 4: 617-629 (2004)), although tantalizing evidence concerning abnormalities in the X-chromosome, including LOH, skewed inactivation and selective loss, has been reported in breast cancer samples (Kristiansen et al., J. Med Genet 42: 877-880 (2005); Piao and Malkhosyan, Genes Chromosomes Cancer 33: 262-269 (2002); Richardson et al., Cancer Cell 9: 121-132 (2006); and Roncuzzi et al., Cancer Genet Cytogenet 135: 173-176 (2002)).

HER-2/Neu/ErbB2 is one of the first oncogenes to be identified (Schechter et al., Nature 312: 513-516 (1984)) and has been demonstrated to be expressed in a large proportion of cancer cells (Garcia de Palazzo et al., Int J. Biol Markers 8: 233-239 (1993)) and the level of HER-2/NEU is an important prognostic marker (Slamon et al., Science 235: 177-182 (1987)). Consistent with this finding, anti-HER-2/NEU antibody Herceptin has emerged as an important therapeutic for patients with over-expressed HER-2/NEU on cancer tissues (Slamon et al., N. Engl J Med 344: 783-792 (2001)). Given the clinical and therapeutic significance of Her-2/Neu/ErbB2 over-expression, it is important to identify the molecular mechanisms responsible for its over-expression.

A well-established mechanism responsible for HER-2 over-expression in human cancer is gene amplification (Slamon et al., Science 235: 177-182 (1987)). It is unclear, however, whether gene amplification alone is sufficient to cause HER-2 over-expression because a significant proportion of human cancers with moderate over-expression of HER-2 do not show gene amplification (Bofin et al., Am J Clin Pathol 122: 110-119 (2004); Jimenez et al., Mod Pathol 13: 37-45 (2000); and Todorovic-Rakovic et al., Pathol Int 55: 318-323 (2005)). It is therefore of great interest to identify regulators for HER-2 expression in breast cancer. In this context, Xing et al. (Xing et al., Nat Med 6: 189-195 (2000)) reported that DNA-binding protein PEA3 specifically targets a DNA sequence on the HER-2/neu promoter and down-regulates the promoter activity. It is less clear, however, whether genetic lesions of PEA3 can cause HER-2 over-expression.

Thus there exists a need in the art to identify compounds and methods that modulate over-expression of oncogenes and oncogenic proteins involved in cancer for the development of useful therapeutics and prophylactics.

SUMMARY OF THE INVENTION

The invention provides methods of treating a cancer in a subject. In one embodiment, the method comprises administering to the subject a FOXP3 protein in an amount effective to treat cancer. In another embodiment, the method comprises administering to the subject a nucleic acid comprising a protein coding sequence encoding a FOXP3 protein and a promoter sequence active in a cancer cell of the subject, wherein the promoter is operably linked to the protein coding sequence, in an amount effective to treat cancer. In yet another embodiment, the method comprises administering to the subject an inducing compound that induces expression of a FOXP3 protein in an amount effective to treat cancer.

The invention also provides methods for altering a phenotype of a cancer cell or tumor cell. In one aspect, the method comprises contacting the cell with a FOXP3 protein in an amount effective to alter the phenotype of the cell. In another aspect, the method comprises contacting the cell with a nucleic acid comprising a protein coding sequence encoding a FOXP3 protein and a promoter sequence active in the cell, wherein the promoter sequence is operably linked to the protein coding sequence, in an amount effective to alter the phenotype of the cell. In yet another aspect, the method comprises contacting the cells with an inducing compound that induces expression of a FOXP3 protein in an amount effective to alter the phenotype of the cell.

The invention further provides methods of inhibiting growth of a cancer cell or tumor cell. In one aspect, the method comprises contacting the cell with a FOXP3 protein in an amount effective to inhibit growth of the cell. In another aspect, the method comprises contacting the cell with a nucleic acid comprising a protein coding sequence encoding a FOXP3 protein and a promoter sequence active in the cell, wherein the promoter sequence is operably linked to the protein coding sequence, in an amount effective to inhibit growth of the cell. In yet another aspect, the method comprises contacting the cells with an inducing compound that induces expression of a FOXP3 protein in an amount effective to inhibit growth of the cell.

Further provided by the invention are methods of inducing apoptosis of a cancer cell or tumor cell. In one aspect, the method comprises contacting the cell with a FOXP3 protein in an amount effective to induce apoptosis of the cell. In another aspect, the method comprises contacting the cell with a nucleic acid comprising a protein coding sequence encoding a FOXP3 protein and a promoter sequence active in the cell, wherein the promoter sequence is operably linked to the protein coding sequence, in an amount effective to induce apoptosis of the cell. In yet another aspect, the method comprises contacting the cells with an inducing compound that induces expression of a FOXP3 protein in an amount effective to induce apoptosis of the cell.

A method of diagnosing susceptibility to cancer of a subject is provided herein. The method comprises comparing expression or structure of a FOXP3 protein or a FOXP3 gene in a test tissue sample of the subject to expression or structure of a FOXP3 protein or a FOXP3 gene in a normal tissue sample. Aberrant expression or structure of the FOXP3 protein or a FOXP3 gene in the test tissue sample compared to FOXP3 protein or FOXP3 gene expression or structure in a normal tissue sample indicates susceptibility to cancer of the subject.

Also provided is a method of diagnosing onset of cancer in a subject. The method comprises comparing expression or structure of a FOXP3 protein or a FOXP3 gene in a test tissue sample of the subject to expression or structure of a FOXP3 protein or a FOXP3 gene in a normal tissue sample. Aberrant expression or structure of the FOXP3 protein or a FOXP3 gene in the test tissue sample compared to FOXP3 protein or FOXP3 gene expression or structure in a normal tissue sample indicates the onset of cancer.

A method of monitoring progression of cancer in a subject is provided herein. The method comprises comparing expression or structure of a FOXP3 protein or a FOXP3 gene in a test tissue sample from the subject to expression or structure of the FOXP3 protein or FOXP3 gene in a prior tissue sample from the same subject. Aberrant expression or structure of the FOXP3 protein or FOXP3 gene in the test tissue sample compared to FOXP3 protein or FOXP3 gene expression or structure in the prior tissue sample indicates progression of cancer in the subject.

The invention further provides a method of screening a test compound for anti-cancer activity. The method comprises administering to cells the test compound and measuring expression of a FOXP3 protein or FOXP3 gene in the cells. Increased expression of FOXP3 protein or FOXP3 gene in the cells is indicative of anti-cancer activity of the test compound.

DETAILED DESCRIPTION OF THE INVENTION

The FOXP3 gene was identified during position cloning of Scurfin, a gene responsible for X-linked autoimmune diseases in mice and humans (Immune dysregulation, polyendopathy, enteropathy, X-linked, IPEX) (Bennett et al., *Nat Genet* 27: 20-21 (2001); Brunkow et al., *Nat Genet* 27: 68-73 (2001); Chatila et al., *J. Clin Invest* 106: R75-81 (2000); and Wildin et al., *Nat Genet* 27: 18-20 (2001)). In work described herein, systemic analyses demonstrate that the FOXP3 gene is a mammary and prostate tumor suppressor in mice and humans. Moreover, as shown herein, FOXP3 represses transcription of the HER-2/ErbB2 gene via interaction with forkhead DNA binding motifs in the ErbB2 promoter. FOXP3 is also shown herein to repress transcription of the Skp2 and Myc genes, and to induce the expression of the tumor suppressor gene, p21. Furthermore, as shown herein, expression of FOXP3 caused a decrease in in vitro cancer cell growth, a decrease in in vivo tumor cell growth, a decrease in tumorigenicity, an increase in survival time in tumor-burdened mice, and an induction of apoptosis of cancer cells. Furthermore, an inducer of FOXP3 expression increased the killing of cancer cells, as shown herein.

These findings allow for exploitation of the tumor suppression activity as a marker for diagnosing susceptibility, onset and progression of cancer, methods for treating cancer, and methods for identifying compounds with the same or similar tumor suppression activity that provide therapeutic benefit as well as compounds that induce FOXP3 protein expression in cancer cells.

Treatment

The invention provides methods of treating a cancer in a subject. In one embodiment, the method comprises administering to the subject a FOXP3 protein in an amount effective to treat cancer.

FOXP3 Protein

As used herein "FOXP3 protein" refers to a full length protein or a fragment or a variant of a protein which has FOXP3 biological activity (i.e., biological activity of a FOXP3 protein). The term "biological activity of a FOXP3 protein" as used herein includes transcriptional regulation of one or more genes that includes a promoter sequence that binds FOXP3, the binding of which results in regulated transcription of a protein coding sequence operably linked to the FOXP3 binding site. In one embodiment, the promoter sequence is operably linked to an oncogene. In one specific embodiment, the oncogene is HER-2, which is also known in the art as Neu and ErbB2. In another specific embodiment, the oncogene is Skp2 or Myc. Such oncogenes are known in the art. See, for example, Entrez Gene ID Nos: 2064, 6502, 4609; Maguire and Greene, *Semin Oncol* 16: 148-155 (1989); Zuo et al., *J Clin Invest* 117: 3765-3773 (2007); Nakayama et al., *Nat Rev Cancer* 6: 369-381 (2006); Kelly and Siebenlist, *J Clin Immunol* 5: 65-77 (1985).

The biological activity of a FOXP3 protein can refer to any of the biological activities of a FOXP3 protein as demonstrated herein. In this regard, the biological activity of a FOXP3 protein can be the induction of apoptosis of a cancer cell or tumor cell, the reduction or repression of expression of an oncogene, e.g., ErbB2, Skp2, and Myc, the induction of expression of tumor suppressor genes, e.g., p21, and/or the inhibition or reduction of tumor or cancer cell growth.

In one aspect of the invention, the FOXP3 protein is any of those encoded by any of GenBank Accession Nos: NM_014009; NM_054039; EF419427; DQ387959; NM_001045933; NM_001032918; DQ322170; XM_001143169; AY841945; DQ010327; AY357713; AY357712; AY376065; AF277994; AF277993; AF277992; AF277991; DQ045675; and DQ045674; which are set forth herein as SEQ ID NOs: 1 to 19, respectively, and fragments and variants thereof. Accordingly, the FOXP3 protein can be any of those comprising an amino acid sequence of any of GenBank Accession Nos. NP_054728; NP_473380; ABN79272; ABD52722; NP_001039398; NP_001028090; ABC59848; XP_001143169; AAW28860; AAY27088; AAR11306; AAR11305; AAQ82647; AAG53608; AAG53607; AAG53606; and AAG53605; which are set forth herein as SEQ ID NOs: 20 to 36, and fragments and variants thereof.

The FOXP3 protein can consist essentially of any of the foregoing amino acid sequences described herein, such that other components, e.g., other amino acids, do not materially change the biological activity of the FOXP3 protein. In this regard, the FOXP3 protein can consist essentially of the amino acid sequence of any of SEQ ID NOs: 20 to 36. Alternatively, the FOXP3 protein can consist of any of the specified amino acid sequences described herein, e.g., SEQ ID NOs: 20 to 36.

Variant FOXP3 Protein

In a specific aspect, the FOXP3 protein, which is administered to the subject, is a variant FOXP3 protein. The term "variant" as used herein with respect to a protein, e.g., a FOXP3 protein, includes naturally-occurring proteins that have an amino acid sequence that differs from a previously identified FOXP3 protein and which maintains FOXP3 biological activity, as well as synthetic proteins in which one or more amino acid changes have been introduced into a naturally-occurring protein sequence. Naturally occurring variant proteins can include, for example, an isoform, an alternatively spliced variant, an allelic variant, an ortholog, a paralog, and the like. Synthetic variant proteins include, for example, a genetically engineered mutant.

In one aspect, the variant FOXP3 protein has substantial or significant sequence identity or similarity to a parent FOXP3 protein, which variant FOXP3 protein retains the biological activity of the parent FOXP3 protein. Variants encompass, for example, those variants of a parent FOXP3 protein described herein that retain the ability to specifically bind to a promoter of a gene and regulate the transcription of that gene (e.g., Erb2, Skp2, Myc) to a similar extent, the same extent, or to a higher extent, as the parent FOXP3 protein. In reference to the parent FOXP3 protein, the variant can, for instance, be at least about 30%, 50%, 75%, 80%, 85%, 90%, 93%, 95%, 98% or more identical in amino acid sequence to the parent FOXP3 protein. The biological activity of the variant can be about 30%, 50%, 75%, 80%, 85%, 90%, 91%, 92%, 93%, 94%, 95%, 96%, 97%, 98%, 99%, 100%, 110%, 125%, 150%, 200%, 500%, 1000% or more of the biological activity of the parent FOXP3 protein.

The amino acid sequence of the variant FOXP3 protein can comprise, for example, the amino acid sequence of the parent FOXP3 protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative ammo acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the variant FOXP3 protein can comprise the amino acid sequence of the parent FOXP3 protein with one or more non-conservative amino acid substitutions. In one aspect, the non-conservative amino acid substitution does not interfere with or inhibit the biological activity of the variant FOXP3 protein. In a specific aspect, the non-conservative amino acid substitution enhances the biological activity of the variant FOXP3 protein, such that the biological activity of the variant FOXP3 protein is increased as compared to the parent FOXP3 protein.

FOXP3 Protein Fragments

In one aspect, a fragment of a FOXP3 protein, or a variant thereof, is administered to the subject. The term "fragment" as used herein with reference to a FOXP3 protein means a portion comprising contiguous amino acids of the FOXP3 protein of which it is a part (the parent FOXP3 protein), provided that the portion retains substantial biological activity of the parent FOXP3 protein. FOXP3 protein fragments encompass, for example, those parts of a FOXP3 protein that retain the ability to, e.g., specifically bind to a promoter of a gene (e.g., Erb2, Skp2, Myc) to regulate the transcription of the gene, to a similar extent, the same extent, or to a higher extent, as the parent FOXP3 protein. In reference to the parent FOXP3 protein, the FOXP3 protein fragment can comprise, for instance, about 10%, 25%, 30%, 50%, 68%, 80%, 90%, 91%, 92%, 93%, 94%, 95%, 96%, 97%, 98%, 99%, or more, of the FOXP3 protein. The biological activity of the fragment can be about 30%, 50%, 75%, 80%, 85%, 90%, 93%, 95%, 98%, 100%, 110%, 125%, 150%, 200%, 500%, 1000% or more of the biological activity of the parent FOXP3 protein.

In one instance, the variant FOXP3 protein is a variant having substantial sequence identity to any of the FOXP3 proteins described herein (e.g., SEQ ID NOs: 20-36) with one or more amino acid substitutions at positions that are not conserved among the amino acid sequences of the different FOXP3 orthologs, e.g., the FOXP3 proteins of humans, mice, monkeys, chimpanzees, cows, and cats. In a specific aspect, the variant FOXP3 protein is a variant comprising the amino acid sequence of a human FOXP3 protein (SEQ ID NO: 20) with one or more amino acid modifications at any of the following positions of SEQ ID NO: 20: 7, 10, 15, 17, 22, 23, 27-29, 32, 34, 35, 38-41, 43, 44, 52, 54, 56, 60, 64, 71, 74, 84, 89, 103, 111, 114, 121, 124, 125, 132, 135, 136, 140, 158, 165, 173-176, 182, 184-186, 189, 192, 209, 213, 229, 238, 243, 247, 254, 266, 267, 270, 272, 275, 278, 285-292, 296, 297, 299, 304, 305, 321, 326, 334, 336, 356, 373, 404, 411, 422, 423, 428, 430, and 431.

The FOXP3 protein variant or fragment can comprise additional amino acids at the amino or carboxy terminus, or at both termini, which additional amino acids are not found in the amino acid sequence of the parent FOXP3 protein. In one aspect, the additional amino acids do not encode another protein, but enhance the physico-chemical characteristics of the FOXP3 protein variant or fragment. In a specific aspect, the additional amino acids increase the stability and/or solubility of the FOXP3 protein variant or fragment. In another specific aspect, the additional amino acids aid in the isolation and/or purification of the FOXP3 protein variant or fragment. In one aspect, the additional amino acids do not interfere with the biological function of the FOXP3 protein variant or fragment, e.g., the ability to specifically bind to a promoter of a gene and regulate the transcription of that gene (e.g., Erb2, Skp2, Myc). In another aspect, the additional amino acids enhance the biological activity, as compared to the biological activity of the parent FOXP3 protein.

Accordingly, the FOXP3 proteins (including variants and fragments thereof) can be of any length, i.e., can comprise any number of amino acids, provided that the FOXP3 proteins, (or variants or fragments thereof) retain substantial biological activity. For example, the polypeptide can be about 50 to about 5000 amino acids long, such as 50, 70, 75, 100, 125, 150, 175, 200, 300, 400, 500, 600, 700, 800, 900, 1000 or more amino acids in length. In this regard, the FOXP3 protein can include FOXP3 oligopeptides. Also, the biological activity of the fragment can be about 30%, 50%, 75%, 80%, 85%, 90%, 93%, 95%, 98%, 100%, 110%, 125%, 150%, 200%, or more of the biological activity of the parent FOXP3 protein.

Modified FOXP3 Proteins

In one aspect of the invention, the FOXP3 protein (including variants and fragments thereof) is modified to comprise one or more synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylammomethyl-cysteine, trans-3- and trans-4-hydroxyproline, 4-aminophenylalanine, 4- nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

In one aspect, the FOXP3 proteins (including variants and fragments) are glycosylated, amidated, carboxylated, phosphorylated, esterified, N-acylated, cyclized via, e.g., a disulfide bridge, or other intramolecular bridge, converted into an acid addition salt, dimerized, polymerized, fused, and/or conjugated.

Salts

In one aspect, the FOXP3 protein (including variants and fragments) is in the form of a salt, e.g., a pharmaceutically acceptable salt. Such salts can be prepared in situ during the final isolation and purification of the FOXP3 protein, or separately prepared by reacting a free base function with a suitable acid. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid.

Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate, and undecanoate.

Basic addition salts also can be prepared in situ during the final isolation and purification of the FOXP3 protein, or by reacting a carboxylic acid-containing moiety with a suitable base such as the hydroxide, carbonate, or bicarbonate of a pharmaceutically acceptable metal cation or with ammonia or an organic primary, secondary, or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, and ethylammonium, amongst others. Other representative organic amines useful for the formation of base addition salts include, for example, ethylenediamine, ethanolamine, diethanolamine, piperidine, piperazine, and the like.

Conjugates

In one aspect, the FOXP3 protein is conjugated to a second component via covalent or non-covalent means. The second component can be any component, provided that it does not interfere with the function of the FOXP3 protein or nucleic acid. In a specific aspect, the second component is a bead, a nanoparticle, a microparticle, a detectable label, a polymer, etc. The detectable label can be, for example, a radioisotope, a fluorophore, and an element particle, e.g., gold, silver. Conjugates, as well as methods of synthesizing conjugates in general, are known in the art (See, for instance, Hudecz, F., Methods Mol Biol. 298: 209-223 (2005) and Kirin et al., Inorg Chem. 44(15): 5405-5415 (2005)).

The second component can be directly or indirectly linked or conjugated to the FOXP3 protein. In this regard, the conjugate can comprise a linker which links or bridges the FOXP3 protein to the second component.

In one embodiment, the conjugate comprises a polymer. The polymer can comprise one or more of the following polymers: polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

The polymer can be a biodegradable polymer, including a synthetic biodegradable polymer (e.g., polymers of lactic acid and glycolic acid, polyanhydrides, poly(ortho)esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

The polymer can be a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In a preferred embodiment, the polymer is a water-soluble polymer. Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof.

Fusion and Chimeric Proteins

In one aspect of the invention, the FOXP3 protein (including variants and fragments) is part of a fusion protein or chimeric protein comprising two or more polypeptides fused or joined together, at least one of which is a FOXP3 protein (polypeptide). The other polypeptide of the FOXP3 fusion protein can be a second FOXP3 protein or a polypeptide other than a FOXP3 protein (e.g., a non-FOXP3 polypeptide) which can encode any peptidic or proteinaceous molecule, or a portion thereof, other than a FOXP3 protein (or variant or fragment thereof). The other polypeptide can exist as a polypeptide separate from the FOXP3 protein, or can exist as a polypeptide, which is expressed in frame (in tandem) with the FOXP3 protein. The other polypeptide can be, for example, an immunoglobulin, CD3, CD4, CD8, an MHC molecule, or a portion of any of the foregoing, etc. For purposes herein, examples of an immunoglobulin portion include a heavy chain, a light chain, a variable or constant region of a heavy or light chain, a single chain variable fragment (scFv), or an Fc, Fab, or F(ab)$_2$' fragment of an antibody, etc.

In a specific aspect, the FOXP3 fusion protein or chimeric protein comprises one or more linkers which join the two or more polypeptides together. The linker can be, for instance, a peptide (e.g., a FMDV 2A peptide (see Felipe, *Genetic Vaccines and Therapy* 2: 13-e-publication Sep. 13, 2004)) which joins together two polypeptides.

The fusion protein or chimeric protein can comprise one or more copies of the polypeptide(s) (e.g., FOXP3 protein or non-FOXP3 polypeptide) of the fusion protein. For instance, the fusion protein can comprise 1, 2, 3, 4, 5, or more, copies of a FOXP3 protein and/or of the other polypeptide. Suitable methods of making fusion proteins are known in the art, and include, for example, recombinant methods. See, for instance, Choi et al., *Mol. Biotechnol.*, 31, 193-202 (2005).

Methods of making FOXP3 Proteins

The FOXP3 proteins (including variants and fragments) described herein can be obtained by methods known in the art. Suitable methods of de novo synthesizing polypeptides and proteins are described in, for example, Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752.

Also, the FOXP3 proteins (including variants and fragments) can be recombinantly produced using the nucleic acids described herein using standard recombinant methods. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994.

Further, the FOXP3 proteins (including variants and fragments) can be isolated and/or purified, in part, from a source, such as a plant, a bacterium, an insect, a mammal, e.g., a rat, a human, etc. Methods of isolation and purification are well-known in the art.

Alternatively, the FOXP3 proteins (including variants and fragments) can be commercially synthesized by companies, such as Synpep (Dublin, Calif.), Peptide Technologies Corp. (Gaithersburg, Md.), and Multiple Peptide Systems (San Diego, Calif.). In this respect, the FOXP3 proteins (including variants and fragments) can be synthetic, recombinant, isolated, and/or purified.

Isolated or Purified

As used herein, the term "isolated" means having been removed from its natural environment. The term "purified" as used herein means having been increased in purity, wherein "purity" is a relative term, and not to be necessarily construed as absolute purity. For example, the purity can be at least about 50%, can be greater than 60%, 70%, 75, 80%, 85%, 90%, 91%, 92%, 93%, 94%, 95%, 96%, 97%, 98%, 99%, or can be nearly 100%.

FOXP3 Nucleic Acid

In another embodiment of the method of treating a cancer, the method comprises administering to the subject a nucleic acid comprising a protein coding sequence encoding a FOXP3 protein and a promoter sequence active in a cancer cell of the subject, wherein the promoter is operably linked to the protein coding sequence, in an amount effective to treat cancer.

As used herein "nucleic acid comprising a protein coding sequence encoding a FOXP3 protein" refers to a nucleic acid comprising a nucleotide sequence encoding any of the FOXP3 proteins described herein (including variants, fragments, fusion proteins, and chimeric proteins thereof). By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered inter-nucleotide linkage, such as a phosphoroamidate linkage or a phosphorothioate linkage, instead of the phosphodiester found between the nucleotides of an unmodified oligonucleotide.

In one aspect, the nucleic acid comprising a protein coding sequence encoding a FOXP3 protein comprises a nucleotide sequence encoding a FOXP3 protein comprising the amino acid sequence of any of SEQ ID NOs: 20 to 36. In a specific aspect, the nucleic acid comprises, consists essentially of, or consists of the nucleotide sequence of any of SEQ ID NOs: 1 to 19, or a degenerate thereof. The nucleic acid comprising a protein coding sequence encoding a FOXP3 protein can be a FOXP3 gene or a FOXP3 locus, as described herein. Alternatively, the nucleic acid can be an mRNA or a cDNA encoding a FOXP3 protein.

FOXP3 Gene

In one aspect, the nucleic acid comprising a protein coding sequence encoding a FOXP3 protein is a FOXP3 gene. "FOXP3 gene" as used herein refers to a region of DNA that encodes a FOXP3 protein including coding and non-coding, regulatory sequences, and introns. In a specific aspect, the FOXP3 gene is the FOXP3 gene of GenBank Accession No: NC_000023.9, and fragments, and variants thereof encoding a FOXP3 protein.

FOXP3 Locus

As used herein, the term "FOXP3 locus" means the region of the chromosome of a species comprising a FOXP3 gene. In humans, it is recognized in the art that the FOXP3 locus is located on the p11.23 region of Chromosome X.

Variant Nucleic Acid

In one aspect, the nucleic acid does not comprise any insertions, deletions, inversions, and/or substitutions. However, in another aspect, the nucleic acid comprises one or more insertions, deletions, inversions, and/or substitutions.

For example, the nucleic acid can comprise a nucleotide sequence of SEQ ID NO: 1 which is codon-optimized for enhanced expression. In this regard, the nucleic acid comprising a protein coding sequence encoding a FOXP3 protein can comprise a nucleotide sequence which is substantially identical to any of the nucleic acids referred to herein.

Variant Gene

The term "variant" as used herein with reference to a gene includes naturally-occurring polynucleotides encoding an amino acid sequence that differs from a previously identified FOXP3 protein which maintains FOXP3 activity, as well as synthetic polynucleotides (e.g., nucleic acids) in which one or more nucleotide changes have been introduced into a naturally-occurring polynucleotide sequence. The naturally-occurring variant FOXP3 gene can be an allele, a polymorphic gene, a gene encoding an isoform, an alternatively spliced variant, an ortholog, a paralog, a homolog, and the like. Synthetic variants encompass, for example, a codon-optimized nucleic acid. The variant gene can be, for example, a nucleic acid comprising a nucleotide sequence encoding any of the variant FOXP3 proteins as described herein (e.g., SEQ ID NOs: 20-36). In one aspect, the variant gene encodes a variant FOXP3 protein comprising the amino acid sequence of a human FOXP3 protein (SEQ ID NO: 20) with one or more amino acid modifications at any of the following positions of SEQ ID NO: 20: 7, 10, 15, 17, 22, 23, 27-29, 32, 34, 35, 38-41, 43, 44, 52, 54, 56, 60, 64, 71, 74, 84, 89, 103, 111, 114, 121, 124, 125, 132, 135, 136, 140, 158, 165, 173-176, 182, 184-186, 189, 192, 209, 213, 229, 238, 243, 247, 254, 266, 267, 270, 272, 275, 278, 285-292, 296, 297, 299, 304, 305, 321, 326, 334, 336, 356, 373, 404, 411, 422, 423, 428, 430, and 431.

In one aspect, the nucleic acid comprising a protein coding sequence encoding a FOXP3 protein is recombinant. As used herein, the term "recombinant" refers to (i) a molecule that is constructed outside living cells by joining natural or synthetic nucleic acid segments to nucleic acid molecules that can replicate in a living cell, or (ii) a molecule that results from the replication of those described in (i) above. For purposes herein, the replication can be in vitro replication or in vivo replication.

The nucleic acid comprising a protein coding sequence encoding a FOXP3 protein also comprises a promoter sequence. The promoter sequence, in one aspect, is active in a cell of the subject to which it is administered or active in the cell with which is contacted. By "active" as used herein in context of a promoter sequence is meant that the transcriptional and/or translational molecular machinery (e.g., transcriptional and/or translational regulatory proteins (e.g., transcription factors, enhancer proteins, repressor proteins, and the like)), which are native to the cell, recognizes and binds to the promoter sequence, such that transcription and/or translation of the nucleic acid occurs in the cell.

The promoter sequence of the nucleic acid is operably linked to the protein coding sequence encoding the FOXP3 protein, such that the transcription and/or translation of the protein coding sequence occurs in a manner which is dependent on activity (e.g., transcription factor binding activity) which occurs at or within the promoter sequence.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridme, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N-substituted adenine, 7-methylguanine, 5-methylammomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouratil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

Recombinant Expression Vector

In one aspect of the invention, the nucleic acids are administered to the subject as part of a recombinant expression vector. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole. However, parts of the vectors can be naturally-occurring. The recombinant expression vectors can comprise any type of nucleotides, including, but not limited to DNA and RNA, which can be single- stranded or double-stranded, synthesized or obtained in part from natural sources, and which can contain natural, non-natural or altered nucleotides. The recombinant expression vectors can comprise naturally-occurring or non-naturally-occuring internucleotide linkages, or both types of linkages. In one aspect, the altered nucleotides or non-naturally occurring internucleotide linkages do not hinder the transcription or replication of the vector.

The recombinant expression vector can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGTIO, λGTI 1, λZapII (Stratagene), λEMBL4, and λNMI 149, also can be used. Examples of plant expression vectors include pBIO1, pBI101.2, pBI101.3, pBI121 and pBIN19 (Clontech). Examples of animal expression vectors include pEUK-CI, pMAM and pMAMneo (Clontech). In one aspect, the recombinant expression vector is a viral vector, e.g., a retroviral vector.

The recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

In one embodiment, the recombinant expression vector comprises one or more regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

In one aspect, the recombinant expression vector comprises a native or non-native promoter sequence operably linked to the protein coding sequence encoding a FOXP3 protein (including variants and fragments thereof), which promoter sequence is active in the cell of the subject to which the nucleic acid is administered. The selection of promoters, e.g., strong, weak, inducible, tissue-specific and developmental- specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*. Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Host Cells

In one embodiment of the invention, the nucleic acid is administered to the subject as part of a recombinant expression vector within a host cell, such that the method comprises administering a host cell. As used herein, the term "host cell" refers to any type of cell that can contain the recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant polypeptide, the host cell is preferably a mammalian cell. In one aspect, the host cell is a human cell. The host cell can be of any cell type, can originate from any type of tissue, and can be of any developmental stage.

In one aspect, the host cell can be part of a population of cells. The population of cells can be a heterogeneous population comprising the host cell comprising any of the recombinant expression vectors described, in addition to at least one other cell, e.g., a host cell (e.g., a T cell), which does not comprise any of the recombinant expression vectors. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

For purposes of the methods of treating cancer, wherein host cells or populations of cells are administered to the subject, the cells can be cells that are allogeneic or autologous to the subject. In a specific aspect, the cells are autologous to the subject.

Inducing Compounds

In another aspect of the method of treating cancer in a subject provided herein, the method comprises administering to a subject an inducing compound that induces expression of FOXP3 protein in an amount effective to treat cancer. Inducing compounds that induce expression of FOXP3 include, for example, transcription factors (e.g., which promote the expression of a FOXP3-encoding nucleic acid), upstream regulators of transcription factors that induce FOXP3 expression, inhibiting compounds that inhibit negative regulator(s) of FOXP3 expression, and the like.

In one aspect, the inducing compound is a transcription factor which promotes the expression of a FOXP3 nucleic acid, or a nucleic acid comprising a protein coding sequence encoding the transcription factor. The transcription factor in one instance is a transcription factor which binds to the promoter sequence of a native or naturally-occurring FOXP3 gene. In a specific instance, the transcription factor is c-Jun (e.g., Entrez Gene ID No; 3725) or ATF2 (e.g., Entrez Gene ID No. 1386), or a combination thereof. In another instance, the transcription factor is one which does not bind to the promoter sequence of a native or naturally-occurring FOXP3 gene, but binds to a promoter sequence of an engineered nucleic acid comprising a FOXP3 protein coding sequence. For example, in the instance that the engineered nucleic acid comprises a promoter sequence which comprises bindings sites for a transcription factor other than c-Jun and ATF2 (e.g., NFKB), then the inducing compound in this instance is the other transcription factor (e.g., NFKB).

With regard to the invention, "upstream regulators of regulators of transcription factors that induce FOXP3 expression" includes any compound or molecule that promotes the activation of the transcription factors that induce FOXP3 expression. In one aspect, the upstream regulator is a compound or molecule that causes the activiation the c-Jun and ATF2 transcription factors. In a specific aspect, the upstream regulator is JNK, which activates c-Jun by phosphoylating this transcription factor. In another specific aspect, the upstream regulator is a kinase which phosphorylates ATF2, which promotes the transcriptional activity of ATF2.

The inducing compound in one aspect is an inhibiting compound that inhibits negative regulator(s) of FOXP3 expression. By "compound that inhibits negative regulator of FOXP3 expression" as used herein is meant any compound or molecule that acts against or inhibits a compound or molecule that causes repression of FOXP3 expression.

In various aspects, the inducing compound activates JNK (e.g., JNK1), P38 and/or ATF2. In a specific aspect, the compound is emetine (CAS 483-18-1) and/or anisomycin (CAS 22862-76-6). Emetine is a drug produced from the ipecac root and is used as an anti-protozoal agent and vomiting-inducing agent. It is known to inhibit the nonsense mediated decay pathway and to induce stress response. Anisomycin is a bacterial antibiotic isolated from Streptomyces griseolus, which inhibits protein synthesis, by binding to 60S ribosomal subunits and blocking peptide bond formation, thereby preventing elongation and causing polysome stabilization. Emetine and anisomycin are commercially available products from, e.g., Sigma-Aldrich (St. Louis, Mo.).

In other aspects, the inducing compound is a methyltransferase inhibitor. The methyltransferase inhibitor can be, for example, 5-aza-2'deoxycytidine, zebularine, AMI-1, which are commercially available from, e.g., Calbiochem (Gibbstown, N.J.). In a specific aspect, the methyltransferase inhibitor is 5-aza-2'deoxycytidine.

Routes of Administration

With regard to the methods of treating cancer provided herein, any method useful in delivery of a protein or a nucleic acid known in the art are contemplated. Formulations appropriate for administering a FOXP3 protein or nucleic acid encoding a FOXP3 protein are understood in the art to depend on route of administration, and can include, for example, U.S. Pat. No. 7,208,577, the disclosure of which is incorporated herein by reference in its entirety. Also, any of the routes and formulations further mentioned herein are contemplated.

Also contemplated with regard to the administration of an inducing compound that induces expression of a FOXP3 protein is any method of administration described herein, in any of the variations associated with route of administration, combination therapy, and dosage frequency.

As further discussed herein, dosage frequency is dependent on route of administration and state of the recipient subject and is generally determined by an attending physician,. The therapeutic protein, nucleic acid, or inducing compound, whether administered alone or in combination with one or more other anti-cancer therapeutics, is administered according to the need and condition of the subject and determination of an appropriate dosage regimen is well within the skill of the attending physician.

Pharmaceutical Compositions

In one aspect of the treatment methods described herein, the FOXP3 protein (including variants, fragments, fusion proteins, chimeric proteins, and conjugates thereof), the nucleic acid comprising a protein coding sequence encoding a FOXP3 protein, recombinant expression vector comprising the FOXP3 nucleic acid, the host cell comprising the recombinant expression vector, the population of cells comprising a host cell, or inducing compound (hereinafter collectively referred to as a FOXP3 material) is formulated into a composition, such as a pharmaceutical composition. The pharmaceutical composition comprising the FOXP3 material additionally comprises a pharmaceutically acceptable carrier. The pharmaceutically acceptable carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular FOXP3 material, as well as by the particular method used to administer the FOXP3 material. Accordingly, there are a variety of suitable formulations of the pharmaceutical composition of the invention. The following formulations for oral, aerosol, parenteral, subcutaneous, intravenous, intramuscular, intraarterial, intrathecal, interperitoneal, rectal, and vaginal administration are exemplary and are in no way limiting. More than one route can be used to administer the FOXP3 materials, and in certain instances, a particular route can provide a more immediate and more effective response than another route.

Topical formulations are well-known to those of skill in the art. Such formulations are particularly suitable in the context of the invention for application to the skin. The topical formulation can be a cream, ointment, patch, solution, aerosol spray, paste, film, and the like.

Formulations suitable for oral administration can consist of (a) liquid solutions, such as an effective amount of the FOXP3 material dissolved in diluents, such as water, saline, or juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the FOXP3 material in a flavor, usually sucrose and acacia or tragacanth, as well as pastilles comprising the FOXP3 material in an inert base, such as gelatin and glycerin, or sucrose and acacia, emulsions, gels, and the like containing, in addition to, such excipients as are known in the art.

The FOXP3 material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The FOXP3 material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2- dimethyl-$I_5$3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl -imidazoline quaternary ammonium salts, and (e) mixtures thereof.

The parenteral formulations will typically contain from about 0.5% to about 25% by weight of the FOXP3 material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)). Preferably, when administering cells, the cells are administered via injection, e.g., intravenous injection.

Additionally, the FOXP3 materials, or compositions comprising such FOXP3 materials, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the FOXP3 materials described herein can be formulated as inclusion complexes, such as cyclodextrin inclusion complexes, or liposomes.

Combinations

The pharmaceutical composition can contain any of the FOXP3 materials described herein and can comprise more than one type of FOXP3 material, e.g., a FOXP3 protein and a nucleic acid comprising a protein coding sequence encoding a FOXP3 protein, or two or more different inducing compounds. Alternatively or additionally, the pharmaceutical composition can comprise a FOXP3 material in combination with another pharmaceutically active agent or drug, such as a chemotherapeutic agent (e.g., a chemotherapeutic agent listed in Table 1, asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.), a growth factor, cytokine, hematopoietic factor, lymphokine, and chemokine.

TABLE 1

| Alkylating agents |
| Nitrogen mustards |
| --- |
| mechlorethamine |
| cyclophosphamide |
| ifosfamide |
| melphalan |
| chlorambucil |
| Nitrosoureas |
| carmustine (BCNU) |
| lomustine (CCNU) |
| semustine (methyl-CCNU) |
| Ethylenimine/Methyl-melamine |
| thriethylenemelamine (TEM) |
| triethylene thiophosphoramide (thiotepa) |
| hexamethylmelamine (HMM, altretamine) |
| Alkyl sulfonates |
| busulfan |
| Triazines |
| dacarbazine (DTIC) |
| Antimetabolites |
| Folic Acid analogs |
| methotrexate |
| Trimetrexate |
| Pemetrexed (Multi-targeted antifolate) |
| Pyrimidine analogs |
| 5-fluorouracil |
| fluorodeoxyuridine |
| gemcitabine |
| cytosine arabinoside (AraC, cytarabine) |
| 5-azacytidine |
| 2,2'-difluorodeoxy-cytidine |
| Purine analogs |
| 6-mercaptopurine |
| 6-thioguanine |
| azathioprine |
| 2'-deoxycoformycin (pentostatin) |
| erythrohydroxynonyl-adenine (EHNA) |
| fludarabine phosphate |
| 2-chlorodeoxyadenosine (cladribine, 2-CdA) |

TABLE 1-continued

Type I Topoisomerase Inhibitors camptothecin
topotecan
irinotecan
Biological response modifiers G-CSF
GM-CSF
Differentiation Agents retinoic acid derivatives
Hormones and antagonists
Adrenocorticosteroids/antagonists prednisone and equiv-alents
dexamethasone
ainoglutethimide
Progestins hydroxyprogesterone caproate
medroxyprogesterone acetate
megestrol acetate
Estrogens diethylstilbestrol
ethynyl estradiol/equivalents
Antiestrogen tamoxifen
Androgens testosterone propionate
fluoxymesterone/equivalents
Antiandrogens flutamide
gonadotropin-releasing
hormone analogs
leuprolide
Nonsteroidal antiandrogens flutamide
Natural products
Antimitotic drugs
Taxanes paclitaxel
Vinca alkaloids
vinblastine (VLB)
vincristine
vinorelbine
Taxotere ® (docetaxel)
estramustine
estramustine phosphate
Epipodophylotoxins etoposide
teniposide
Antibiotics actimomycin D
daunomycin (rubido-mycin)
doxorubicin (adria-mycin)
mitoxantroneidarubicin
bleomycin
splicamycin (mithramycin)
mitomycinC
dactinomycin
aphidicolin
Enzymes L-asparaginase
L-arginase
Radiosensitizers metronidazole
misonidazole
desmethylmisonidazole
pimonidazole

TABLE 1-continued etanidazole
nimorazole
RSU 1069
EO9
RB 6145
SR4233
nicotinamide
5-bromodeozyuridine
5-iododeoxyuridine
bromodeoxycytidine
Miscellaneous agents
Platinium coordination complexes cisplatin
Carboplatin
oxaliplatin
Anthracenedione
mitoxantrone
Substituted urea hydroxyurea
Methylhydrazine derivatives N-methylhydrazine (MIH)
procarbazine
Adrenocortical suppressant Mitotane (o,p'-DDD)
ainoglutethimide
Cytokines interferon ($\alpha$, $\beta$, $\gamma$)
interleukin-2
Photosensitizers hematoporphyrin derivatives
Photofrin ®
benzoporphyrin derivatives
Npe6
tin etioporphyrin (SnET2)
pheoboride-a
bacteriochlorophyll-a
naphthalocyanines
phthalocyanines
zinc phthalocyanines
Radiation X-ray
ultraviolet light
gamma radiation
visible light
infrared radiation
microwave radiation The growth factor can include cytokines, lymphokines, growth factors, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, TNF0, TNF1, TNF2, G-CSF, Meg-CSF, GM-CSF, thrombopoietin, stem cell factor, and erythropoietin. Other are compositions can include known angiopoietins, for example Ang-1, -2,-4,-Y, and/or the human Ang-like polypeptide, and/or vascular endothelial growth factor (VEGF). Growth factors include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2, cytokine-induced neutrophil chemotactic factor 2, endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor-1, glial cell line-derived neutrophic factor receptor-2, growth related protein, growth related protein-1, growth related protein-2, growth related protein-3, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor-1, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor-1, platelet derived growth factor receptor-2, pre-B cell growth stimulating factor, stem cell factor, stem cell factor receptor, transforming growth factor-1, transforming growth factor-2, transforming growth factor-1, transforming growth factor-1.2, transforming growth factor-2, transforming growth factor-3, transforming growth factor-5, latent transforming growth factor-1, transforming growth factor-I binding protein I, transforming growth factor-1 binding protein II, transforming growth factor-I binding protein III, tumor necrosis factor receptor type I (TNF-R1), tumor necrosis factor receptor type II (TNF-R2), urokinase-type plasminogen activator receptor, vascular endothelial growth factor, and chimeric proteins and biologically or immunologically active fragments thereof.

When administered in combination, the two or more FOXP3 materials and/or other pharmaceutically active agent can be co-administered. Alternatively, the two or more FOXP3 materials and/or other pharmaceutically active agent can be administered successively.

Dose

For purposes of the invention, the amount or dose of the FOXP3 material administered should be sufficient to effect, e.g., a therapeutic response, in the subject or animal over a reasonable time frame. For example, the dose of the FOXP3 material should be sufficient to inhibit tumor or cancer cell growth, inhibit expression of an oncogene, induce expression of a tumor suppressor gene, induce apoptosis of a cancer cell or tumor cell, or treat cancer in a period of from about 1 to 4 weeks or longer, e.g., 5 to 20 or more weeks, from the time of administration. In certain embodiments, the time period could be even longer. The dose will be determined by the efficacy of the particular FOXP3 material and the condition of the animal (e.g., human), as well as the body weight of the animal (e.g., human) to be treated.

Many assays for determining an administered dose are known in the art. For purposes of the invention, an assay, which comprises comparing the extent to which oncogene expression and/or tumor or cancer cell growth is inhibited in a mammal upon administration of a given dose of a FOXP3 pharmaceutical composition to the mammal among a set of mammals of which is each given a different dose of the pharmaceutical composition, could be used to determine a starting dose to be administered to a mammal. The extent to which oncogene expression, tumor or cancer cell growth, or both is inhibited can be assayed by methods known in the art, including, for instance, the methods described in Zuo et al., *Cell* 129: 1275-1286 (2007); Hammelmann et al., *Am. J. Respiratory & Critical Care Med.* 156: 766-775 (1997); Chen and Schuster, *Mol. Pharmaceutics* 3: 488-495 (2006); and Kim et al., *Am. J. PhysioL Lung Cell Mol. Physiol.* 284: L503-:509 (2004).

The dose of the FOXP3 material also will be determined by the existence, nature and extent of any adverse side effects that might accompany the administration of a particular FOXP3 material. Typically, the attending physician will decide the dosage of the FOXP3 material with which to treat each individual patient, taking into consideration a variety of factors, such as age, body weight, general health, diet, sex, FOXP3 material to be administered, route of administration, and the severity of the condition being treated. By way of example and not intending to limit the invention, the dose of the FOXP3 material can be about 0.0001 to about 1 g/kg body weight of the subject being treated/day, from about 0.0001 to about 0.001 g/kg body weight/day, or about 0.01 mg to about 1 g/kg body weight/day.

Targeted Forms

One of ordinary skill in the art will readily appreciate that the FOXP3 materials described herein can be modified in any number of ways, such that the therapeutic efficacy of the FOXP3 materials is increased through the modification. For instance, the FOXP3 materials can be conjugated either directly or indirectly through a linker to a targeting moiety. The practice of conjugating compounds, e.g., FOXP3 materials, to targeting moieties is known in the art. See, for instance, Wadhwa et al., *J Drug Targeting,* 3, 111-127 (1995) and U.S. Pat. No. 5,087,616. The term "targeting moiety" as used herein, refers to any molecule or agent that aids in localizing an agent to the appropriate sub-cellular location, cell, tissue, organ of a subject. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). The term "linker" as used in context of a targeting moiety, refers to any agent or molecule that bridges the FOXP3 material to the targeting moiety. One of ordinary skill in the art recognizes that sites on the FOXP3 material, which are not necessary for the function of the FOXP3 material, are ideal sites for attaching a linker and/or a targeting moiety, provided that the linker and/or targeting moiety, once attached to the FOXP3 material, do(es) not interfere with the function of the FOXP3 material.

In one instance, the targeted form of the FOXP3 material can comprise a TAT peptide. The use of a TAT peptide as a targeting moiety is known in the art. See, for example, Becker Hapak et al., *Methods* 24(3):247-256 (2001); and Wadia and Dowdy, *Adv Drug Deliv Rev.* 57(4):579-596 (2005).

Depot

Alternatively, the FOXP3 material can be modified into a depot form, such that the manner in which the FOXP3 material is released into the body to which it is administered is controlled with respect to time and location within the body (see, for example, U.S. Pat. No. 4,450,150). Depot forms of FOXP3 materials can be, for example, an implantable composition comprising the FOXP3 material and a porous or non-porous material, such as a polymer, wherein the FOXP3 material is encapsulated by or diffused throughout the material and/or degradation of the non-porous material. The depot is then implanted into the desired location within the body and the FOXP3 material are released from the implant at a predetermined rate.

Subjects

The subject referred to herein can be any subject. In one embodiment, the subject is a mammal. As used herein, the term "mammal" refers to any mammal, including, but not limited to, mammals of the order Rodentia, such as mice and hamsters, and mammals of the order Logomorpha, such as rabbits. In a specific aspect, the mammals are from the order Carnivora, including Felines (cats) and Canines (dogs). In another specific aspect, the mammals are from the order Artiodactyla, including Bovines (cows) and Swines (pigs) or of the order Perssodactyla, including Equines (horses). In yet another specific aspect, the mammals are of the order Primates, Ceboids, or Simoids (monkeys) or of the order Anthropoids (humans and apes). In one aspect, the mammal is a human.

Types of Cancer

Methods described herein are applicable to any or all forms of cancer in which FOXP3 tumor suppression activity regulates neoplastic transformation. The cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In various aspects, the cancer is breast cancer, lymphoma, liver cancer, sarcoma, adenocarcinoma, prostate cancer, thymic epithelial cancer, lung cancer, and/or pancreatic cancer.

The term "treat" as well as words stemming therefrom, as used herein, does not necessarily imply 100% or complete treatment. Rather, there are varying degrees of treatment of which one of ordinary skill in the art recognizes as having a potential benefit or therapeutic effect. In this respect, the methods of treating cancer can provide any amount or any level of treatment of cancer in a mammal. Furthermore, the treatment provided by the method can include treatment of one or more conditions or symptoms of the disease being treated. For instance, the treatment can include one or more of reduction of tumor growth, reduction in metastasis, increase in survival, increase in apoptosis of cancer or tumor cells, increase in the killing of cancer or tumor cells.

The invention also provides a method for altering the phenotype of a cancer cell or tumor cell. In one aspect, the method comprises contacting the cell with a FOXP3 protein in an amount effective to alter the phenotype of the cell.

In another aspect, the method comprises contacting the cell with a nucleic acid comprising a protein coding sequence encoding a FOXP3 protein and a promoter sequence active in the cell, wherein the promoter sequence is operably linked to the protein coding sequence, in an amount effective to alter the phenotype of the cell.

In yet another aspect, the method comprises contacting the cell with an inducing compound that induces the expression of a FOXP3 protein in an amount effective to alter the phenotype of the cell.

Phenotypes

Gene Expression

The phenotype that is altered by the method can be any phenotype (e.g., any observable and/or measurable character of a cell) which is effected or caused by the expression of a FOXP3 protein. In one aspect, the phenotype is the expression level of a gene or gene product thereof. In a specific aspect, the gene is an oncogene, such as, for example, ErbB2, Skp2, or Myc, and the expression level of the oncogene is reduced upon contacting the cell with the FOXP3 protein, nucleic acid, or inducing compound. In another specific aspect, the gene is a tumor suppressor gene, e.g., p21, and the expression level of the tumor suppressor gene is increased upon contacting the cell with the FOXP3 protein, nucleic acid, or inducing compound.

Methods of determining expression levels in a cell are well-known in the art. Suitable methods include, for example, Western blotting, radioimmunoassay, ELISAs, immunofluorescence microscopy, quantitative phosphorimaging, in the case of determining the expression level of a protein; Southern blotting, Northern blotting, and quantitative RT-PCR, in the case of determining the expression level of a nucleic acid. Such methods are taught in Sambrook et al., *Molecular Cloning: A Laboratory Manual,* 3$^{rd}$ ed., Cold Spring Harbor Laboratory Press, 2001; and Zuo et al., *Cell* 129: 1275-1286 (2007).

Growth Inhibition

In another aspect, the phenotype is growth rate of the cell (e.g., cancer cell or tumor cell) and the growth rate is reduced upon contacting the cell with the FOXP3 protein, nucleic acid, or inducing compound. In this regard, the invention provides a method of inhibiting growth of a cancer cell or tumor cell. In one aspect, the method comprises contacting the cell with a FOXP3 protein in an amount effective to inhibit growth of the cell.

In another aspect, the method comprises contacting the cell with a nucleic acid comprising a protein coding sequence encoding a FOXP3 protein and a promoter sequence active in the cell, wherein the promoter sequence is operably linked to the protein coding sequence, in an amount effective to inhibit growth of the cell.

In yet another aspect, the method comprises contacting the cell with an inducing compound that induces the expression of a FOXP3 protein in an amount effective to growth of the cell.

Methods of determining growth inhibition are known in the art and include, for example, thymidine kinase assays, [3-(4, 5-dimethylthiazol-2-yl)-2,5-diphenyltetrazolium bromide] (MTT) assays, gel microdrop (GMD) assays, calorimetric cell growth assays, and the like. Such methods are described in, for example, Zhu and Lin, *Acta Pharmacol Sin* 26: 1130-1137 (2005); Akselband et al., *J Microbiol Methods* 62: 181-197 (2005). Alternatively, a kit for measuring cell growth, e.g., a colorimetric growth assay, is commercially available from Sigma-Aldrich (St. Louis, Mo.).

Inducing Apoptosis

In one aspect, the phenotype of the cell is altered to an apoptotic phenotype upon contacting the cell with the FOXP3 protein, nucleic acid, or inducing compound. By "apoptostic phenotype" as used herein, is meant any observable and/or measurable character of a cell undergoing apoptosis (programmed cell death). The apoptotic phenotype can be, for example, a translocation of Cytochrome C from the mitochondria to the cytosol of a cell, a change in glutathione levels in a cell, a disruption of mitochondria transmembrane potential, a change in the nitrate/nitrite concentrations, and the level of BCL2 proteins.

In this regard, the invention provides a method of inducing apoptosis of a cancer cell or tumor cell. In one aspect, the method comprises contacting the cell with a FOXP3 protein in an amount effective to induce apoptosis of the cell.

In another aspect, the method comprises contacting the cell with a nucleic acid comprising a protein coding sequence encoding a FOXP3 protein and a promoter sequence active in the cell, wherein the promoter sequence is operably linked to the protein coding sequence, in an amount effective to induce apoptosis of the cell.

In yet another aspect, the method comprises contacting the cell with an inducing compound that induces the expression of a FOXP3 protein in an amount effective to induce apoptosis of the cell.

Methods of determining whether a cell has become apoptotic are known in the art. Suitable methods include, radioactive and non-radioactive assays that measure increases in plama membrane permeability, colorimetric assays that measure the reduction in the metabolic activity of mitochondria, DNA fragmentation assays, Cytochrome C and AIF release assays, annexin V detection assays, and the like. See, for example, Wang et al., *Eur J Pharmacol*, e-publication on Apr.8, 2008; Bu et al., *BMC Cancer* 7: 208 (2007).

With regard to the methods of altering a phenotype, inhibiting growth, and inducing apoptosis described herein, the FOXP3 protein, nucleic acid comprising a protein coding sequence encoding a FOXP3 protein, and inducing compound can be any of those described herein. In carrying out the method, the cancer cell or tumor cell is contacted with the protein, nucleic acid, or inducing compound using any method that permits uptake by the cell including, but not limited to, any of the methods described herein, e.g., a method using purified and isolated protein or nucleic acid, or use of a protein or nucleic acid with an appropriate carrier. Carriers include pharmaceutical solutions, delivery vehicles such as particles, lipids, one or more fusion protein moieties, antibodies including multispecific antibodies and other carriers effective for specific deliver to a target cell.

Also, with regard to the methods described herein, the cancer cell or tumor cell can be any of those described herein. In one aspect, the cell over-expresses a HER-2/ErbB2 gene. In another aspect, the cell over-expresses a Skp2 gene. Further, the cell can be an in vitro cell or an in vivo cell. In this regard, the cell can be a cell in a subject, e.g., a human.

Diagnosis

Susceptibility to Cancer

The invention further provides methods relating to cancer diagnosis. In one aspect, methods of diagnosing susceptibility to cancer of a subject, comprising comparing the expression or structure of a FOXP3 protein or FOXP3 gene in a test tissue sample to that of a normal tissue sample, are provided herein. Aberrant expression or structure of the FOXP3 protein or FOXP3 gene in the test tissue sample compared to that of the normal tissue sample indicates susceptibility to cancer of the subject.

Onset of Cancer

In another aspect, methods of diagnosing onset of cancer in a subject, comprising comparing expression or structure of a FOXP3 protein or FOXP3 gene in a test tissue sample to expression or structure of FOXP3 protein in a normal tissue sample, are provided. Aberrant expression or structure of a FOXP3 protein or FOXP3 gene in a test tissue sample compared to the expression or structure of a FOXP3 protein or FOXP3 gene in a normal tissue sample indicates onset of cancer in the subject.

Monitoring Progression

In yet another aspect, methods of monitoring the progression of cancer in a subject, comprising comparing the expression or structure of a FOXP3 protein or FOXP3 gene in a test tissue sample to expression or structure of FOXP3 protein in a prior tissue sample, are provided. Aberrant expression or structure of a FOXP3 protein or FOXP3 gene in the test tissue sample compared to the expression or structure of a FOXP3 protein or FOXP3 gene in a prior tissue sample indicates progression of cancer in the subject.

As used herein "aberrant structure" of a FOXP3 protein or a FOXP3 gene refers to a measurable or observable change in the structure of the protein or gene, which is associated with cancer, e.g., with susceptibility, onset, or progression of cancer. In one instance, the aberrant structure of a FOXP3 protein or a FOXP3 gene is a protein mutation or gene mutation that gives rise to a change in FOXP3 biological activity compared to biological activity of a FOXP3 protein of a FOXP3 gene that does not have an identified mutation. In one instance, the aberrant structure of the FOXP3 protein comprises an amino acid modification. The amino acid modification can be a substitution, insertion, or deletion of an amino acid of the wild-type, native FOXP3 amino acid sequence. The amino acid modification can occur in any part of the amino acid sequence of FOXP3. For example, the amino acid modification can occur in any of the exons of the FOXP3 protein (e.g., Exon 1, Exon 2, Exon 3, Exon 4, Exon 5, Exon 6, Exon 7, Exon 8, Exon 9, Exon 10, Exon 11, Exon 12) or functional domains of the FOXP3 protein (e.g., repressor domain, zinc finger domain, leucine zipper domain, forkhead domain). In one instance, the amino acid modification occurs or is located in a zinc finger domain of the FOXP3 protein, a forkhead domain of the FOXP3 protein, a repressor domain of the FOXP3 protein, or in a combination of two or more of the foregoing. The amino acid modification in a specific instance is an amino acid substitution of a human FOXP3 protein (SEQ ID NO: 20) selected from the group consisting of: A38S, G42R, G87D, V97A, V117M, P177S, N196I, P202L, G203R, C204R, E205K, K227R, V239I, S296T, P338L, A353T, F373S, F395L, and G403R.

The aberrant structure of a FOXP3 gene of the test tissue sample can be an insertion, deletion, or substitution of a nucleotide of the wild-type, native FOXP3 gene. In one instance, the aberrant structure of the FOXP3 gene comprises a mutation in reference to a human FOXP3 mRNA (SEQ ID NO: 1) selected from the group consisting of: G300T, G312A, T424C, G448A, T556A, G557A,C717T, C793T, A775T, G785A, C798T, G801A, G822A, A868G, G917A, G920A, G993A, T1074A, C1201T, G1245A, T1306C, T1373A, and G1395A.

In one instance, the aberrant structure of a FOXP3 protein or FOXP3 gene of the test tissue sample comprises a deletion of an entire copy of the gene or a part thereof, e.g., an exon, intron, promoter sequence, untranslated region, of the gene. In a specific instance, the aberrant struction comprises a deletion of any of Exons 3, 4, 6, 7, and 8, or any combination thereof. In another instance, the aberrant structure of the test tissue sample comprises a deletion of one or more copies of the entire FOXP3 gene. In yet another specific instance, the aberrant structure of the FOXP3 gene comprises a mutation in an intron of a FOXP3 gene, e.g., the one of GenBank Accession No. NC000023.9, such as G→A at 31 basepairs downstream from Exon 6; C→T at 51 basepairs upstream of Exon 3; G→A at 30 basepairs downstream of Exon 11, C→G at 44 basepairs downstream of Exon 11; G→A at 63 basepairs downstream of Exon 11; A→G at 50 basepairs upstream of Exon 3; and G→A at 3 basepairs downstream of Exon 6.

Furthermore, in one instance, the aberrant structure of a FOXP3 gene comprises an increase in CpG methylation of the sequence which is 5' to the promoter of the FOXP3 gene, e.g., the gene of GenBank Accession No. NC000023.9.

As used herein "aberrant expression" of a FOXP3 protein or a FOXP3 gene refers to a measurable or observable change in the amount or concentration of the gene, or gene product thereof, which is associated with cancer, e.g., with susceptibility, onset, or progression of cancer. In one instance, aberrant expression means a level of transcription, translation, and/or post-translational modification that results in a change in FOXP3 biological activity compared to the level of activity observed in cells that are not cancer cells or cells that are not susceptible to becoming cancer cells. In a specific instance, the aberrant expression of the FOXP3 protein or FOXP3 gene is at least 2-fold less than that of the normal tissue sample or prior tissue sample. In another specific instance, the aberrant expression is a 5-fold, 10-fold, 20-fold or more reduction in expression as compared to that of the normal or prior tissue sample.

Ways to Assess Structure and Expression

Methods of assessing the structure of a protein or gene are well-known in the art and include, for example, any of the methods described herein and any sequencing or PCR-based methods described in Sambrook et al., supra. Likewise, methods of assessing the expression level of a gene are well-known in the art and include any of the methods described herein.

Tissue Samples

As used herein, "test tissue sample" refers to the sample being analyzed, assessed, compared, evaluated in the diagnostic methods described herein. As used herein, "normal tissue sample" refers to the reference sample and is a tissue sample which is known to not be diseased, e.g., cancerous or tumorous. In certain methods, the test tissue sample and the normal tissue sample can be from the same subject. In other methods, the test tissue sample and the normal tissue sample are from different subjects.

As used herein, "prior tissue sample" refers to a tissue sample that optionally is from the same tissue of the test tissue sample, but is obtained at an earlier time point than the time point at which the test tissue sample was obtained from the subject.

The test tissue sample, normal tissue sample, and prior tissue sample can comprise any type of tissue from any organ of the subject. The tissue can be tissue of a lung, heart, liver, brain, pancreas, kidney, skin (epithelium), endothelium, uterus, ovary, prostate, breast, stomach, small intestine, large intestine, lymph node, spleen, thymus, thyroid, etc.

Screening

The invention provides screening methods. In one instance, the screening method is a method for screening a test compound for anti-cancer activity. The method comprises administering to cells the test compound and measuring expression of FOXP3 protein or FOXP3 gene in the cells. Increased expression of a FOXP3 protein or FOXP3 gene in the cells is indicative of anti-cancer activity of the test compound.

The test compound can be any molecule, synthetic or naturally-occuring. In one aspect, the test compound is a peptide, protein, or a small molecule. The cells of the screening method can be any type of cells, such as any of those described herein with reference to host cells.

Additionally, methods are provided for identifying compounds that possess FOXP3 activity, wherein compounds having FOXP3 activity are identified as candidate compounds that are useful for treating or preventing cancer. In one embodiment, methods of identifying a compound having FOXP3 activity are provided comprising the step of comparing expression of a protein encoded by a protein coding region operably linked to a HER-2/ErbB2 promoter sequence that binds FOXP3 and regulates HER-2/ErbB2 protein expression in the presence of a test compound to expression of the protein encoded by the protein coding region operably linked to the HER-2/ErbB2 promoter sequence in the presence of FOXP3, where protein expression in the presence of the test compound equal to protein expression in the presence of FOXP3 indicates of the test compound has FOXP3 activity. In one aspect, the FOXP3 activity is transcriptional regulation. In another aspect, methods are provided to identify a compound having FOXP3 binding activity comprising the step of comparing binding of a test compound with a HER-2/ErbB2 promoter sequence that binds FOXP3 to binding of FOXP3 with the HER-2/ErbB2 promoter sequence, wherein comparable binding of the test compound to the promoter sequence and FOXP3 binding to the promoter sequence indicates comparable binding activity. In still another aspect, method to identify a compound having FOXP3 binding activity are provided comprising the step of measuring binding of a test compound to a HER-2/ErbB2 promoter sequence that binds FOXP3 in the presence of FOXP3, wherein binding of the test compound to the promoter sequence indicates displacement of FOXP3 binding to the promoter sequence and indicates binding strength of the test compound compared to FOXP3 binding strength. Compounds amenable to being assessed in methods to identify those with FOXP3 activity include, but are not limited to, small molecules, proteins, peptides, and the like. Test compounds include those that are commercially available or synthesized, as well as those which are individual, purified compounds or those present in libraries comprising a multiplicity of different compounds.

EXAMPLES

Example 1

Spontaneous and Carcinogen-Induced Mammary Cancer in FOXP3sf/+Female Mice

Mutant BALB/c mice used for the initial study carried mutations in two closely linked X-chromosome genes, FOXP3$^{sf}$ and Otc$^{spf}$. During the course of the study, a spontaneous segregation of Otc$^{spf}$ produced a BALB/c Otc$^{spf/+}$ strain. Meanwhile, an independent line of Scurfy mice was obtained, a line that had never been crossed to the Spf mutant mice and which was backcrossed with the Scurfy mutant allele (FOXP3$^{sf}$) for more than 12 generations into the BALB/c background (Chang et al., J. Exp Med 202: 1141-1151 (2005)). Female mice with only one copy of the FOXP3 gene survived to adulthood and appeared normal within the first year of life (Godfrey et al., Proc Natl Acad Sci U.S.A. 88: 5528-5532 (1991)) with normal T cell function (Fontenot et al., Nat Immunol 4 330-336 (2003); Fontenot et al., Immunity 22 329-341 (2005); Godfrey et al., AM J Pathol 145: 281-286 (1994)). Extended observations of the retired breeders for up to two years revealed that close to 90% of the FOXP3$^{sf/+}$ Otc$^{spf/+}$ and FOXP3$^{sf/+}$ mice spontaneously developed malignant tumors.

Cancer incidences in the littermate controls and a line of congenic mice with a mutation in Otc, but not FOXP3, were comparable with each other. About 60% of the tumors were mammary carcinomas, although other tumors, such as lymphoma, hepatoma, and sarcoma were observed. Histological analyses revealed lung metastasis, based on expression of ER and/or PR, in about 40% of the mice with mammary cancer. More than a third of the tumor-bearing mice had multiple lesions in the mammary glands. Most, although not all, mammary carcinomas expressed the estrogen receptor (ER+, 14/18) and progesterone receptor (PR+, 12/18).

In order to focus on mammary cancer, the mice were treated with a carcinogen, 7,12-dimethylbenz [a] anthracene (DMBA), in conjunction with progesterone. Mice heterozygous for FOXP3$^{sf}$, but not those heterozygous for Otc$^{spf}$, showed substantially increased susceptibility to mammary cancer, as revealed by earlier onset, increased incidence and multiplicity of the breast tumors. These data demonstrated that a mutation of FOXP3, but not Otc, results in a major increase in susceptibility to mammary carcinoma.

Since two independently maintained lines sharing the FOXP3 mutation have a comparably higher incidence of mammary cancer, the FOXP3 mutation is likely responsible for the increased rate of breast cancer.

Example 2

FOXP3 Expression in Normal and Cancerous Mammary Tissues

Since expression of FOXP3 has not been reported in mammary tissue, normal and cancerous cells were isolated by laser-capture microdissection and expression of FOXP3 and Otc was compared by real-time RT-PCR and histochemistry.

Quantitative real-time PCR was carried out as follows. Relative quantities of mRNA expression were analyzed using real-time PCR (Applied Biosystems ABI Prism 7700 Sequence Detection System, Applied Biosystems). The SYBR (Qiagen) green fluorescence dye was used in this study. The primer sequences (5'-3') are listed in Table 2 below.

TABLE 2

| PCR Primers | | Primer sequence 5' to 3' | SEQ ID NO: |
|---|---|---|---|
| mouse FOXP3 realtime-PCR | Forword | ATCTCCTGGATGAGAAAGGCAAGG | 37 |
| | Reverse | TGTTGTGGAAGAACTCTGGGAAGG | 38 |
| mouse Hprt realtime-PCR | Forword | AGCCTAAGATGAGCGCAAGT | 39 |
| | Reverse | TTACTAGGCAGATGGCCACA | 40 |
| mouse ErbB2 realtime-PCR | Forword | AAACCTGGAACTCACCTACCTGC | 41 |
| | Reverse | GGTATTGTTCAGCGGGTCTCCATT | 42 |
| mouse Ck19 realtime-PCR | Forword | ACCCTCCCGAGATTACAACC | 43 |
| | Reverse | CAAGGCGTGTTCTGTCTCAA | 44 |
| mouse Cd3 realtime-PCR | Forward | TCTGCTGGATCCCAAACTCT | 45 |
| | Reverse | TGCACTCCTGCTGAATTTTG | 46 |
| human HER2/Neu realtime-PCR | Forword | ACCGGCACAGACATGAAGCT | 47 |
| | Reverse | AGGAAGGACAGGCTGGCATT | 48 |
| human FOXP3 realtime-PCR | Forword | TACTTCAAGTTCCACAACATGCGACC | 49 |
| | Reverse | CGCACAAAGCACTTGTGCAGACTCAG | 50 |
| human p16 realtime-PCR | Forword | CAACGCACCGAATAGTTACG | 51 |
| | Reverse | ACCAGCGTGTCCAGGAAG | 52 |
| human FOXP3 cDNA cloning BamHI | Forword | CCCGGATCCGCCACCATGCCCAACCCCAGGCCT | 53 |
| del stop codon XbaI | Reverse | CTCTCTAGAGGGGCCAGGTGTAGGGTTGGAACAC | 54 |
| mouse FOXP3 cDNA cloning EcoRI | Forword | AAGAATTCGCCACCATGCCCAACCCTAGGCCA | 55 |
| del stop codon XbaI | Reverse | AAGAATTCGCCACCATGCCCAACCCTAGGCCA | 56 |
| ErbB2 promoter cloning -1.8 Kb SacI | Forword | GGGGAGCTCTTTGTCACATGTATGTGTTGAAC | 57 |
| ErbB2 promoter cloning -1.2 Kb SacI | Forword | GGGGAGCTCGAGGGAAGATACGAACTCAGGTC | 58 |
| ErbB2 promoter cloning -0.8 Kb SacI | Forword | GGGGAGCTCTGAGAACTGGGTAAAGTCAGA | 59 |
| BlgII | Reverse | GGGAGATCTCAATCTCAGCTCCACAACTTCAC | 60 |
| ChIP-PCR ErbB2 -3.2 Kb | Forward | ACAGGCCACTGGTTTCAGAC | 61 |
| | Reverse | TGAGGGAACTTCGAAGACAGA | 62 |

TABLE 2-continued

| PCR Primers | | Primer sequence 5' to 3' | SEQ ID NO: |
|---|---|---|---|
| ChIP-PCR ErbB2 -2.2 Kb | Forward | GGAGAAGGGACACCTTTGATCT | 63 |
| | Reverse | GGGAATATCTGAGCCCTAGCAA | 64 |
| ChIP-PCR ErbB2 -1.6 Kb | Forward | AGCCCTCTTGTTCTACTTCTGG | 65 |
| | Reverse | GACACTCTAGAAGCACTCAGCA | 66 |
| ChIP-PCR ErbB2 -1.0 Kb | Forward | CGGGCAATTCATCCTGGTAAAC | 67 |
| | Reverse | GATATCACTCCTGAAGCCTGGT | 68 |
| ChIP-PCR ErbB2 -0.4 Kb | Forward | GAGAGTCTTGGAAGTCACCAGT | 69 |
| | Reverse | GCAGTTCTCACCCACTTCCTAA | 70 |
| ChIP-PCR ErbB2 +0.5 Kb | Forward | GGGAACTCCTTGGGAAAGTTCT | 71 |
| | Reverse | ACTGGAAGAGCTCTGAGAAAGC | 72 |
| ChIP-PCR ErbB2 +1.1 Kb | Forward | CGTGTTAGGCAAGCCCTCTA | 73 |
| | Reverse | GGAATCCCAAAGCACACAGT | 74 |
| ChIP-PCR ErbB2 +1.8 Kb | Forward | TGTTGCCAAACAGCAGTCTC | 75 |
| | Reverse | TCCATCCTGAAGAAGGCAAG | 76 |
| ChIP-PCR ErbB2 +2.8 Kb | Forward | TTGTGCTCTCTCTCTGCACTGT | 77 |
| | Reverse | AGTCCGTTCCTGTTTGACAACT | 78 |
| ChIP-PCR ErbB2 Exon 3 | Forward | ACATCCAGGAAGTCCAGGGATAC | 79 |
| | Reverse | GCGGTGGTGACGTTGTCCAAA | 80 |
| ChIP-PCR GAPDH | Forward | CCACCATCCGGGTTCCTATAAA | 81 |
| | Reverse | TTGCACACTTCGCACCAGCAT | 82 |
| human FOXP3 sequence Exon1 PCR | Forward | GCACACACTCATCGAAAAAAA | 83 |
| | Reverse | AATGGGGCCCACATCTGGTA | 84 |
| human FOXP3 sequence Exon2 PCR | Forword | TATTGTCTACGCAGCCTGCCC | 85 |
| | Reverse | ATGGTGGCATGGGGTTCAA | 86 |
| human FOXP3 sequence Exon3 PCR | Forward | TGAGGATCAGGATGGCCTCT | 87 |
| | Reverse | GCACATGTGGGCTGTGGTT | 88 |
| human FOXP3 sequence Exon4 PCR | Forward | AACCACAGCCCACATGTGC | 89 |
| | Reverse | TGACCCCAGAGTACTGCAAT | 90 |
| human FOXP3 sequence Exon5 PCR | Forward | TTTTCGAGGCTCAGGAGGGT | 91 |
| | Reverse | TGTCCACTGACCTGTCCTTCC | 92 |
| human FOXP3 sequence Exon6 PCR | Forward | CAGGAAGGACAGGTCAGTGGA | 93 |
| | Reverse | TGGGCCACTCACTTGAGGAA | 94 |
| human FOXP3 sequence Exon7 PCR | Forward | TGTCGTGGTCACCTGCAT | 95 |
| | Reverse | CATTACCTGCTGCTCCAGAGA | 96 |
| human FOXP3 sequence Exon8 PCR | Forword | TAGCCTGGGCAAAGATGTG | 97 |
| | Reverse | AGTCTGAGTCTGCCACCACCA | 98 |
| human FOXP3 sequence Exon9 PCR | Forword | TTTAAGCCTCTGGGTCACCA | 99 |
| | Reverse | TGGGAATGTGCTGTTTCCAT | 100 |

TABLE 2-continued

| PCR Primers | | Primer sequence 5' to 3' | SEQ ID NO: |
|---|---|---|---|
| human FOXP3 sequence Exon10 PCR | Forword | TGCATGGGGCTTGATTCAT | 101 |
| | Reverse | AACCCACTCTGAGGGCACT | 102 |
| human FOXP3 sequence Exon11 PCR | Forword | TTTGGGGAATGTGCCCCTTA | 103 |
| | Reverse | AATGTGCCTATGAGCCCAGA | 104 |
| human FOXP3 sequence Exon12 PCR | Forword | ATAGGCACATTGGGGAGGAA | 105 |
| | Reverse | TGTTCGTCCATCCTCCTTTC | 106 |

The complete absence of the cd3 transcripts indicated that the micro-dissected samples were devoid of T cells, the main cell types known to express FOXP3 (Fontenot et al., *Immunity* 22 329-341 (2005)). FOXP3 mRNA was detected in normal mammary epithelium from both the WT and FOXP3$^{sf/+}$ Otc$^{spf/+}$ mice, but not in mammary cancer cells from the same FOXP3$^{sf/+}$ Otc$^{spf/+}$ mice. Immunohistochemical staining confirmed the loss of expression of FOXP3 in the mammary carcinoma generated from the FOXP3$^{sf/+}$ Otc$^{spf/+}$ mice.

In view of the fact that FOXP3 is an X-linked gene that is subject to X-chromosomal inactivation (Fontenot et al., *Immunity* 22 329-341 (2005)), anchored RT-PCR was carried out to clone the low levels of FOXP3 mRNA in the breast tissues. The cDNA clones from pooled samples were sequenced after ruling out potential T cell contamination (based on a lack of T-cell specific cd3 transcripts). It was observed that 100% of the FOXP3 transcripts in the cancerous tissues were from the mutant alleles, which indicates that the wild-type allele was silenced in the tumor cells. In contrast, the transcripts from the mutant allele constituted 15% of the transcripts in the normal mammary samples from the same mice. Thus, the expression pattern of FOXP3 fulfills another criterion for a tumor suppressor gene.

Thus, unlike essentially all cancer suppressor genes identified to date, FOXP3 is X-linked and inactive in cells in which the WT allele was silenced by X-inactivation. This is indeed the case as the low levels of FOXP3 transcripts in the cancer cells were derived exclusively from the mutant alleles.

Example 3

FOXP3 is a Repressor of Erbb2 Transcription

Characterization of the mammary tumors in the mutant mice revealed wide-spread up-regulation of ErbB2, in contrast to those rare tumors from WT mice. Using real-time RT-PCR, 8-12-fold more ErbB2 mRNA was found in the cancer cells than in normal epithelium. There was also more ErbB2 mRNA in the FOXP3$^{sf/+spf/+}$ epithelium than in that of the WT female mice, which indicates a potential gene dosage effect of FOXP3 on the regulation of ErbB2 expression in vivo. Transfection of the TSA cell line with FOXP3 cDNA repressed ErbB2 levels on the TSA cell line.

Analysis of the 5' sequence of the ErbB2 gene revealed multiple binding motifs for the forkhead domain. To test whether FOXP3 interacts with the ErbB2 promoter, anti-V5 antibody was used to precipitate sonicated chromatin from the TSA cells transfected with the FOXP3-V5 cDNA and real-time PCR was used to quantitate the amounts of the specific ErbB2 promoter region precipitated by the anti-V5 antibodies in comparison to those that bound to mouse IgG control.

Chromatin immunoprecipitation (ChIP) was carried out according to published procedure (Im et al., *Methods Mol Biol* 284: 129-146 (2004)). Briefly, the FOXP3-V5-transfected TSA cells were sonicated and fixed with 1% paraformaldehyde. The anti-V5 antibodies or control mouse IgG were used to pull down chromatin associated with FOXP3-V5. The amounts of the specific DNA fragment were quantitated by real-time PCR and normalized against the genomic DNA preparation from the same cells.

Results showed that the anti-V5 antibodies precipitated significantly higher amounts of ErbB2 promoter DNA than the IgG control, with the highest signal around 1.6 kb 5' of the transcription starting site.

To test whether the binding correlated with the suppression by FOXP3, luciferase reporter was produced using the 1.8, 1.2 and 0.8 Kb upstream of the ErbB2 TSS and the ability of FOXP3 to repress ErbB2 promoter activity was tested. In three separate cell lines, it was observed that the region with the strongest ChIP signal was required for optimal repression by FOXP3. Furthermore, two potential FOXP3-binding sites, identified based on (i) intensity of ChIP signal, (ii) abundance of consensus binding sites and (iii) conservation between mouse and human, were deleted using site-directed mutagenesis and the effect on FOXP3-mediated repression was measured.

Deletion of either binding site substantially increased the ErbB2 promoter activity in the presence of FOXP3 and thus alleviated FOXP3-mediated repression.

Since the region deleted in mut B is 100% conserved between mouse and man and since this deletion completely wiped out repression, an electrophoretic mobility shift assay (EMSA) was carried out as follows to determine whether the forkhead DNA-binding motifs in region B bound FOXP3. Nuclear extracts were prepared as described previously (Wang et al., *Nat Med* 5: 412-417 (1999)). The sequence for the WT probe (W) was AGTTCAATTTGAATTTCA-GATAAACG (SEQ ID NO: 107). Mutant probe (M) (AGT-TCAGCGCGAGCGCCAGAGCGCCG; SEQ ID NO: 108) with mutations of all three potential forkhead binding sites was used as specificity control.

Results showed that the nuclear extracts from the FOXP3-expressing cells specifically retarded migration of the WT but not mutant $^{32}$P-labeled probes compared with control cells. While mutant cold probes did not affect FOXP3 binding activities, WT cold probes significantly diminished them, establishing that the binding of these complexes is specific to forkhead DNA-binding motifs. Site-directed mutagenesis was therefore carried out to replace the 12 nucleotides (mut C) within the ErbB2 promoter and promoter activity and FOXP3-repression was compared by luciferase assays. While the wild-type promoter was repressed by FOXP3, no repression by FOXP3 was observed when the mutant promoter was used. Moreover, in contrast to the deletion Mut B, the mutations had no impact on the basal activity of the ErbB2 promoter. Taken together, these data make a compelling case that FOXP3 represses the ErbB2 promoter via specific forkhead binding motifs.

Example 4

FOXP3 Defects in Human Breast Cancer

The levels and isoforms of the FOXP3 transcripts were analyzed in a panel of normal human mammary epithelial cells (HMEC), an immortalized but non-malignant cell line (MCF-10A), and 10 malignant breast cancer cell lines differing in ER/PR and HER-2 status. Early passage of HMEC with no methylation in the CpG island of the P16 promoter was used to avoid effects associated with P16 inactivation in post-senescence HMEC cultures (Romanov et al., 2001).

Results showed that similar levels of FOXP3 transcripts were observed in two independent isolates of HMEC and in the immortalized cell line MCF-10A. Each of the 10 tumor cell lines had a different degree of reduction in FOXP3 mRNA in comparison to HMEC and MCF-10A. Among them, two were completely devoid of FOXP3 mRNA, while the others had a 1.5-20 fold reduction. In view of this result, PCR was carried out using anchored primers spanning exons 1-12 to amplify the FOXP3 transcripts, and the PCR products were sequenced.

None of the tumor cell lines expressed full-length FOXP3 transcripts. HMEC expressed the same two isoforms as observed in the T cells, while MCF-1OA expressed an isoform lacking exon 3. The same isoform was also found in four tumor cell lines at much lower levels. In addition, three tumor cell lines expressed an isoform lacking both exons 3 and 4. The alternative splicing resulted in a frame-shift beginning at codon 70 and an early termination at codon 172. Furthermore, two tumor cell lines expressed a FOXP3 isoform lacking exons 3 and/or 8. Exon 8 encodes the leucine-zipper domain that is frequently mutated in IPEX patients (Ziegler, *Annu Rev Immunol* 24: 209-226 (2006)). Thus, FOXP3 is abnormal in breast cancer cell lines.

Consistent with a role for FOXP3 in repressing HER-2 expression, the majority of the breast cancer cell lines had higher levels of HER-2 in comparison to normal HMEC. However, additional changes are also likely required for HER-2 over-expression, as three cell lines did not over-express HER-2 even though the FOXP3 transcripts were greatly reduced.

Three approaches were taken to determine whether the findings in the mutant mice and human breast cancer cell lines are relevant to the pathogenesis of human breast cancer.

First, immunohistochemistry was used to determine expression of FOXP3 in normal and cancerous tissue. HER-2 expression was performed using Pathway™ HER-2 (Clone CB11) (Ventana Medical Systems, Inc., Tucson, Ariz.) on the BenchMark® XT automated system per the manufacturer's recommended protocol. The HER-2 levels were scored by commonly used criteria (Yaziji et al., *JAMA* 291: 1972-1977 (2004)).

Results showed that while more than 80% of the normal breast samples expressed FOXP3 in the nuclei of the epithelial cells, less than 20% of the cancerous tissue showed nuclear staining.

Second, fluorescence in situ hybridization (FISH) was used to determine whether the FOXP3 gene was deleted in the breast cancer samples. FISH for FOXP3 deletion was done using BAC clone RP11-344014 (ntLocus X: 48,817,975-48,968,223), which was verified by PCR to contain the FOXP3 gene. The minimal common region of deletion was done using flanking p-telomeric and centromeric clones, RP11-573N21 (ntLocus X: 43,910,391-44,078,600) and RP11-353K22 (ntLocus X: 54,416,890-54,545,788), respectively. Locus specific BAC clones were labeled with spectrum orange using commercially available reagents per the manufacturer's recommendations (Vysis, Downers Grove, Ill.). Chromosome X enumeration was done by FISH using a commercially available spectrum green CEPX probe (Vysis, Downers Grove, Ill.). Cutoff values for the determination of deletion of each probe were established by scoring 200 nuclei from forty 0.6 millimeter cores representing normal tissue from 10 different organs. Cutoff values were then established by calculation of the mean plus three times the standard deviation of the number of normal cells with a false-positive signal. For BAC clones RP11-344014, RP11-573N21, and RP11-353K22 these numbers were 7.1%, 8.1%, and 8.0%, respectively, meaning only cases of breast cancer with greater than this percentage of cells with one or two CEPX signals and none or a single locus specific signal, respectively, were counted as abnormal. For all FISH done in this study a total of at least 200 nuclei were scored for every case. For virtually all cases with FOXP3 deletion, the percentage of cells with a reduced number of FOXP3 greatly exceeded the cut-off value. These were thus considered clear-cut cases of gene deletion.

All FISH were done using standard protocols optimized for breast cancer specimens. Briefly, formalin fixed, paraffin-embedded tissue microarray blocks were cut into 3 to 4 µm thick sections, incubated over night at 56° C., deparaffinized, washed, digested with protease, formalin fixed, denatured, and hybridized at 37° C. for 16 hours. The slides were then washed in a post-hybridization wash, counter stained with 4'-6-diamidino-2-phenylindole (DAPI), and covered with a coverslip. Specimens were evaluated with an Olympus BX51 microscope (Olympus Optical Company, LTD., Japan) under oil immersion at ×150 magnification using the recommended filters.

The minimal common region of deletion was identified using flanking p-telomeric and centromeric clones. Out of 223 informative samples, 28 cases were observed (12.6%) with deletions in any of the three loci. Interestingly, deletion of the FOXP3 locus was found in all of the 28 cases. These data suggested that FOXP3 is likely within the minimal region of deletion in the Xp11 region studied. Although all deletions were heterozygous, the FOXP3 protein was undetectable in 26/28 cases. Thus, it appears that for the majority of the breast cancer samples, LOH alone was sufficient to inactivate the locus, perhaps due to X-chromosomal inactivation. The two cases with both deletion and FOXP3 expression had X-polysomy with 3 and 4 X-chromosomes respectively.

Thirdly, DNA was isolated from matched normal and cancerous tissues (50 cases with formalin fixed samples and 15 cases of frozen samples) from patients with invasive ductal carcinoma and amplified all 11 coding exons and intron-exon boundary regions by PCR. Two independent PCR products were sequenced in order to confirm the mutations. Unless the bulk sequencing data were unambiguous, the PCR products were cloned and 5-10 independent clones from each reaction were sequenced. Among the formalin fixed samples, only cases were used in which the normal tissue samples gave unambiguous sequencing data that matched the wild-type FOXP3 sequence.

When the cancerous tissues were compared with normal tissues from the same patient, 36% (18/50 formalin-fixed samples and 5/15 frozen samples) showed somatic mutations. Loss of the wild-type allele was found in 6/23 cases (38%) of cancer samples with somatic FOXP3 mutations, while the other cases had heterozygous mutations. Eighteen mutations resulted in the replacement of amino acids all or most of which are likely to be critical for FOXP3 function, as judged from the pattern of mutation in IPEX patients (Ziegler, *Annu Rev Immunol* 24: 209-226 (2006)) or in the conserved zinc finger domain that has so far not been implicated.

Although most samples had a single mutation of the FOXP3 gene, two cases were observed with multiple mutations. In the first sample, the two mutations occurred in consecutive codons, resulting in two nonconservative replacements of amino acid residues. Clonal analysis revealed that both mutations occurred in the same clone. In the second sample, three mutations occurred in intron 11. Since this mutant lacked a WT allele, it is likely that all of the mutations occurred in the same allele. The possibility of a mismatch in the cancer and normal samples was ruled out by comparing the normal and cancer samples for polymorphism of two unrelated genes.

To directly test whether FOXP3 mutations affect the repressor activity for the HER-2 gene, two representative somatic FOXP3 mutants isolated in the cancer cells were chosen and their repressor activity for the HER-2 promoter was tested. One mutation (338P→L) was found in the signature forkhead domain which is often mutated in the IPEX patient, while the other double mutation (204C→R, 205E→K) was from the zinc finger domain that has not been implicated in IPEX patients. Both mutations significantly reduced the repressor activity of FOXP3. The reduced repression of the HER-2 promoter correlates with a significantly reduced inhibition of HER-2 mRNA.

In four instances, mutations were identified in introns that may potentially affect RNA splicing. Thus, laser-guided micro-dissection was used to isolate normal and cancerous epithelial cells from one case with a mutation in intron 6. RNA was isolated and tested for the potential effects of the mutation on RNA splicing (using primers on exons 5 and 8) and total FOXP3 transcript, as quantitated by real time PCR using primers spanning exons 10-12. Tissues from another patient with a mutation in exon 7 were used as control.

Results showed that primers spanning exons 5 and 8 failed to detect FOXP3 mRNA from the cancerous tissue of case No. 23. Furthermore, primers spanning exons 10-12 also failed to detect any FOXP3 transcripts. Substantial levels were detected in the normal epithelial cells of the same patients as well as in normal and cancerous tissues from case No. 22. Since the wild-type allele had been lost in the cancer cells of case No. 23, it is likely that the mutation in intron 6 inactivated FOXP3. With an intron of 944 nucleotides, a mutation that prevented splicing of intron 6 would cause premature-termination codon-mediated RNA decay, which is operative in the FOXP3 gene (Chatila et al., *J. Clin Invest* 106: R75-81 (2000)).

Example 5

FOXP3 Defects and HER-2 Over-Expression

To demonstrate a role for FOXP3 defect in HER-2 over-expression, the FOXP3 gene was first silenced in early passage of primary HMEC (Supplemental FIG. S3) using a lentiviral vector expressing FOXP3 siRNA. In brief, lentivirus-based siRNA expressing vectors were created by introducing the murine U6 RNA polymerase III promoter and a murine phosphoglycerate kinase promoter (pGK)-driven EGFP expression cassette into a vector of pLenti6/V5-D-TOPO back bone without CMV promoter. A hairpin siRNA sequence of FOXP3 (target sequence at the region of 1256 to 1274 nucleotides; 5'-GCAGCGGACACTCAATGAG-3') (SEQ ID NO: 109) was cloned into the lentiviral siRNA expressing vectors by restriction sites of ApaI and EcoRI.

Results showed that FOXP3 siRNA reduced FOXP3 expression by more than 100-fold while increasing HER-2 mRNA by 7-fold. A corresponding increase in cell surface HER-2 was also observed. These results implicate FOXP3 as a repressor of HER-2 in human breast epithelial cells.

Since a major mechanism for HER-2 up-regulation in breast cancer is gene amplification (Kallioniemi et al., *Proc Natl Acad Sci U.S.A.* 89: 5321-5325 (1992)), an intriguing issue was whether FOXP3 is capable of repressing HER-2 in cancer cells with an amplified HER-2 gene. A Tet-off line of BT474, a breast cancer cell line known to have HER-2 gene amplification (Kallioniemi et al., *Proc Natl Acad Sci U.S.A.* 89: 5321-5325 (1992)) was produced and transiently transfected it with a pBI-EGFP-FOXP3− vector. After drug selection, the cells were cultured either in the presence or absence of doxycycline.

While the cells cultured with doxycycline did not express FOXP3, removal of doxycycline resulted in induction of FOXP3 in a significant fraction of the cancer cells, which allowed comparison of HER-2 levels in the FOXP3$^+$ and FOXP3$^-$ cells in the same culture by flow cytometry. Results showed that FOXP3$^-$ cells had about a 5-10-fold higher level of the HER-2 protein on the cell surface in comparison to the FOXP3$^+$ cells.

The expression of FOXP3 was then compared with HER-2 expression in breast cancer tissues. Down-regulation of FOXP3 was strongly associated with the over-expression of HER-2, which supports a role for FOXP3 inactivation in HER-2 over-expression in breast cancer. Nevertheless, since many of the FOXP3-cells remained HER-2-, it is likely that dis-regulation of FOXP3 is insufficient for HER-2 up-regulation. On the other hand, since only 3/82 FOXP3$^+$ cancer cells expressed high levels of HER-2, FOXP3 inactivation is likely important for HER-2 up-regulation under most circumstances.

Next, breast cancer samples were divided based on their HER-2 gene copy numbers and compared the FOXP3$^+$ and FOXP3$^-$ cancer samples for the relative amounts of cell surface HER-2 expression. Results showed that in each of the gene dose categories, FOXP3$^+$ samples had reduced HER-2 scores in comparison to the FOXP3$^-$ samples. These results strongly suggest a critical role for FOXP3 in repressing HER-2 expression even in the cases of HER-2 gene amplification.

Of the 223 informative samples among the 238 that were screened for Xp11.2 deletions, those with deletions encompassing the FOXP3 locus had significantly higher HER-2 scores compared to those without deletions (P=0.03). Likewise, the relative HER-2 scores were compared among the 50 samples in which we had sequenced all FOXP3 exons. Results showed that the mutations in the FOXP3 gene correlated with higher levels of HER-2 (P=0.0083).

Example 6

FOXP3/FOXP3 Inhibits Tumorigenicity of Cancer Cells

To test whether the FOXP3 gene can suppress the growth of breast cancer cells, the empty vector or the vectors carrying either FOXP3 (mouse or human origin) or Otc cDNA were transfected into three breast cancer cell lines, including mouse mammary tumor cell line TSA or human breast cancer cell lines MCF7 (ER$^+$HER-2$^{low}$, no HER-2 amplification) and SKBr3 (ER-HER-2$^{high}$ with HER-2 amplification). The untransfected cells were removed by a selection with G418.

While the vector-transfected cells grew rapidly, the FOXP3-transfected cell lines seldom grew into large colonies. The FOXP3-transfected culture had a drastic reduction in both the size and the number of the drug-resistant colonies. No effect was observed when the Otc cDNA was used.

To test whether the somatic mutations uncovered from cancerous tissues ablated their growth inhibition, WT and two mutant FOXP3 cDNA were transfected into SKBr3 and MCF7 cell lines. In both cell lines, the mutants had a greatly reduced ability to suppress tumor growth.

To test whether repression of ErbB2 is related to the tumor suppressor activity of the FOXP3 gene in the ErbB2$^+$ cancer cell line, TSA cells were transfected with mouse CMV promoter-driven ErbB2 cDNA cloned into the pcDNA6 vector and evaluated their susceptibility to FOXP3-mediated growth suppression. In this setting, the expression of ErbB2 was resistant to FOXP3-mediated repression. If repression of endogenous ErbB2 is critical for FOXP3-mediated tumor suppression, ectopic expression of ErbB2 should alleviate the growth inhibition by FOXP3.

While the pcDNA6-vector-transfected TSA cells remained susceptible to FOXP3-mediated repression, the ErbB2-transfected TSA cells were completely resistant. In contrast, transfection of c-Myc barely alleviated the growth inhibition by FOXP3. These results suggested that FOXP3 suppresses TSA growth by repressing transcription of ErbB2.

TSA cells were transfected with either empty vector or V5-tagged FOXP3 cDNA. The stable transfectant cell lines were selected by G-418. The vector and FOXP3-V5-transfected cell lines were injected into syngeneic BALB/c mice, which were then observed for tumor growth and mouse survival.

Results showed that FOXP3-transfectants showed reduced growth in vivo. The mice that received TSA-vector cells became moribund earlier with higher incidence, while about 50% of the mice that received the FOXP3-V5-transfected cells survived more than 7 weeks. Similarly, FOXP3-transfected 4T1, a mouse mammary cancer cell line also showed reduced tumorigenicity in vivo.

These results demonstrated that, for TSA cell line which has ErbB2 over-expression, repressing the ErbB2 locus is responsible for FOXP3's tumor suppressor activity. The requirement for continuous expression of ErbB2 is best explained by the concept of oncogene addiction (Weinstein, *Science* 297: 63-64 (2002)). However, FOXP3 can also suppress the growth of tumor cell lines that do not grossly overexpress HER-2/ErbB2, such as MCF-7.

In addition to mammary cancer cell lines, it was demonstrated that FOXP3 expression suppressed growth of thymoma cell line EL4. Thus, FOXP3 can suppress growth of multiple lineage of tumors.

In an effort to identify other potential FOXP3 targets, a FOXP3-Tet-off MCF-7 cell line was produced that expresses FOXP3 upon removal of tetracycline. Using the most current version of Entrez Gene-based CDFs for a more accurate GeneChip analysis (Dai et al., *Nucleic Acids Res* 33: e175 (2005)), it was found that wide-spread changes in the expression of genes that are involved in several pathways critical for cancer cell growth. The genes with >2.0 fold changes that occurred on day 2 and >4.0 changes on day 4 of FOXP3 induction were analyzed by Ingenuity Pathway.

Ingenuity Pathway analysis indicated that FOXP3-regulated genes belong to multiple cellular pathways related to the process of cancer development. Interestingly, when we used the GeneGo MetaCore knowledgebase to analyze genes that related to the ErbB2 signaling pathway, we found that FOXP3 down-regulated 10 genes in this pathway. With the notable exception of b-Myb and c-Myb, the down-regulation was not likely related to FOXP3-mediated ErbB2 repression, as the majority of the genes are not known transcriptional targets of ErbB2. Thus, FOXP3 can suppress ErbB2 signaling and tumor growth by mechanisms in addition to ErbB2 repression. These data provide a plausible explanation for the tumor suppressor activity of FOXP3 in breast cancer cell lines that do not substantially overexpress HER-2.

Example 7

Identification of Compounds that Induce FOXP3 Expression in Cancer Cells and their Therapeutic Effect A method was developed to induce FOXP3 expression in cancer cells by activating JNK, P38 and ATF2. Briefly, breast cancer and thymoma cell lines were treated with activators of JNK, P38 and ATF2, such a emetine and anisomycin for 14 hr to 2 days. The cells were analyzed for expression of FOXP3-encoding mRNA by RT-PCR.

Results showed strong induction of FOXP3-encoding mRNA in various cancer cell lines, including thymoma cell line BW5147, transformed thymic epithelial cell 61.7, and breast cancer cell lines TSA by anisomycin and emetine.

Given the impact of FOXP3 activity on tumor growth and cell death, these compounds were also tested for their ability to kill cancer cells. Data demonstrated that within 48 hours, anisomycin treatment killed a substantial percentage of cancer cells in all three breast cancer cell lines tested, including MCF-7, BT474, and TSA. The IC50 ranges between 30-100 ng/ml.

These data provide a method to screen compounds that induce FOXP3 expression and are cytocidal for cancer cells. In order to carry out large scale screening, it is possible to obtain cells from mice in which the FOXP3 gene is modified to also express a detectable reporter protein, such as for example, green fluorescence protein (GFP) or luciferase. In this way, a library of test compounds are incubated with the cells for a given period of time and the level of FOXP3 transcription is monitored by the amounts of reporter protein. By comparing the structure features of the compounds identified, additional compounds are designed based on the relative activity of the active compounds.

Example 8

Identification of the Mechanism by which Anisomycin Induces FOXP3

To identify the mechanism by which anisomycin induced FoxP3, the activation of ATF2, p38, and JNK upon treatment with either anisomycin or PMA was compared. 4T1 cells were treated with either vehicle control, anisomycin (1 µg/ml) or PMA (0.5 µg/ml). Western blots of the cell lysates were obtained using antibodies specific for phospho-ATF2, phospho-p38, ATF2, phospho-JNK1/2, phospho-c-Jun. Levels of beta-actin were used as loading controls.

While both PMA and anisomycin activated p38 and ATF2, PMA failed to activate JNK and its down-stream substrate c-Jun. These data raised the possibility that JNK signal pathway may contribute to FoxP3 induction.

Cells of a mammary tumor cell line were treated with anisomycin in conjunction with inhibitors of overlapping specificity. Specifically, 4T1 cells were treated with vehicle control, anisomycin (1 μg/ml) or PMA (0.5 μg/ml) in the presence or absence of inhibitors (2 μg/ml): SP10096 (SP), SB203580 (SB), and PD9786 (PD). Western blots of the cell lysates were obtained using antibodies specific for phosphor-ATF2, phospho-p38, ATF2, phospho-JNK1/2, phospho-c-Jun. Levels of beta-actin were used as loading controls.

SP efficiently inhibited the activation of ATF2, JNK, and c-Jun by anisomycin and prevented the induction of FoxP3. On the other hand, SB inhibited p38α completely but inhitibed ATF2 and JNK only partially. Also, SB reduced, but did not eliminate, FoxP3 induction. PD, which had no effect on any of the three substrates, also failed to inhibit FoxP3 induction.

Example 9

Involvement of ATF2 and JNK but not P38 in FoxP3 Induction

Lentiviral vectors were generated expressing shRNA for JNK1, JNK2, ATF2 or p38α to test the function of the three components. The lentivirus-based shRNA expressing vectors were created by introducing the murine U6 RNA polymerase III promoter and a murine phosphoglycerate kinase promoter (pGK)-driven EGFP expression cassette into a vector of pLenti6/V5-D-TOPO back bone without CMV promoter. Hairpin shRNA sequence of FoxP3, JNK1, JNK2, p38, and Atf2 (FoxP3: 5'-aagccatggcaatagttcctt-3' (SEQ ID NO: 168); FOXP3, 5'-gcagcggacactcaatgag-3' (SEQ ID NO: 169), JNK1,2: 5'-agaaggtaggacattcctt-3' (SEQ ID NO: 170); p38: 5'-aataccgagagttgcgtctgc-3' (SEQ ID NO: 171); Atf2: 5'-ct-tctgttgtagaaacaac-3' (SEQ ID NO: 172)) were cloned into the lentiviral shRNA expressing vectors by restriction sites of ApaI and EcoRI.

The lentiviral vectors with or without the shRNA were introduced into 4T1 cells. The efficacy of shRNA silencing was assayed by Western blotting using antibodies specific for JNK1/2, ATF2, or p38-alpha. Levels of beta-actin were used as loading controls. 4T1 cells were treated with a vehicle control or anisomycin (0.1 μg/ml) for 16 hours. The FoxP3 expression levels were determined by real time (RT)-PCR using primers spanning from start codon to stop codon.

While the inhibition of p38α expression had only a slight effect on FoxP3 induction, silencing either JNK or ATF2 resulted in a significant reduction of the FoxP3 transcripts. These data provide important genetic evidence for the involvement of JNK and ATF2 in anisomycin-induced FoxP3 expression.

Example 10

ATF2 is Responsible for Expression of FOXP3 in Mammary Epithelial Cells

ATF2± mice were obtained from the frozen embryo bank of the Jackson Laboratories and were crossed to produce ATF2+/+ and the ATF2−/− mice. A previous report indicated that the only a small fraction of the ATF2−/− mice survive to adulthood (Reimold et al., Nature 379: 262-265 (1996)). Two independent primary cultures were obtained from two ATF2−/− females. Specifically, mouse mammary fat pads were removed from 6 to 8-week-old virgin female mice and minced into small pieces. After collagenase digestion at 37° C. in a shaking incubator in DMEM medium supplemented with 5% fetal calf serum (FBS), cells were sieved through a 70-μm cell strainer (BD Falcon) to obtain a single cell suspension. The cells were cultured in DMEM medium supplemented with 10% FBS and 10 ng/ml epithelial growth factor (EGF). At day 3 of culture, fibroblast cells were removed by a short digestion with 0.05% trypsin-EDTA as less adherent cells.

The cultures were observed for morphology and a higher cellular density of the ATF2−/− culture was noted. Also, the epithelial origin of the cultures was demonstrated by the expression of CK19, as shown by Western blotting with antibodies specific for CK19. Since T cells are the major source of FoxP3 transcripts in vivo, the primary culture was tested for CD3 transcripts by Western blotting with antibodies specific for CD3 and was confirmed to have an absence of T cell contamination.

The primary cultures were then assayed for expressioin of FOXP3 protein by Western blotting cell lysates of the cultures with antibodies specific for FOXP3. The primary transcripts also were assayed for expression of FOXP3 by real-time PCR.

ATF2+/+ epithelial cultures expressed significant amounts of FOXP3 transcripts, which were further induced by the treatment of anisomycin. ATF2−/− cells, on the other hand, had no detectable FoxP3 transcripts and were completely refractory to anisomycin. These data revealed an essential role for ATF2 in both constitutive and inducible expressions of FoxP3.

Example 11

Identification of the FoxP3 Enhancer Associated with ATF2 and c-Jun

In order to study the mechanism of ATF2/c-Jun-mediated induction of FoxP3, chromatin immunoprecipitation (ChIP) was carried out as described in (Im et al., Nat Med 5: 412-417 (1999)) to identify an anisomycin-inducible binding site of the FoxP3 locus. Briefly, 4TI cells were treated with vehicle or anisomycin for 2 hours. The cells were sonicated and the chromatin was fixed with 1% paraformaldehyde. Anti-phospho-c-Jun or anti-phosphor-ATF2 antibodies or control rabbit IgG were used to precipitate chromatin associated with these proteins. The amounts of the specific DNA fragments were quantitated by real-time PCR and normalized against the genomic DNA preparation from the same cells. Immunoprecipitation with either phospho-ATF2 antibodies or phospho-c-Jun antibodies followed by Western blotting with the immunoprecipitating antibodies demonstrated that anisomycin-induced phospho-ATF2 and phospho-c-Jun were efficiently precipitated by antibodies. Untreated 4T1 cells barely had detectable amounts of phospho-ATF2 and phospho-c-Jun in the nuclei. Following treatment with anisomycin, a major increase of phospho-ATF2 and phospho-c-Jun were detected in the nuclear fraction.

In order to identify the FoxP3 sequence associated with p-ATF2 and p-c-Jun, the 5' sequence of the FoxP3 gene was analyzed and 14 potential AP1 and CREB sites were identified. PCR primers were designed across the 10.4 kb regions, and the amount of each PCR product was normalized against that amplified from the input DNA under different conditions: untreated/precipitated with anti-phospho-ATF2 antibodies, anisomycin treated/precipitated with anti-phospho-ATF2 antibodies, untreated/precipitated with anti-phospho-c-Jun antibodies, anisomycin treated/precipitated with anti-phospho-c-Jun antibodies, and pooled/precipitated with IgG antibodies.

Two potential sites for ATF2/cJun interaction as demonstrated by the increase in % input upon anisomycin treatment were revealed from this experiment. The first is hereinafter referred to as P2, which is 4.8 kb 5' of exon 1. The second and stronger binding site referred to hereinafter as P10 is 4.2 kb 3' of exon 1. Importantly, while the P2 ATF2/cJun association is not inducible by anisomycin, the P10 binding is enhanced by more than 2-fold by anisomycin. Moreover, comparison of mouse and human FoxP3 sequence revealed that the P10, but not the P2 site is highly conserved. Therefore, P10 became the focus as a potential site for p-ATF2 and p-cjun interaction.

Sequencing comparison identified a typical AP1 site within the P10. In order to directly demonstrate interactions of ATF2 and c-Jun to the FoxP3 promoter, an oligonucleotide probe containing conserved AP1 site, as well as two control oligos with mutations in the AP1 site, were radio-labeled and tested for binding to nuclear extracts. The sequence of nonmutated probe (P10) is agatggacgtcacctaccacatcacgg (bold letters for core AP1 sequence; SEQ ID NO: 173), that for P10-Mt1 is agatggacgtctgcgcccacatcacgg (bold letter indicate mutations; SEQ ID NO: 174), while that for P10-Mt2 is agatggacgtcgacgcccacatcacgg (SEQ ID NO: 175).

The nuclear extracts from anisomycin-treated, but not those from the untreated 4T1 cells, showed strong interaction with the nonmutated P10 probe. The specificity was confirmed by the fact that mutations in the AP1 site significantly reduced the binding. Furthermore, the involvement of ATF2 and c-Jun was demonstrated by the fact that antibodies specific for ATF2 or c-Jun abolished the binding of nuclear extracts to the nonmutated probe. Furthermore, the role of ATF2 and c-Jun activation is consistent with observed inhibition by SP. Thus, both ChIP and electrophoresis mobility-shift assay identify a specific AP-1 site with 4.2 kb 3' of the TSS, which binds to both p-ATF2 and p-cjun by anisomycin-inducible fashion.

To test whether the P10 sequence was a functional FoxP3 enhancer, a series of constructs consisting of the basal promoter and putative enhancer elements were generated. A 265 bp sequence 5' of the transcriptional start site (TSS) of the FoxP3 locus plus 50 bp down-stream of TSS is sufficient to convey significant basal promoter activity. This fragment was therefore chosen to measure the enhancer activity. An addition of three copies of P2 fragment increased the promoter activity by about 2-fold, which suggests that P2 is at best a weak enhancer. Inclusion of three copies of P10 sequences, however, increased the FOXP3 promoter activity by 10-fold. This appears uni-directional as the inversion of the P10 fragment eliminated its enhancer activity. Moreover, the involvement of AP1 site in P10 was confirmed as a mutation of the AP1 site significantly reduced the enhance activity. Moreover, addition of P2 to P10 failed to further enhance the promoter activity. Taken together, our data demonstrated that anisomycin induced ATF2/c-Jun interaction with a specific enhancer within the intron 1 of the FoxP3 gene.

Example 12

A critical Role for ATF2-FoxP3 Pathway in Anisomycin-induced Apoptosis and the Therapy of Breast Cancer Recent studies have demonstrated that induced expression of FoxP3 caused apoptosis of breast cancer cell lines (Zuo et al., Cell 129: 1275-1286 (2007); Zuo et al., J Clin Invest 117: 3765-3773 (2007); and Reimold et al., 1996, supra). To determine whether anisomycin treatment causes apoptosis of breast cancer cells, the cytotoxic effect of anisomycin on several of breast cancer cell lines was measured by MTT assay. $10^4$ cells/well of mouse cell line (TSA) or human breast cancer cell lines (TB474 or MCF7) were cultured in the presence of 25, 50, 100, 200, 400, or 800 ng/ml anisomycin for 48 hours. The amounts of viable cells were determined by MTT assay, with viability of the untreated cells defined as 100%. Both mouse (TSA) and human breast cancer cell lines (BT474, MCF-7) were highly susceptible to anisomycin, with an IC50 between 50-100 nM.

Cells were stained for activated Capsase 3 and also tested for DNA contents. The % of gated cells was apoptotic based on their sub-2C DNA contents. The reduced viability was due to apoptosis as revealed by the increased expression of active caspase 3 in TSA cells with less than 2C DNA contents.

Given the critical role for ATF2 in FoxP3 induction, the contribution of ATF2 to anisomycin-induced cell death was tested by comparing the dose response to anisomycin in cells transfected with vector alone or those with ATF2 shRNA. TSA cells were transduced with lentiviral vector encoding either scrambled shRNA of shRNA specific for ATF2 or FoxP3. The transfected cells were enriched by short-term treatment of blastcidin at a dose of 6.5 µg/ml and subject to treatment of a different dose of anisomycin (0, 20, 40, or 80 ng/ml). The viability was measured by MTT assay. ATF2 shRNA increased resistance to anisomycin by 4-fold. Likewise, the FoxP3 shRNA also increased drug resistance by a similar extent. These data demonstrate a critical role for the ATF2-FoxP3 pathway in anisomycin induced cell-death of breast cancer cells.

To test whether induction of FoxP3 by ATF2-FoxP3 pathway can be explored for breast cancer therapy, cells ($5 \times 10^5$) of the TSA cell line were injected into the mammary fat pads of BALb/c mice. Five days later, when the cancer cells established locally, the mice were intraperitoneally treated with vehicle control or anisomycin every 3 days for 8 times at a dose of I mg/mouse. The dose did not give obvious side effects and is about $\frac{1}{10}$ of the IC50 in mice. The growth of the TSA tumor cells in syngeneic mammary pad was nearly completely abrogated by anisomycin. These data demonstrate the potential of ATF2-FoxP3 pathway in the therapeutic development for breast cancer.

Example 13

Induced Expression of FOXP3 is Sufficient to cause Apoptosis of Breast Cancer Cell Lines It was demonstrated that transfection of FoxP3 can repress tumor cell growth (Zuo et al., Cell 129: 1275-1286 (2007)). To confirm that FoxP3 expression actively causes tumor cell death, a Tet-off system, in which the expression of FOXP3 was induced when the cells were placed in doxycyclin-free medium, was generated. Cells cultured in the doxycyclin-free medium expressed FOXP3 and essentially all of the cells underwent programmed cell death. These data demonstrate that FOXP3 expression can potentially kill tumor cells.

Example 14

Large Scale Screen for Compounds that Specifically Induce FOXP3 Expression

Primary epithelial cells from FoxP3-GFP knockin mice are isolated and used as the primary read out for screening. Compounds from the National Cancer Institute are provided in 96-well plates as a first library. In brief, $10^4$ cells/well of breast epithelial cells are added to the 96-well plates containing the compounds. After 48 hours of culture, the plates are scored for fluorescence intensity. Those that exhibit 2-fold increase in fluorescence are selected for further testing. Once the effects are confirmed, the compounds are tested for ATF-2-dependent FOXP3 induction using primary epithelial cells that are ATF-2-/- FoxP3$^{gfp/gfp}$.

Once lead compounds are identified, the compounds are tested for in vitro cytotoxicity for TSA cells by MTT assay. The TSA that are transfected with siRNA for either ATF-2 or FoxP3 are used as a control. By this series of screening, 2-3 lead compounds that inhibit growth of breast cancer cell lines by inducing FoxP3 through an ATF-2-dependent mechanism are expected.

Example 15

FOXP3 is a Transcriptional Repressor of MYC Oncogene

Cell lines containing the vector of FOXP3-tetoff (Zuo et al., 2007, supra) were cultured in the presence or absence of doxycyclin for 0-96 hours. Specifically, MCF-7 cell lines with Tet-off induction of either GFP or GFP+FOXP3 cDNAs were cultured in the absence of doxycyclin for the time periods 0, 24, 30, 48, 72, or 96 hours. The total RNA from the cells was isolated for quantitation of FOXP3 transcripts by real-time PCR (Applied Biosystems ABI Prism 7500 Sequence Detection System, Applied Biosystems, Foster City, Calif.). The SYBR (Applied Biosystems, Foster City, Calif.) green fluorescence dye was used in this study. The average relative expression was determined using the comparative method ($2^{-\Delta\Delta Ct}$) or was calculated by plotting the Ct (cycle number) against the standard curve and comparing this to an endogenous control. The primer sequences (5'-3') are listed in Table 3.

TABLE 3

| Primer Name | Sequence | SEQ ID NO: |
|---|---|---|
| Human CMYC-ChIP-1 F | TCAGAAGGCAACTTCCATGGT | 110 |
| Human CMYC-ChIP-1 R | AGATGGAGTTACAGGCGTGAA | 111 |
| Human CMYC-ChIP-2 F | TGAAACCTGGCTGAGAAATTG | 112 |
| Human CMYC-ChIP-2 R | TGCGGGAGGCGTCTGTTTA | 113 |
| Human CMYC-ChIP-3 F | TCATCACCTCTGAAACCTTGG | 114 |
| Human CMYC-ChIP-3 R | CGGGAGGTAAGAAGAAGTGGA | 115 |
| Human CMYC-ChIP-4 F | GGTGACTCACTTGGGAATCG | 116 |
| Human CMYC-ChIP-4 R | TATTCCCATAGCCAAGCTCCA | 117 |
| Human CMYC-ChIP-5 F | TGTGTCACTCAGAGTGGCTGT | 118 |
| Human CMYC-ChIP-5 R | AATTCCAAGCCCTCATGCA | 119 |
| Human CMYC-ChIP-6 F | TTCCAAAAGCCTGACAGCAA | 120 |
| Human CMYC-ChIP-6 R | TCACCCTTGGTTGTTTTCAC | 121 |
| Human CMYC-ChIP-7 F | TCCGCCATCTTTAGCAACTT | 122 |
| Human CMYC-ChIP-7 R | AAATGAGTGCTCTCCACAGGG | 123 |
| Human CMYC-ChIP-8 F | CAAAATAAAAAATCCCGAGGG | 124 |
| Human CMYC-ChIP-8 R | AACCCGCAAACGTGTATTCA | 125 |
| Human CMYC-ChIP-9 F | CGTAGTTAATTCATGCGGCT | 126 |
| Human CMYC-ChIP-9 R | TTTCTTTTCCCCCACGCC | 127 |
| Human CMYC-ChIP-10 F | ATGCTGAGATGAGTCGAATGC | 128 |
| Human CMYC-ChIP-10 R | TTGACAAGTCACTTTACCCCG | 129 |
| Human CMYC-ChIP-11 F | CACCAAGACCCCTTTAACTCA | 130 |
| Human CMYC-ChIP-11 R | AAGTTCTCCTCCTCGTCGCA | 131 |
| Human CMYC-ChIP-12 F | CGTTTATAGCAGTTACACAGAATTTCA | 132 |
| Human CMYC-ChIP-12 R | GGCTCAATGATATATTTGCCAGT | 133 |
| Human CMYC-ChIP-13 F | CCTGGGCAACAGAATGAGACT | 134 |
| Human CMYC-ChIP-13 R | TTCACCTCCTAACTGCTGCTT | 135 |
| Human CMYC-ChIP-14 F | AGCCTGGGTGACAAAGTGAAA | 136 |
| Human CMYC-ChIP-14 R | GCACAGCCAGATTGAAACAA | 137 |
| Human FOXP3-realtime-F | TACTTCAAGTTCCACAACATGCGACC | 138 |
| Human FOXP3-realtime-R | CGCACAAAGCACTTGTGCAGACTCAG | 139 |

TABLE 3-continued

| Primer Name | Sequence | SEQ ID NO: |
|---|---|---|
| Human CMYC-realtime-F | ATTCTCTGCTCTCCTCGACG | 140 |
| Human CMYC-realtime-R | TGCCTCTTTTCCACAGAAACA | 141 |
| Human GAPDH-realtime-F | CCCCTTCATTGACCTCAACTACAT | 142 |
| Human GAPDH-realtime-R | CGCTCCTGGAAGATGGTGA | 143 |
| Human FOXP3-cDNA-F | AAGCCAGGCTGATCCTTTTCT | 144 |
| Human FOXP3-cDNA-R | TCTGCCTCCCACCAGTTTG | 145 |
| Human CMYC-motif-Del-F: | TTCATGCGGCTCTCTTACTCATCCTAGAGCT | 146 |
| Human CMYC-motif-Del-R: | GAGTAAGAGAGCCGCATGAATTAACTACGC | 147 |
| Human CMYC-motif-Mut-F: | TTCATGCGGCTCTCTTACTCAAAAGGGATCCT | 148 |
| Human CMYC-motif-Mut-R: | GAGTAAGAGAGCCGCATGAATTAACTACGC | 149 |
| Mouse FOXP3-realtime-F | AAAAGGAGAAGCTGGGAGCTA | 150 |
| Mouse FOXP3-realtime-R | TGAGTACTGGTGGCTACGATG | 151 |
| Mouse cMyc-realtime-F | CTAGTGCTGCATGAGGAGACA | 152 |
| Mouse cMyc-realtime-R | TGTGCGGAGGTTTGCTGT | 153 |
| Mouse HPRT-realtime-F | CAGGCCAGACTTTGTTGGAT | 154 |
| Mouse HPRT-realtime-R | GCGCTCATCTTAGGCTTTGT | 155 |
| Mouse Ck19-realtime-F | ACCCTCCCGAGATTACAACC | 156 |
| Mouse Ck19-realtime-R | CAAGGCGTGTTCTGTCTCAA | 157 |
| Mouse FOXP3-KODNA-PrimerA-F | AACTTCTAGGGACCAGGGGCT | 158 |
| Mouse FOXP3-KODNA-PrimerA-R | CAAGTACCCCACCCTGCTTA | 159 |
| Mouse FOXP3-WTDNA-PrimerB-F | TGCTCCATAAACGATTATGGC | 160 |
| Mouse FOXP3-WTDNA-PrimerB-R | ATGAAGACCCTGGGAATCAA | 161 |
| Mouse FOXP3-loxP-F | AAGCCCCAGTAGAATCAGCAA | 162 |
| Mouse FOXP3-loxP-R | TGTCGTGAATGTGGGGTGAT | 163 |
| Mouse PB-Cre4-C001-F | ACCAGCCAGCTATCAACTCG | 164 |
| Mouse PB-Cre4-C002-R | TTACATTGGTCCAGCCACC | 165 |
| Mouse PB-Cre4-C003-F | CTAGGCCACAGAATTGAAAGATCT | 166 |
| Mouse PB-Cre4-C004-R | GTAGGTGGAAATTCTAGCATCATCC | 167 |

Induction of FOXP3 expression resulted in a rapid down regulation of MYC mRNA.

To understand the mechanism by which FOXP3 represses MYC, ChIP was used to identify the site of FOXP3 binding in the MYC promoter. ChIP was carried out according to a published procedure (Im et al., *Methods Mol Biol* 284: 129-146 (2004)). Briefly, the FOXP3-transfected Tet-off MCF cells were cultured in the absence of doxycyclin for 48 hours and used as a source of chromatin for ChIP. The cells were sonicated and fixed with 1% paraformaldehyde. The anti-FOXP3 and anti-IgG antibodies were used to pull down chromatin associated with FOXP3. The amounts of the specific DNA fragment were quantitated by real-time PCR and normalized against the genomic DNA preparation from the same cells. The ChIP real-time PCR primers are listed in Table 3.

Quantitative PCR analysis indicated that, despite the abundance of forkhead binding sites, a strong binding of FOXP3 centered around 0.2 kb downstream from the transcription starting site (TSS). To test the significance of this site for the repression, deletional analysis was carried out to map the region that conveys susceptibility to FOXP3 repression.

Little, if any repression by FOXP3 was observed when the reporter was truncated before the forkead binding site at the 0.2 kb region (Fragment 1 (F1): 0 to +401; F2: −184 to +401). Strong inhibition was observed when the binding motif is included (F3: −346 to +401; F4: −698 to +401; and F5: −1059 to +401). Additional sequence did not increase the efficiency of repression. In addition, when the forkhead site at −0.2 kb was either deleted or mutated, the repression is completely abrogated. These data demonstrated that FOXP3 repression MYC promoter activity by interacting with the forkhead motif at the −0.2 kb of the MYC promoter.

FoxP3 is expressed at high levels in mouse prostate epithelial cells (Chen et al., *J. Immunol.* 180: 5163-5166 (2008)). To test if this is also the case for human prostate tissue, a tissue microarray sample (University of Michigan and Biomax (US Biomax, Inc., Rockville, Md.) was stained with normal prostate samples. Briefly, ABC detection system was used for immunostaining according to the manufacturer's protocol (Vectastain Elite ABC, Burlingame, Calif.). The incubation time for primary antibody FOXP3 (1:20), cMyc (1:200) and Ki67 (1:100) was overnight at room temperature. After incubation with primary antibody, staining was followed by ABC detection system using biotinylated anti-mouse immunoglobulin for FOXP3, cMyc and Ki67 at a dilution of 1:200 and avidin-biotin peroxidase macromolecular complex at 1:100, with an incubation time of 30 min for each step. A wash of 10 min using PBS was added in between each step. AEC was used as chromogen. Finally, the slides were counterstained with hematoxylin and mounted in xylene mounting medium for examination. The FOXP3 mAb stained human prostate epithelium. Consistent with a repressor function of FOXP3 for MYC, a lack of MYC was observed in the normal prostate human prostate epithelial cells (HPEC).

To determine whether the endogenous FOXP3 in prostate epithelial cell lines is responsible for MYC repression, the FOXP3 locus was silenced with a lentiviral vector encoding shRNA for FOXP3. Human Prostate Epithelial Cells (HPEC) were purchased from Lonza Group Ltd (Switzerland) and were cultured with medium. An early passage of the HPEC were infected with lentivirus expressing either control shRNA or FOXP3 shRNA vector as described in Zuo et al., 2007, supra. Uninfected cells were removed by drug selection. At one week after infection, the levels of FOXP3 or MYC mRNA were quantitated by RT-PCR. Western blotting was also carried out using anti-FOXP3 or -MYC antibodies. Beta actin was used as a loading control. FOXP3 shRNA caused a major reduction in the expression of FOXP3 mRNA. Correspondingly, the level of MYC transcript was significantly elevated by FOXP3 ShRNA.

To determine whether FOXP3 inhibits expression of MYC in prostate cancer cell lines, FOXP3 cDNA was transfected into prostate cancer cell lines Du 145 and PC3 (obtained from American Type Culture Collection (ATCC)) and the lysates of the transfected cells were measured for levels of MYC protein by Western blot. Beta actin was used as a loading control. FOXP3 transfection almost completely eliminated MYC in the two cell lines.

The expression of FOXP3 and MYC in tissue microarray samples consisting of 214 cases of prostate cancer was compared in order to determine whether lack of FOXP3 expression correlated with MYC elevation. TMA of prostate cancer tissues were stained by immunohistochemistry with antibodies against FOXP3 or MYC. FOXP3+ and FOXP3-tumor samples were analyzed for MYC expression and compared using a Chi-square test. While 27.6% of FOXP3$^+$ cancer expressed elevated levels of MYC, nearly 72.4% of the FOXP3$^-$ tumors over-expressed MYC. Thus, FOXP3 down regulation is suggested to be an important factor leading to elevation of MYC in prostate cancer.

Example 16

FOXP3 Inhibits Growth of Prostate Cancer Cell Lines

Given the significant role for MYC in cancer cell proliferation, the consequences of FOXP3 expression on the colony-forming capapcity of prostate cancer cells were tested.

DU145 and PC3 cells were transfected with either control vector or FOXP3 cDNA. After drug selection for 2 weeks, the drug-resistant colonies were counted under a microscope. When the FOXP3 cDNA was ectopically expressed in PC3 and Du145, a significant reduction of colonies formed from $10^4$ cells was observed.

In order to determine whether the growth inhibiton was mediated by repression of MYC, FOXP3 with MYC cDNA was co-transfected into Du145 cells. The cells were transfected with either pcDNA6-blasticidin vector or MYC cDNA and either the pEF1-G418 vector or FOXP3 cDNA and selected with blasticidin and G418 for 3 weeks. The viable colonies were visualized after staining with the crystal violet dye. The representative plate showed that abrogation of FOXP3-mediated suppression by MYC.

Example 17

Somatic Deletion and Epigenetic Silencing of the FOXP3 Locus Down-regulate FOXP3 Expression The strong growth inhibition of prostate cancer cell lines in combination with the potent MYC repressor activity of FOXP3 make FOXP3 a prime candidate of tumor suppressor for prostate cancer. As a first test for the hypothesis, the expression of FOXP3 in normal and prostate tissue was evaluated by both immunohistochemistry of tissue microarray. Immunohistochemistry with anti-FOXP3 mAb (Abcam, ab20034, Clone 236A/E7) can detect nuclear FOXP3 staining in more than 70% of the benign prostate tissues tested. In contrast, only 34% of prostate cancer samples show nuclear FOXP3 staining.

To substantiate this observation, microdissection was used to obtain benign prostate tissue and cancer tissues from the same patients and compared the FOXP3 mRNA. Since inflammatory T cells are a major sources of FOXP3 expression, areas of inflammation were carefully avoided for dissection. Briefly, tissue sections from frozen mouse or human prostate samples (obtained from the Prostate Cancer Tissue Bank of Ohio State University) were cut (8 µm thicknesses) and transferred to non-polylysine-coated glass slides. The slides were stained with Harris hematoxylin for 50 seconds and Eosin for 30 seconds and then dried in a laminar flow hood for 5 to 10 min prior to microdissection. Five thousand target cells will be Laser-capture micro-dissection (LCM) from target tissues using Arcturus PixCell II system (Arcturus, Santa Clara, Calif.) with an Olympus IX-50 microscope. The LCM cell procurement time for RNA was always less than 15 minutes. RNA was extracted using the Picopure RNA extraction kit (Molecular Devices, Sunnyvale, Calif.) and amplified by RT-PCR. Genomic DNA was extracted from microdissected cells using PicoPure DNA Isolation kit (Molecular Devices, Sunnyvale, Calif.). After normalizing against a house-keeping gene (GAPDH), 15/20 cases show 2-10 fold reduction of FOXP3 mRNA in comparison to the benign tissues. Thus, reduced FOXP3 expression is widespread among prostate cancer samples.

Recent studies suggested that DNA methylation is involved in limiting FOXP3 expression (Floess et al., *PLOS Biol* 5, e38 (2007); Kim and Leonard, *JEM* 204: 1543-1551 (2007)). DNA comprising the FOXP3 gene was purified from microdissected samples were tested for % methylation by pyrosequencing. Specifically, amplification and sequencing primers for the FoxP3 promoter and intronic CpG islands were designed using MethPrimer software. FoxP3 Promoter: Forward (and sequencing primer): 5' AGTAAAGGGTAGT-TGGAAGGTAAAG (SEQ ID NO: 176); Reverse primer: 5' Biotinylated-AAAAACAAAAAATCCCATCCTAAAT (SEQ ID NO: 177). FoxP3 intron: Forward (and sequencing primer): 5' TTGGGTTAAGTTTGTTGTAGGATAG (SEQ ID NO: 178) Reverse primer: 5' Biotinylated—ATCTAAAC-CCTATTATCACAACCCC (SEQ ID NO: 179). Each 25 ul PCR reaction (containing 2 ul bisulfite modified DNA, 0.2 uM forward primer, 0.4 uM biotinylated reverse primer, and 15 ul Qiagen Master Mix) was subjected to the following cycling conditions: 1 cycle of 95° C. for 15 min, 44 cycles of 95° C. for 30", 53° C. for 30", 72° C. 30", and 1 cycle 72° C. for 10'.

Pyrosequencing was performed using PyroGold reagents and the PyroMark MD instrument (Biotage). Briefly, 5 ul of biotinylated PCR product was immobilized onto 2 uL streptavidin-Sepharose beads (Amersham Biosciences) diluted in Binding Buffer. After applying a vacuum to collect the beads, the non-biotinylated DNA strand was removed using Dissociation Buffer (0.2 M NaOH) and the single stranded biotinylated product was washed, and placed onto a PSQ HS 96 plate containing 0.4uM sequencing primer. The sequencing primer was annealed to the ss DNA product at 90° C. for 2', cooled, and subjected to the sequencing reaction using nucleotide volumes recommended for CDTs, and a nucleotide dispensation order generated by the PyroQ CpG software (bottom sequence of each pyrogram). In addition to a small CpG motif in the FOXP3 intron 1 which was reported to be involved in regulating FOXP3 expression in T cells, a prominent CpG island 5' of the FOXP3 promoter was also identified.

Using a quantitative pyrosequencing method for FOXP3 analysis, the level of methylation in both the intronic CpG motif and the CpG island was quantitated in the promoter region of FOXP3, using DNA from 17 cases of micro-dissected normal and cancerous tissues. While no significant difference in methylation in the intronic CpG motif was observed between benign and cancerous tissues, a highly significant increase in the FOXP3 5' CpG methylation was observed in the cancer samples (P=0.0075). Morover, the increase in methylation strongly correlate with reduction of FOXP3 expression. To verify the significance of DNA methylation, prostate cancer cell lines PC3 and Du145 were treated with a methyltransferase inhibitor (5-aza-2'-deoxycytidine (5-AZA)). 5-AZA-treatment caused a two-fold induction of the FOXP3 gene in the prostate cancer cell lines tested.

Another mechanism to inactivate FOXP3 expression is by gene deletion. To explore this possibility in prostate cancer samples, fluorescence in situ hybridization (FISH) was used to determine deletion of the FOXP3 gene in the prostate cancer tissue. The FISH was carried out as previously described (Zou et al., 2007, supra). Briefly, the FISH for FOXP3 deletion was done using BAC clone RP1 1-344014 (ntLocus X: 48,817,975-48,968,223), which was verified by PCR to contain the FOXP3 gene, using TMA and frozen samples. 23 of 145 samples (16%) tested show deletion of FOXP3 gene. Among them, 18/23 case have a single copy of X chromosome. However, 5/23 showed an increase in the number of X-chromosomes. In cells with X polysomy and FOXP3 deletion, FOXP3 deletion was complete in all X-chromosomes. Thus, X-chromosome duplications likely occurred after deletion of FOXP3.

Example 18

Somatic Mutations in Prostate Cancer Functionally Inactivate FOXP3

In order to determine whether FOXP3 was somatically mutated in primary prostate cancer samples, cancerous and normal prostate tissues were isolated from the same patients and were compared to the DNA from exons and some exon-intron junction.

DNA samples from cancerous and benign tissues dissected from 20 cases of prostate cancer tissues were amplified by PCR and sequenced. The somatic mutants were identified by comparing DNA sequence of normal and cancerous tissues from the same section. More specifically, both normal and malignant prostate tissues were isolated from frozen section under LCM. Genomic DNA was extracted from microdissected cells using PicoPure DNA Isolation kit (Molecular Devices, Sunnyvale, Calif.). Somatic mutations were identified by comparing FOXP3 sequences of cancerous tissue to those of normal tissues from the same patients. All DNA were isolated from frozen tissues and were amplified by PCR. The bulk PCR products were sequenced from both forward and reverse directions. The sequencing was repeated at least twice from independent PCR reactions. The mutated PCR products were cloned and 5-10 clones were sequenced to confirm these mutations.

The sequencing analyses demonstrate single base-pair changes in 5/20 samples tested. Among them, four were missense mutations (V97A, N196I, G203R, and K227R) while one caused a change in intron 6. The tumors with intron 6 mutation showed reduced expression of FOXP3.

Since WT FOXP3 suppressed the growth of prostate cancer cell lines, a colony growth assay (described in Example 16) was used to determine the effect of mutation. All of the missense mutations abrogated growth inhibition by FOXP3.

The cMYC promoter-luciferase gene vectors (pGL2-CMYC) were constructed by pGL2 vector with DNA fragments in promoter region of CMYC. HEK 293 cells were plated at a density of $5 \times 10^4$ cells per well into 24-well plates and then transiently co-transfected using FuGene 6 (Roche, Indianapolis, Ind.) with pGL2-cMYC luciferase reporter vector (Promega, Madison, Wis.) and pEF1-FOXP3 vector (Invitrogen, Carlsbad, Calif.) (1:2 ratio) according to the protocol of the manufacturer. After transient transfections for 48 h, cells were washed twice with ice-cold PBS and were lysed by 1× Lyses buffer (Promega, Madison, Wis.) for 15 min on shaker. The luciferase activity was performed on a Veritas Microplate Luminometer (Turner BioSystems, Sunnyvale, Calif.) using a Dual Luciferase Assay System (Promega, Madison, Wis.). The experiments were performed at least three times.

Site-Directed Mutagenesis of cMYC Promoter-Luciferase Reporter Plasmid was prepared following the protocols from GeneTailor Site-Directed Mutagenesis System (Invitrogen, Carlsbad, Calif.). The mutagenesis primers are shown in Supplement Table S2. The FOXP3 binding motif sequence (-195 to -189: TGTTTAC (SEQ ID NO: 180)) in the CMYC promoter construct was mutagenized to generate mutated sequence (AAAAGGG (SEQ ID NO: 181)) or the binding motif deletion.

In addition, all of the mutants show 50-95% reduction in their ability to repress MYC promoter. Therefore, the data demonstrated that somatic mutations uncovered from prostate cancer samples caused the FOXP3 protein to be less active.

Example 19

Lineage-Specific Ablation of FoxP3 Expression Resulted in MYC Expression in the Mouse To test the cell-intrinsic effect of FoxP3 deletion, the mice with floxed FoxP3 allele (Fontenot et al., *Immunity* 22: 329-341(2005)) were crossed to a transgenic line that express Cre gene under the probasin promoter (Wu et al., *Nat Genetics* 20: 175-179 (1998)). The previous studies have demonstrated that this promoter causes prostate-specific deletion of Floxed genes, detectable starting in the new born mice.

Using microdissected tissue samples of 14-16 weeks old mice, more than 80% deletion of the FOXP3 locus was observed. Correspondingly, the FOXP3 mRNA was reduced by more than 16-fold. The more profound reduction in mRNA levels likely reflect the fact that our micro-dissected samples also contain non-epithelial cells. Importantly, tissue-specific deletion of FoxP3 lead to more than 4-fold reduction of MYC transcripts. Since the tissues were harvested prior to any sign of hyperplasia, it is likely that deletion of FoxP3 gene directly lead to activation of the MYC locus in mouse prostate epithelial cells. Moreover the fact that MYC up-regulation occurred prior to pathological alteration in the prostate epithelia is consistent with the notion that upregulation of MYC is the primary effect of the FoxP3 gene deletion.

The progression of prostate cancer in the TRAMP model was measured by MRI as described in Eng et al., *Urology* 54: 1112-1119 (1999). Briefly, MRI experiments were performed on a Varian system equipped with a 7.0-Tesla, 18.3-cm horizontal bore magnet (300-MHz proton frequency). For MRI examination, the mice were anesthetized with sodium pentobarbital (70 mg/kg intraperitoneally) and maintained at 37° C. inside the magnet using a heated circulation water blanket, with pelvis motion (due to respiration) minimized by a small plastic support placed before insertion into a 3-cm diameter quadrature birdcage coil (USA Instruments). Multislice images were acquired using a $T_1$-weighted spin echo sequence (TR/TE=880/13, field of view=30×30 mm using a 128×128 matrix, slice thickness=1.5 mm, and slice separation=1.0 to 1.6 mm.). Each set contained 9 to 25 slices and enough sets were obtained to provide contiguous image data of the prostate tumor. Prostate volume was measured using the formula $V=4/3[(D_1+D_2)/4]^3\pi$, where $D_1$ and $D_2$ corresponds to the longest and shortest (transverse and sagittal) diameter measured from the MRI image, respectivly. The accuracy of this measurement was confirmed by comparing prenecropsy MRI volumes to postnecropsy actual prostate volumes in select cases.

16-18 weeks-old mice with prostate-specific deletion of the FoxP3 locus had significant enlargement of the prostate. Histological examination of prostate tissue of WT and cKO 23≈26 weeks old mice indicated extensive hyperplasia in the mutant mice, with a 5-fold higher increase in the % of Ki67+ proloiferating epithelial cells in the mutant mice in compared to the WT. More importantly, the focus of carcinoma was readily identified in all 5 mutant mice examined but not in 6 WT control mice. Many loci showed disruption of basal membrane, which indicated that microinvasion had occurred. In rare cases, vascular invasion was identified in the mutant mice. Therefore, targeted mutation of the FoxP3 gene in the prostate tissue was sufficient to initiate the process of cancer development.

Example 20 p21 is Upregulated after FOXP3 Induction and Contributes to its Tumor Suppressor Activity Although FOXP3 has been shown to repress transcriptional activity of oncogenes, it was hypothesized the FOXP3 could induce the transcription of a tumor suppressor gene. To test this hypothesis, cells of the MCF-7-pBI-FOXP3/GFP cell line were cultured in medium lacking doxycylcine. 24 hours later, cells were collected at 0, 24, 36, 48, 72, and 96 hours. Cells were then measured for FOXP3 expression by realtime-PCR and Western blotting. FOXP3 was induced in the MCF-7-pBI-FOXP3/GFP cell line, but not the MCF-7-pBI-GFP/ control cell line. Importantly, induction of FOXP3 expression by removal of doxycyline from the medium caused a rapid and progressive induction of p21 transcript, as determined by real-time PCR. This induction also was reflected at the protein levels by the Western blots.

Example 21 p21 Contribute to the Tumor Suppressor Activity of FOXP3

In order to determine whether induction of p21 contributes to tumor suppression, MCF-7 cells with inducible expression of either FOXP3 or GFP were supertransfected with either vector control or shP21. After removing untransfected cells by drug selection, the cultures were maintained in doxycycline-free conditions for 10 days. The dead cells were removed and the plates were stained with violet crystal. The colony numbers was counted under a microscope.

p21 shRNA increased the number of colonies in the cell line that expressed FOXP3 by about 20-fold, but barely so for the control cell line expressing GFP only. The sizes of colonies were usually larger in the shRNA group, even for those that expressed GFP only, consistent with the notion that endogenous p21 in the MCF-7 cells limited its growth potential. The partial restoration of the colonies indicated that P21 induction contribute to the tumor suppressor activity of the FOXP3 gene.

Example 22

Inactivation of the FoxP3 Locus Resulted in Increased Skp2 Expression

To determine whether FOXP3 represses Skp2 expression, normal and cancerous mammary tissues were stained with anti-Skp2 and anti-p27 antibodies. As shown in FIG. 1A of Zuo et al., *J Clin Invest* 117: 3765-3773 (2007), Skp2 was found to be highly expressed in cancer cells, but not in normal epithelial cells from the same mouse.

To quantify the increases in Skp2 transcripts, cells were isolated from frozen sections by laser micro-dissection and mRNA were extracted for real-time RT-PCR analysis. The expression of Skp2 in normal mammary epithelial cells from either WT or FoxP3sf/+ mice, as well as mammary cancer tissues from mutant mice, were compared. As shown in FIG. 1B of Zuo et al., *J Clin Invest* 117: 3765-3773 (2007), in comparison to the WT epithelial cells, the heterozygous epithelial cells expressed two-fold higher levels of Skp2, which suggests a FoxP3 gene dose effect on the levels of Skp2. Moreover, in the cancerous tissue that silenced the wild-type allele, expression of Skp2 was substantially enhanced.

A potential caveat of this interpretation is that up-regulation of SKP2 may be due to cancer rather than to the silencing of the FoxP3 locus. Although the WT mice had lower incidences and later onsets of mammary cancer than the heterozygous mice, cancer did arise, both spontaneously and in response to carcinogen treatment. Thus, by comparing mouse mammary cancer tissues from WT and FOXP3sf/+ mice for expression of Skp2, one may be able to discern the contribution of FoxP3 mutation vs. the non-specific effect of cancer growth. As shown in Table 1 of Zuo et al., *J Clin Invest* 117: 3765-3773 (2007), 80% of the spontaneous cancers in the WT mice did not over-express Skp2. In contrast, 71% of the spontaneous tumors from the FoxP3f/+ mice did. A similar trend was observed in the carcinogen induced mammary tumors. Thus, inactivation of the FOXP3 locus is likely responsible for increased Skp2 expression in the mammary tumors.

Example 23

FoxP3 as a Transcriptional Repressor of Skp2

Since FoxP3 is a transcription factor capable of repressing or promoting the expression of a large cohort of genes, whether Skp2 can be a direct target of FoxP3 was evaluated. A mouse mammary cancer line, TSA, was transfected with the V5-targeted FoxP3 protein and generated a polyclonal FOXP3-V5 CL30 and two subclones CL302 and CL305. Using real-time PCR analysis, it was found that the CL302 and 305 have approximately 5-fold higher FoxP3 transcript than the CL30 line. Skp2 transcripts were found to decrease by around 10-20-fold in the FOXP3-V5 transfectant line or clones compared with the vector control. The extent of reduction correlates with the FoxP3 transcript levels. In contrast, no changes in p27 mRNA levels were detected. Since Skp2 regulates the degradation of p27, the levels of these two proteins in FOXP3-V5 transfectants were also examined. As shown in FIG. 2B of Zuo et al., *J Clin Invest* (2007), supra, FoxP3 transfection dramatically reduced Skp2. Correspondingly, p27 was significantly increased in the FOXP3-V5 transfectant. To deter whether the increase of p27 was caused by more rapid degradation, vector or FoxP3-V5-transfected TSA cells were treated with cycloheximide (CHX) and the levels of p27 at 0, 1, 2 and 4 hours after treatment were measured by Western blot. As shown in FIG. 2C of Zuo et al., *J Clin Invest (*2007), supra, p27 was degraded at a much faster rate in the vector transfected TSA cells. Consistent with this notion, reduced ubiquination of p27 in the FoxP3-transfected cells was observed (FIG. 2D of Zuo et al., *J Clin Invest (*2007), supra).

To further confirm that the down-regulation of Skp2 by FOXP3 occurred at the transcription level, the 2.0 kb upstream of the murine Skp2 gene was cloned into the luciferase reporter vector pGL2 and tested the effects of FOXP3 of this promoter's activity by luciferse assay. As shown in FIG. 3A of Zuo et al., *J Clin Invest (*2007), supra, FOXP3 substantially repressed the promoter activity of the Skp2 gene.

Analysis of the Skp2 promoter revealed 4 potential binding sites within the 2 Kb promoter region (FIG. 3B of Zuo et al., *J Clin Invest* (2007), supra). Chromatin immunoprecipitation (ChIP) was carried out to determine whether the FoxP3 binds to the promoter. The nuclear preparations from the FoxP3-transfected cells were fixed with paraformaldehyde. After sonication, the FoxP3-associated genomic DNA was immunoprecipitated and quantitated by real-time PCR. To avoid artifacts associated with differential amplification, the quantity of precipitated DNA was compared to the total input genomic DNA, amplified by the same pairs of primers. In addition, the small amount of DNA precipitated by the IgG control was subtracted. As shown in FIG. 3B of Zuo et al., *J Clin Invest.,* 2007, supra, the primers corresponding to the −0.8 Kb and -1.2 Kb regions yielded significant amounts of product, which is equal to 5-6% of input DNA. In contrast, those corresponding to either the −2.2 or +0.6 Kb region yielded no specific signal.

To determine the significance of the interaction, whether deletion of either binding site disrupts the repression of promoter activity by FoxP3 was tested. As shown in FIG. 3C of Zuo et al., *J Clin Invest.,* 2007, supra, while the WT promoter was repressed by FoxP3, deletion of either site eliminated the repression. Thus, data presented in this section demonstrate that the binding of FoxP3 to specific sites in the Skp2 promoter is essential for FoxP3 repression of Skp2 expression.

Example 24

FoxP3 Expression caused Polyploidy of Breast Cancer Cell Lines

The % of cells with polyploidy can be used as a valuable parameter for Skp2 function. A FoxP3-transfected TSA cell line with moderate levels of the FoxP3-V5 protein was chosen to test the effect of FoxP3 expression (FIG. 4A upper panel of Zuo et al., *J Clin Invest.,* 2007, supra) on the cellular function of Skp2 in order to avoid possible artifacts associated with over-expression. Real-time PCR revealed that the levels of FoxP3 transcripts in the stable transfectants is about 4.5 fold that of the ex vivo mammary epithelial isolates after normalizing against Ck19 transcripts (FIG. 4A, lower panel of Zuo et al., *J Clin Invest.,* 2007, supra). Since not all mammary epithelial cells express FoxP3, the difference between the transfectants and physiological levels of normal cells is likely to be even smaller. As shown in FIG. 4B of Zuo et al., *J Clin Invest.,* 2007, supra, only slightly more than 50% of the transfectants had demonstrable levels of the FoxP3-V5 fusion protein. This allowed for the comparison of the DNA contents of the FoxP3hi and FoxP3lo subsets from the same culture, and of control vector transfectants. As shown in FIG. 4B right panels of Zuo et al., *J Clin Invest.,* 2007, supra, less than 1% of the control vector transfected cells had >4C DNA content, as expected. The same pattern was observed in the FoxP3lo subset from the FoxP3 transfectants. In contrast, about 25% of the FoxP3hi cells had >4C DNA contents.

To determine whether the polyploidy can be attributed to down-regulation of Skp2, the Skp2 cDNA was ectopically expressed in the FoxP3-V5-transfects. As shown in FIG. 4C of Zuo et al., *J Clin Invest.,* 2007, supra, the ectopic expression of Skp2 significantly reduced the % of cells with polyploidy. These data demonstrate that by suppressing Skp2 expression, FoxP3 has a very significant impact on cell cycle progression.

Example 25

FoxP3 and SKP2 Expression in Normal and Malignant Human Breast epithelial Cells

A critical issue is whether FoxP3 expression regulates SKP2 in human breast epithelial cells. To substantiate that inactivation of FOXP3 is a primary event leading to over-expression of SKP2, the early passage of normal human mammary epithelial cells (HMEC) was transduced with lentiviral vector encoding siRNA specific for FOXP3 or control lentiviral vector. The un-transduced cells were eliminated by blasticidin. As shown in FIG. 5A of Zuo et al., *J Clin Invest.,* 2007, supra, the FOXP3 siRNA transduction caused a more than 100-fold reduction in the FOXP3 transcript. Corresponding to this, a 4-fold increase of the SKP2 transcripts was observed (FIG. 5B of Zuo et al., *J Clin Invest.*, 2007, supra). These data demonstrate that in human mammary epithelial cells, FOXP3 is an important regulator for the SKP2 gene.

To identify FOXP3 targets in malignant breast epithelial cells, cell lines with the inducible expression of FOXP3 were produced from MCF-7, a human mammary cancer cell line that does not over-express the HER-2 oncogene, as diagramed in FIG. 6A of Zuo et al., *J Clin Invest.*, 2007, supra. The expression of SKP2 was analyzed at different time points after the cells were cultured in the absence of deoxycyclin, which induced the expression of FOXP3. The levels of SKP2 were quantitated by real-time PCR and were compared with control cell lines expressing GFP but not FOXP3 under the same conditions. The relative levels of the SKP2 transcripts of the control cell lines and the FOXP3 expressing cells at different times are presented in FIG. 6B of Zuo et al., *J Clin Invest.*, 2007, supra. Using the levels of un-induced cells as references, nearly a 4-fold reduction of SKP2 mRNA was observed within 24 hours of removing deoxycyclin in the FOXP3-transfectants. By 48 hours more than an 8-fold reduction was observed. No reduction of SKP2 transcript was observed in control cell lines cultured under the same condition. These data demonstrate a rapid repression of the SKP2 transcripts following FOXP3 induction.

It is shown herein that the FOXP3 locus is frequently inactivated in the majority of, although not all, mammary cancer tissues in humans. On the other hand, SKP2 is over expressed in nearly 50% of the breast cancer samples. If a loss of FOXP3 contributes to SKP2 expression, one may expect an increased rate of the SKP2+ samples among the FOXP3– tumors. To address this issue, 206 cases of breast cancer samples in tissue microarray were independently stained and double blindly scored for their expression of SKP2 and FOXP3. As shown in FIG. 7 of Zuo et al., *J Clin Invest* (2007), supra, among the FOXP3+ samples, less than 30% of the cells expressed SKP2. In contrast, more than 56% of the FOXP3– samples showed SKP2 over-expression. Statistical analysis revealed that the difference is highly significant (P=0.0016).

Example 26

The Ectopic Expression of SKP2 Bypass FOXP3-Mediated Growth inhibition for a HER-2lo Breast Cancer Cell Line As demonstrated herein, FOXP3 can suppress the growth of both ErbB2hi and ErbB2lo tumor cell lines. While the repression of ErbB2hi tumor cell line TSA can be rescued by the ectopic expression of ErbB2, the target responsible for growth inhibition of the ErbB2lo tumor cells remained to be identified. To determine the relevance of SKP2 repression in growth inhibition by FOXP3, either vector or SKP2 was ectopically expressed in the MCF7 cell line with tet-off inducible expression of FOXP3. The impact of the SKP2 expression was visualized by colony formation following tet-off induction of FOXP3. As shown in FIG. 8 of Zuo et al., *J Clin Invest* (2007), supra, in the vector transfected group, Tet-off induction of FOXP3 wiped out all MCF7 colonies, as expected. Remarkably, ectopic expression of SKP2 resulted in almost complete restoration of the colonies (FIG. 8A of Zuo et al., *J Clin Invest* (2007), supra), although the colony size is still somewhat less than the culture without FOXP3 induction (FIG. 8B of Zuo et al., *J Clin Invest* (2007), supra). These results demonstrate a critical role of SKP2 down-regulation in the ErbB2lo breast cancer cell line.

The foregoing description is given for clearness of understanding only, and no unnecessary limitations should be understood therefrom, as modifications within the scope of the invention may be apparent to those having ordinary skill in the art.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of reducing tumor growth, said tumor comprising a breast cancer cell, a prostate cancer cell, or a thymic epithelial cancer cell, which cancer cell is sensitive to FOXP3 tumor suppressor activity in a subject, comprising administering directly to the cancer cell a recombinant expression vector comprising (i) a nucleic acid encoding a FOXP3 protein and (ii) a promoter sequence active in the cancer cell, wherein the promoter sequence is operably linked to said nucleic acid, wherein expression of said nucleic acid is in an amount effective to reduce tumor growth in the subject.

2. The method of claim 1, wherein the nucleic acid encodes a FOXP3 protein comprising the amino acid sequence of any of SEQ ID NOs: 20 to 26 and 28 to 36.

3. The method of claim 1, wherein the nucleic acid comprises the nucleotide sequence of any of SEQ ID NOs: 1 to 7 and 9 to 17.

4. The method of claim 1, wherein the subject is a mammal.

5. The method of claim 4, wherein the mammal is a human.

6. The method of claim 1, wherein the method effectively reduces metastasis of the cancer cell.

7. The method of claim 1, wherein the method further effectively increases survival of the subject.

8. The method of claim 1, wherein the method effectively increases apoptosis of the cancer cell.

9. The method of claim 1, wherein the method effectively increases killing of the cancer cell in said tumor.

* * * * *

UNITED STATES PATENT AND TRADEMARK OFFICE
CERTIFICATE OF CORRECTION

PATENT NO. : 8,158,596 B2  
APPLICATION NO. : 12/119158  
DATED : April 17, 2012  
INVENTOR(S) : Yang Liu et al.

Page 1 of 1

It is certified that error appears in the above-identified patent and that said Letters Patent is hereby corrected as shown below:

On the Title Page:

At Item (73) –

"The Regents of the University of Michigan, Ann Arbor, MI (US)" should be –

"The Regents of the University of Michigan, Ann Arbor, MI (US)"; "The Ohio State University Research Foundation, Columbus, OH (US)"

Signed and Sealed this  
Ninth Day of October, 2012

David J. Kappos  
*Director of the United States Patent and Trademark Office*

SEQUENCE LISTING

<160> NUMBER OF SEQ ID NOS: 181

<210> SEQ ID NO 1
<211> LENGTH: 2397
<212> TYPE: DNA
<213> ORGANISM: Homo sapiens

<400> SEQUENCE: 1

```
gcacacactc atcgaaaaaa atttggatta ttagaagaga gaggtctgcg gcttccacac      60
cgtacagcgt ggttttttctt ctcggtataa aagcaaagtt gttttttgata cgtgacagtt    120
tcccacaagc caggctgatc cttttctgtc agtccacttc accaagcctg cccttggaca     180
aggacccgat gcccaacccc aggcctggca agccctcggc cccttccttg gcccttggcc     240
catccccagg agcctcgccc agctggaggg ctgcacccaa agcctcagac ctgctggggg     300
cccggggccc aggggggaacc ttccagggcc gagatcttcg aggcggggcc catgcctcct    360
cttcttcctt gaaccccatg ccaccatcgc agctgcagct gcccacactg cccctagtca    420
tggtggcacc ctccggggca cggctgggcc ccttgcccca cttacaggca ctcctccagg    480
acaggccaca tttcatgcac cagctctcaa cggtggatgc ccacgcccgg accctgtgc     540
tgcaggtgca cccctggag agcccagcca tgatcagcct cacaccaccc accaccgcca    600
ctggggtctt ctccctcaag gcccggcctg gcctccacc tgggatcaac gtggccagcc    660
tggaatgggt gtccagggag ccggcactgc tctgcacctt cccaaatccc agtgcaccca    720
ggaaggacag caccctttcg gctgtgcccc agagctccta cccactgctg gcaaatggtg    780
tctgcaagtg gcccggatgt gagaaggtct tcgaagagcc agaggacttc ctcaagcact    840
gccaggcgga ccatcttctg gatgagaagg gcagggcaca atgtctcctc cagagagaga    900
tggtacagtc tctggagcag cagctggtgc tggagaagga gaagctgagt gccatgcagg    960
cccacctggc tgggaaaatg gcactgacca aggcttcatc tgtggcatca tccgacaagg   1020
gctcctgctg catcgtagct gctggcagcc aaggccctgt cgtcccagcc tggtctggcc   1080
cccgggaggc ccctgacagc ctgtttgctg tccggaggca cctgtggggt agccatggaa   1140
acagcacatt cccagagttc ctccacaaca tggactactt caagttccac aacatgcgac   1200
cccctttcac ctacgccacg ctcatccgct gggccatcct ggaggctcca gagaagcagc   1260
ggacactcaa tgagatctac cactggttca cacgcatgtt tgccttcttc agaaaccatc   1320
ctgccacctg gaagaacgcc atccgccaca acctgagtct gcacaagtgc tttgtgcggg   1380
tggagagcga gaagggggct gtgtggaccg tggatgagct ggagttccgc aagaaacgga   1440
gccagaggcc cagcaggtgt tccaacccta cacctggccc ctgacctcaa gatcaaggaa   1500
aggaggatgg acgaacaggg gccaaactgg tgggaggcag aggtggtggg ggcagggatg   1560
ataggccctg gatgtgccca cagggaccaa gaagtgaggt ttccactgtc ttgcctgcca   1620
gggcccctgt tcccccgctg gcagccaccc cctcccccat catatccttt gccccaaggc   1680
tgctcagagg ggccccggtc ctggcccag ccccacctc cgcccagac acacccccca   1740
gtcgagccct gcagccaaac agagccttca caaccagcca cacagagcct gcctcagctg   1800
ctcgcacaga ttacttcagg gctggaaaag tcacacagac acacaaaatg tcacaatcct   1860
gtccctcact caacacaaac cccaaaacac agagagcctg cctcagtaca ctcaaacaac   1920
ctcaaagctg catcatcaca caatcacaca caagcacagc cctgacaacc cacacacccc   1980
aaggcacgca cccacagcca gcctcagggc cacaggggc actgtcaaca caggggtgtg    2040
cccagaggcc tacacagaag cagcgtcagt accctcagga tctgaggtcc caacacgtgc   2100
tcgctcacac acacggcctg ttagaattca cctgtgtatc tcacgcatat gcacacgcac   2160
agccccccag tgggtctctt gagtcccgtg cagacacaca cagccacaca cactgccttg   2220
ccaaaaatac cccgtgtctc ccctgccact cacctcactc ccattccctg agccctgatc   2280
```

| | |
|---|---|
| catgcctcag cttagactgc agaggaacta ctcatttatt tgggatccaa ggcccccaac | 2340 |
| ccacagtacc gtccccaata aactgcagcc gagctcccca caaaaaaaaa aaaaaaa | 2397 |

<210> SEQ ID NO 2
<211> LENGTH: 3739
<212> TYPE: DNA
<213> ORGANISM: Mus musculus

<400> SEQUENCE: 2

| | |
|---|---|
| gctgatcccc ctctagcagt ccacttcacc aaggtgagcg agtgtccctg ctctccccca | 60 |
| ccagacacag ctctgctggc gaaagtggca gagaggtatt gagggtgggt gtcaggagcc | 120 |
| caccagtaca gctggaaaca cccagccact ccagctcccg gcaacttctc ctgactctgc | 180 |
| cttcagacga gacttggaag acagtcacat ctcagcagct cctctgccgt tatccagcct | 240 |
| gcctctgaca agaacccaat gcccaaccct aggccagcca agcctatggc tccttccttg | 300 |
| gcccttggcc catccccagg agtcttgcca agctggaaga ctgcacccaa gggctcagaa | 360 |
| cttctaggga ccaggggctc tgggggaccc ttccaaggtc gggacctgcg aagtggggcc | 420 |
| cacacctctt cttccttgaa cccctgcca ccatcccagc tgcagctgcc tacagtgccc | 480 |
| ctagtcatgg tggcaccgtc tggggcccga ctaggtccct caccccacct acaggccctt | 540 |
| ctccaggaca gaccacactt catgcatcag ctctccactg tggatgccca tgcccagacc | 600 |
| cctgtgctcc aagtgcgtcc actggacaac ccagccatga tcagcctccc accaccttct | 660 |
| gctgccactg gggtcttctc cctcaaggcc cggcctggcc tgccacctgg gatcaatgtg | 720 |
| gccagtctgg aatgggtgtc cagggagcca gctctactct gcaccttccc acgctcgggt | 780 |
| acacccagga aagacagcaa ccttttggct gcaccccaag gatcctaccc actgctggca | 840 |
| aatggagtct gcaagtggcc tggttgtgag aaggtcttcg aggagccaga agagtttctc | 900 |
| aagcactgcc aagcagatca tctcctggat gagaaaggca aggcccagtg cctcctccag | 960 |
| agagaagtgg tgcagtctct ggagcagcag ctggagctgg aaaaggagaa gctgggagct | 1020 |
| atgcaggccc acctggctgg gaagatggcg ctggccaagg ctccatctgt ggcctcaatg | 1080 |
| gacaagagct cttgctgcat cgtagccacc agtactcagg gcagtgtgct cccggcctgg | 1140 |
| tctgctcctc gggaggctcc agacggcggc ctgtttgcag tgcggaggca cctctgggga | 1200 |
| agccatggca atagttcctt cccagagttc ttccacaaca tggactactt caagtaccac | 1260 |
| aatatgcgac cccctttcac ctatgccacc cttatccgat gggccatcct ggaagccccg | 1320 |
| gagaggcaga ggacactcaa tgaaatctac cattggttta ctcgcatgtt cgcctacttc | 1380 |
| agaaaccacc ccgccacctg gaagaatgcc atccgccaca acctgagcct gcacaagtgc | 1440 |
| tttgtgcgag tggagagcga aaggagca gtgtggaccg tagatgaatt tgagtttcgc | 1500 |
| aagaagagga gccaacgccc caacaagtgc tccaatccct gcccttgacc tcaaaaccaa | 1560 |
| gaaaaggtgg gcgggggagg gggccaaaac catgagactg aggctgtggg ggcaaggagg | 1620 |
| caagtcctac gtgtacctat ggaaaccggg cgatgatgtg cctgctatca gggcctctgc | 1680 |
| tccctatcta gctgccctcc tagatcatat catctgcctt acagctgaga ggggtgccaa | 1740 |
| tcccagccta gcccctagtt ccaacctagc cccaagatga actttccagt caaagagccc | 1800 |
| tcacaaccag ctatacatat ctgccttggc cactgccaag cagaaagatg acagacacca | 1860 |
| tcctaatatt tactcaaccc aaaccctaaa acatgaagag cctgccttgg tacattcgtg | 1920 |
| aactttcaaa gttagtcatg cagtcacaca tgactgcagt cctactgact cacacccaa | 1980 |
| agcactcacc cacaacatct ggaaccacgg gcactatcac acataggtgt atatacagac | 2040 |

```
ccttacacag caacagcact ggaaccttca caattacatc cccccaaacc acacaggcat    2100
aactgatcat acgcagcctc aagcaatgcc caaaatacaa gtcagacaca gcttgtcaga    2160
acacgctcgt gtgcacgtac acacatgcag cccctccact ctatctcctg agttccatga    2220
atacacaccg actctccaag atgtacccca cgtctcactt gccactgacc ccagttccct    2280
acccacaagc cccaatccat gcctaagcgt ggcccacaga agaacttctc ttttatttgg    2340
gatccaaggc ccctggcccc cagtgcccat ccaataaact gtggtcagct ggacaatcac    2400
cctgatcaga tatgggaaca tataagcaga cagctgggtt taagatccca gcaggagaaa    2460
gcggatacca aatgaaagag agtgctagaa caggtgcctc agcactgtct ccagcacccc    2520
aaattcctgc ctgtggttag gagacatcca tcagggctct aggcctctcg acccggccc    2580 aagaggccag cattctcctg gcgaagggct cggtagtcct cacagatctt ctccaggttg    2640
ctcaaagtct tcttgcccat ctctgtctca atctaagaaa acaggatgca cacttcttca    2700
gcccctgcag gctgcccctc tactgaactc ctccctgctc ctcctattcc cgtaacagca    2760
gcctgttcct tcccatcact gggcttctgg gtatgtcctt ccctccactc cacctaaagc    2820
agcaacttct gccatgggct ctgggaggca ttaggagccg caagctaaaa gccagggctc    2880
agagtaggct actggctagc ttcaggtccc aggcacagtg ggcacgaagg caaagcctct    2940
agctgttagt tgtctggttt caaagactct cagcgcaaaa caaggaacta tcccctggcc    3000
tgtctccatt ccccttacca gtcccaggtc tcacctgctc ctcaagatct cgaacttccc    3060
tcatgatagt gcctgtgtcc tcaatggtct ggatgagctg actgcaattc tggagacagc    3120
aagaatacaa ggcttgcacc tatgctggcc ctctccagcc aacccaccag gcacatggct    3180
cccctcacct catgcagggc agctaggtac ttgtaggctt tccgaacagc atcatccttc    3240
ttagcatcct gataagacaa aggggatctc cgagatatca gcaagccatt ccccttttc    3300 cactactcta tgcccctata agaccaccct ttactagtac tttgccttca tcctccacag    3360
agcaaagcta ggcccaagc aacagtgcac ctaaaggact cacagagggg caggcaacaa    3420
ctcagtcccg cctccaccct cccggaggcc agcctgctcc ataccttgaa cacaagctca    3480
tcagtcactg caaatgtccg gtcgagcttc ccagagagag agttgatttc cttctgcagt    3540
tcctttgtgt ccgacaagat ctggtagaaa ccagggtaac tatcagtgca catcttgggc    3600
aaggtagctg atcagtgata acactcacgt gcctatactt acatccagtc agggcccatg    3660
tcgctgtgtt ggggtgacta ttatgtgttg gagtgtgcct gaacagctct gcctagtagt    3720
gagcataaag tccctgtgt                                                 3739

<210> SEQ ID NO 3
<211> LENGTH: 1431
<212> TYPE: DNA
<213> ORGANISM: Felis catus

<400> SEQUENCE: 3 tcagggtcc gagcgtgggt atcgactgga gcacgtggac actgacatgg actgaaggag      60
tagaaaagtt tccacaagc ctggctgatc ctttctgtg agtccacttc aagaagcctg      120
ccctcggacg aggacccaat gcccaacccc aggccagcca agccctcggc cccttccttg     180
gcacttggcc catccccagg agcctcaccc agctggaggg ctggacccaa gacttcagac     240
ccgctggggg ccaagggccc aggggcaacc ttccagggcc gggacctccg aggcgggacc     300
catgcctcct cctctttgaa ccccatgcca ccatcacagc tgcagctgcc tacagtgccc     360
ctagtcatgg tggcaccctc tgggacacgg ctgggcccct cgccccactt gcaggcactc     420
```

| | |
|---|---|
| ctccaggaca ggccacactt catgcaccag ctctcaacgg tggataccca cgctcggacc | 480 |
| cctgtgctgc aggtgcgccc actggacagc ccagctatga tcagcctccc accacccact | 540 |
| gctgccactg gtgtcttctc cctcaaggcc cggcccggcc tgccacctgg aatcaacgtg | 600 |
| gccagcctga atgggtgtc cagggagcca gcactgctct gcaccttccc aagcccagc | 660 |
| acaccccgga agacagcac cctttcaacc gygccccagg gctcctattc actgctggca | 720 |
| aatggtgtct gcaagtggcc tggatgtgag aaggtcttcg aggagccaga ggatttcctc | 780 |
| aagcactgcc aggcggacca tctcctggat gagaagggca gggcacagtg tctcctccag | 840 |
| agggaagtgg tgcagtcttt ggaacagcag ctggtgctgg agaaggagaa gctgggtgct | 900 |
| atgcaggccc acctagctgg aagatggct ctgaccaaag ctccatccac ggcgtcatcc | 960 |
| gacaagggct cctgctgcat cgtggccact ggcaccccag ccgccactgg cccagcctgg | 1020 |
| cccagccccc aggaggcccc tgacggcctg tttgctgtgc ggaggcacct ctggggcagc | 1080 |
| catgaaaata gcacattccc agagttcttc cacaacatgg attacttcaa gttccacgac | 1140 |
| atgcggccac ccttcaccta cgccaccctc atccgctggg ccatcctgga ggctcctgag | 1200 |
| aagcagcgga ccctcaacga gatctaccac tggttcacac gcatgtttgc cttcttcaga | 1260 |
| aaccaccccg ccacctggaa gaatgccatc cgccacaacc tgagcctaca caaatgcttt | 1320 |
| gtgcgggtgg agagtgagaa gggggccgtg tggaccgtgg atgaattcga gttccgcaag | 1380 |
| aagaggagcc agaggcccag caggtgttcc aaccccacac ctggccccta a | 1431 |

<210> SEQ ID NO 4
<211> LENGTH: 3819
<212> TYPE: DNA
<213> ORGANISM: Mus musculus

<400> SEQUENCE: 4

| | |
|---|---|
| agtttcccac aagccaggct gatccccctc tagcagtcca cttcaccaag gtgagcgagt | 60 |
| gtccctgctc tccccacca gacacagctc tgctggcgaa agtggcagag aggtattgag | 120 |
| ggtgggtgtc aggagcccac cagtacagct ggaaacaccc agccactcca gacagaagaa | 180 |
| agcttagaga agacagaccc atgctgtggc cctgagctct gcagtactga attcagctct | 240 |
| cccggcaact tctcctgact ctgccttcag acgagacttg gaagacagtc acatctcagc | 300 |
| agctcctctg ccgttatcca gcctgcctct gacaagaacc caatgcccaa ccctaggcca | 360 |
| gccaagccta tggctccttc cttggccctt ggcccatccc caggagtctt gccaagctgg | 420 |
| aagactgcac ccaagggctc agaacttcta gggaccaggg gctctggggg acccttccaa | 480 |
| ggtcgggacc tgcgaagtgg ggcccacacc tcttcttcct tgaaccccct gccaccatcc | 540 |
| cagctgcagc tgcctacagt gccccctagtc atggtggcac cgtctgggc ccgactaggt | 600 |
| ccctcacccc acctacaggc ccttctccag gacagaccac acttcatgca tcagctctcc | 660 |
| actgtggatg cccatgccca gacccctgtg ctccaagtgc gtccactgga cacccagcc | 720 |
| atgatcagcc tcccaccacc ttctgctgcc actggggtct tctccctcaa ggcccggcct | 780 |
| ggcctgccac ctgggatcaa tgtggccagt ctggaatggg tgtccaggga ccagctcta | 840 |
| ctctgcacct tcccacgctc gggtacaccc aggaaagaca gcaacctttt ggctgcaccc | 900 |
| caaggatcct acccactgct ggcaaatgga gtctgcaagt ggcctggttg tgagaaggtc | 960 |
| ttcgaggagc cagaagagtt tctcaagcac tgccaagcag atcatctcct ggatgagaaa | 1020 |
| ggcaaggccc agtgcctcct ccagagagaa gtggtgcagt ctctggagca gcagctggag | 1080 |
| ctggaaaagg agaagctggg agctatgcag gcccacctgg ctgggaagat ggcgctggcc | 1140 |

```
aaggctccat ctgtggcctc aatggacaag agctcttgct gcatcgtagc caccagtact   1200
cagggcagtg tgctcccggc ctggtctgct cctcgggagg ctccagacgg cggcctgttt   1260
gcagtgcgga ggcacctctg gggaagccat ggcaatagtt ccttcccaga gttcttccac   1320
aacatggact acttcaagta ccacaatatg cgaccccctt tcacctatgc cacccttatc   1380
cgatgggcca tcctggaagc cccggagagg cagaggacac tcaatgaaat ctaccattgg   1440
tttactcgca tgttcgccta cttcagaaac caccccgcca cctggaagaa tgccatccgc   1500
cacaacctga gcctgcacaa gtgctttgtg cgagtggaga gcgagaaggg agcagtgtgg   1560
accgtagatg aatttgagtt tcgcaagaag aggagccaac gccccaacaa gtgctccaat   1620
ccctgccctt gacctcaaaa ccaagaaaag gtgggcgggg gaggggccca aaaccatgag   1680
actgaggctg tggggcaag gaggcaagtc ctacgtgtac ctatggaaac cgggcgatga   1740
tgtgcctgct atcagggcct ctgctcccta tctagctgcc ctcctagatc atatcatctg   1800
ccttacagct gagaggggtg ccaatcccag cctagcccct agttccaacc tagccccaag   1860
atgaactttc cagtcaaaga gccctcacaa ccagctatac atatctgcct tggccactgc   1920
caagcagaaa gatgacagac accatcctaa tatttactca acccaaaccc taaaacatga   1980
agagcctgcc ttggtacatt cgtgaacttt caaagttagt catgcagtca cacatgactg   2040
cagtcctact gactcacacc ccaaagcact cacccacaac atctggaacc acgggcacta   2100
tcacacatag gtgtatatac agaccettac acagcaacag cactggaacc ttcacaatta   2160
catcccccca aaccacacag gcataactga tcatacgcag cctcaagcaa tgcccaaaat   2220
acaagtcaga cacagcttgt cagaacacgc tcgtgtgcac gtacacacat gcagcccctc   2280
cactctatct cctgagttcc atgaatacac accgactctc caagatgtac cccacgtctc   2340
acttgccact gaccccagtt ccctacccac aagccccaat ccatgcctaa gcgtggccca   2400
cagaagaact tctctttat ttgggatcca aggcccctgg cccccagtgc ccatccaata   2460
aactgtggtc agctggacaa tcaccctgat cagatatggg aacatataag cagacagctg   2520
ggtttaagat cccagcagga gaaagcggat accaaatgaa agagagtgct agaacaggtg   2580
cctcagcact gtctccagca ccccaaattc ctgcctgtgg ttaggagaca tccatcaggg   2640
ctctaggcct ctcggacccg gcccaagagg ccagcattct cctggcgaag ggctcggtag   2700
tcctcacaga tcttctccag gttgctcaaa gtcttcttgc ccatctctgt ctcaatctaa   2760
gaaaacagga tgcacacttc ttcagcccct gcaggctgcc cctctactga actcctccct   2820
gctcctccta ttcccgtaac agcagcctgt tccttcccat cactgggctt ctgggtatgt   2880
ccttccctcc actccaccta aagcagcaac ttctgccatg ggctctggga ggcattagga   2940
gccgcaagct aaaagccagg gctcagagta ggctactggc tagcttcagg tcccaggcac   3000
agtgggcacg aaggcaaagc ctctagctgt tagttgtctg gtttcaaaga ctctcagcgc   3060
aaaacaagga actatcccct ggcctgtctc cattcccctt accagtccca ggtctcacct   3120
gctcctcaag atctcgaact tccctcatga tagtgcctgt gtcctcaatg gtctggatga   3180
gctgactgca attctggaga cagcaagaat acaaggcttg cacctatgct ggccctctcc   3240
agccaaccca ccaggcacat ggctcccctc acctcatgca gggcagctag gtacttgtag   3300
gctttccgaa cagcatcatc cttcttagca tcctgataag acaaagggga tctccgagat   3360
atcagcaagc cattcccct tttccactac tctatgcccc tataagacca ccctttacta   3420
gtactttgcc ttcatcctcc acagagcaaa gctaggcccc caagcaacag tgcacctaaa   3480
ggactcacag aggggcaggc aacaactcag tcccgcctcc accctcccgg aggccagcct   3540
```

| | |
|---|---|
| gctccatacc ttgaacacaa gctcatcagt cactgcaaat gtccggtcga gcttcccaga | 3600 |
| gagagagttg atttccttct gcagttcctt tgtgtccgac aagatctggt agaaaccagg | 3660 |
| gtaactatca gtgcacatct tgggcaaggt agctgatcag tgataacact cacgtgccta | 3720 |
| tacttacatc cagtcagggc ccatgtcgct gtgtttgggt gactattatg tgttggagtg | 3780 |
| tgcctgaaca gctctgccta gtagtgagca taaagtccc | 3819 |

<210> SEQ ID NO 5
<211> LENGTH: 1399
<212> TYPE: DNA
<213> ORGANISM: Bos taurus

<400> SEQUENCE: 5

| | |
|---|---|
| atgcccaacc caaggccagc caagcccttg gccccttcct tggtactcag cccatcccca | 60 |
| ggagcctcgc ccagctggag ggctgcaccc aaggcctcag accagctggg caccaagagc | 120 |
| ccagggacaa ctttccaagg ccgggatctc cgaagcgggg cccacacttc ctcttcctcc | 180 |
| ttgaacccca tgccaccatc acagctgcag atgcccacag taccccttgt catggtggca | 240 |
| ccctccggag ctcggctggg tccctcaccc cacttgcagg cgctcctcca ggacaggcca | 300 |
| cacttcgtgc accagctctc aacggtggac gcccatgccc ggacccctgt gctgcaggtg | 360 |
| cgcccactgg acagcccagc tatgatcagc tcccgccac ccactgctgc tacgggctc | 420 |
| ttctctctca aggcccggcc cggcctgcca cctggaatca acgtggccag cctggagtgg | 480 |
| gtttccaggg agccagcact gctctgcacc ttcccaagcc ccggcatgcc taggaaagac | 540 |
| agcacccttt cgactgtgcc ccagggctcc tactcactgc tagcaaatgg cgtctgcaag | 600 |
| tggcccggat gtgagaaggt cttcaaggag ccagaagact tcctcaagca ctgccaggca | 660 |
| gaccatctcc tggatgagaa gggcagggcg cagtgtctgc tccagaggga ggtggtgcaa | 720 |
| tctctggagc aacagctggt gctggagaag gagaagctgg gtgctatgca ggcccatctg | 780 |
| gccgggaaga tggcccaaac caaggctcca tctgcggcat catctgacaa gggctcctgc | 840 |
| tgtatcgtag ccactggcac cccaggcacc accgtcccag cctggccagg accccaggag | 900 |
| gcccccgatg gcctgtttgc tgtgcggagg cacctctggg gcagccatgg aaacagcaca | 960 |
| ttcccagagt tcttccacaa catggactac ttcaagttcc acaacatgcg gccccctttc | 1020 |
| acctatgcca ccctcatccg ctgggccatc ctggaggctc tgagaagca gcggacactc | 1080 |
| aacgagatct atcactggtt tacacgcatg tttgccttct tcagaaacca cccagccacc | 1140 |
| tggaagaatg ccatccgcca caacctgagc ctgcacaagt gcttcgtacg cgtggagagc | 1200 |
| gagaaggggg ttgtgtggac cgtggatgag tttgagttcc gcaagaagag gagccagagg | 1260 |
| cccagcaggt gttccaaccc cacacctggc ccctgatctc agagccaaga agaagggga | 1320 |
| ggacagggga ggggatcgaa gtggctgggg gcaggggtga ccagccctgg acatgcccgc | 1380 |
| agggaccaag aagtaaggt | 1399 |

<210> SEQ ID NO 6
<211> LENGTH: 1296
<212> TYPE: DNA
<213> ORGANISM: Macaca mulatta

<400> SEQUENCE: 6

| | |
|---|---|
| atgcccaacc caggccaggg caagccctcg gccccttcct tggcccttgg cccatcccca | 60 |
| ggagcctcgc ccagctggag ggctgcgccc aaagcctcag acctgctggg ggccggggc | 120 |
| cctgggggaa tcttccaggg ccgagatctt cgaggcgggg ctcatgcctc ttcttcctcc | 180 |

```
ttgaacccta tgccaccatc gcagctgcag ctgcccacac tgcccctagt catggtggca      240
ccctccgggg cacggctggg ccccttgccc cacttacagg cactcctcca ggacaggcca      300
catttcatgc accagctctc aacggtggat gcccacgccc ggaccccgtgt gctgcaggtg     360 cacccccctgg agagcccagc catgatcagc ctcccaccac ccaccactgc cactggggtc     420
ttctccctca aggcccggcc tggcctccca cctgggatca acgtggccag cccggaatgg      480
gtgtccaggg agctagcact gctctgcacc ttcccaaatc ctggtgcacc caggaaggac      540
agcacccttt cggccatgcc ccagagctcc tacccactgc tggcaaatgg tgtctgcaag      600
tggcccggat gtgagaaagt cttcgaagag ccagaggact tcctcaagca ctgccaagca      660
gaccatcttc tggatgagaa gggcagggca caatgtctcc tccagagaga gatggtacag      720
tctctgaagc agcagctggt gctggagaag gagaagctga gtgctatgca ggcccacctg      780
gctgggaaaa tggcactgac caaggcttca tctgtggcat catctgacaa gggctcctgc      840
tgcattgtag ctgctggcag tcaaggcagt gccgtcccag cctggtctgg cccccgggag      900
gcccctgaca gcctgtttgc tgtgcggagg cacctgtggg gtagccatgg aaacagcaca      960
ttcccagagt tccttcacaa catggactac ttcaagttcc acaatatgcg accccctttc     1020
acctatgcca cgctcatccg ctgggccatc ctggaggctc cagagaagca gcggacactc     1080
aatgagatct accactggtt cacacgcatg ttcgccttct tcagaaacca tcctgccacc     1140
tggaagaacg ccatccgcca caacctgagc ctgcacaagt gctttgtgcg ggtggagagc     1200
gagaaggggg ctgtgtggac cgtggatgag ttggagttcc gcaagaaacg gagccagagg     1260
ccaagcaggt gttccaaccc tacacctggc ccctga                                1296

<210> SEQ ID NO 7
<211> LENGTH: 1399
<212> TYPE: DNA
<213> ORGANISM: Bos taurus

<400> SEQUENCE: 7
atgcccaacc caaggccagc caagcccttg gccccttcct tggtactcag cccatcccca       60
ggagcctcgc ccagctggag ggctgcaccc aaggcctcag accagctggg caccaagagc      120
ccagggacaa cttccaagg ccgggatctc cgaagcgggg cccacacttc ctcttcctcc       180
ttgaacccca tgccaccatc acagctgcag atgcccacag taccccttgt catggtggca     240
ccctccggag ctcggctggg tccctcaccc cacttgcagg cgctcctcca ggacaggcca      300
cacttcgtgc accagctctc aacggtggac gcccatgccc ggaccccgtgt gctgcaggtg     360 cgcccactgg acagcccagc tatgatcagc ctcccgccac ccactgctgc tacggggctc      420
ttctctctca aggcccggcc cggcctgcca cctggaatca acgtggccag cctggagtgg      480
gtttccaggg agccagcact gctctgcacc ttcccaagcc ccggcatgcc taggaaagac      540
agcacccttt cgactgtgcc ccaggctccc tactcactgc tagcaaatgg cgtctgcaag      600
tggcccggat gtgagaaggt cttcaaggag ccagaagact tcctcaagca ctgccaggca      660
gaccatctcc tggatgagaa gggcagggcg cagtgtctgc tccagaggga ggtggtgcaa      720
tctctggagc aacagctggt gctggagaag gagaagctgg gtgctatgca ggcccatctg      780
gccgggaaga tggcccaaac caaggctcca tctgcggcat catctgacaa gggctcctgc      840
tgtatcgtag ccactggcac cccaggcacc accgtcccag cctggccagg accccaggag      900
gcccccgatg gcctgtttgc tgtgcggagg cacctctggg gcagccatgg aaacagcaca      960
ttcccagagt tcttccacaa catggactac ttcaagttcc acaacatgcg gccccctttc     1020
```

| | |
|---|---|
| acctatgcca ccctcatccg ctgggccatc ctggaggctc ctgagaagca gcggacactc | 1080 |
| aacgagatct atcactggtt tacacgcatg tttgccttct tcagaaacca cccagccacc | 1140 |
| tggaagaatg ccatccgcca caacctgagc ctgcacaagt gcttcgtacg cgtggagagc | 1200 |
| gagaagggg ttgtgtggac cgtggatgag tttgagttcc gcaagaagag gagccagagg | 1260 |
| cccagcaggt gttccaaccc cacacctggc ccctgatctc agagccaaga agagaaggga | 1320 |
| ggacagggga ggggatcgaa gtggctgggg cagggtga ccagccctgg acatgcccgc | 1380 |
| agggaccaag aagtaaggt | 1399 |

<210> SEQ ID NO 8
<211> LENGTH: 546
<212> TYPE: DNA
<213> ORGANISM: Pan troglodytes

<400> SEQUENCE: 8

| | |
|---|---|
| tgtcagtcca cttcaccaag cctgcccttg acaaggacc cgatgcccaa ccccaggcct | 60 |
| ggcaagccct cggccccttc cttggcccctt ggcccatccc caggagcctc gcccagctgg | 120 |
| agggctgcac ccaaagcctc agacctgctg ggggcccggg gcccagggg aaccttccag | 180 |
| ggccgagatc ttcgaggcgg ggcccatgcc tcctcttcct ccttgaaccc catgccacca | 240 |
| tcgcagctgc aggtgcaccc cctggagagc ccagccatga tcagcctccc accacccacc | 300 |
| accgccactg gggtcttctc cctcaaggcc cggcctggcc tcccacctgg atcaacgtg | 360 |
| gccagcctgg aatgggtgtc cagggagccg gcactgctct gcaccttccc aaatcccggt | 420 |
| gcacccagga aggacagcac cctttcggct gtgccccaga gctcctaccc actgctggca | 480 |
| aatggtgtct gcaagtggcc tggatgtgag aaggtcttcg aagagccaga ggacttcctc | 540 |
| aagtga | 546 |

<210> SEQ ID NO 9
<211> LENGTH: 625
<212> TYPE: DNA
<213> ORGANISM: Peromyscus maniculatus

<400> SEQUENCE: 9

| | |
|---|---|
| tacccactgc tggcaaatgg agtctgcaag tggcctggtt gcgagaaggt cttcgaggag | 60 |
| ccagaagagt ttcttaagca ttgccaagca gatcacctcc tggatgagaa gggcaaagcg | 120 |
| cagtgcctcc tgcagcagcg agaagtggtc cagtctctgg aacagcagct ggagctggaa | 180 |
| aaggagaagc tgggtgctat gcaggcccac ctggccggga gatggcact gtcaaaggct | 240 |
| ccagctatgg cctcggtgga caagagctcc tgctgcattg tagctgcgag ctcgcagggc | 300 |
| agtgttctcc cagcctggcc tgctcccgg gagccctcag acagcctgtt tgccgtgcgg | 360 |
| aggcacctct ggggaagcca tggaaacggc acctttccag agttcttcca acatggac | 420 |
| tatttcaagt tccacaacat gagaccgcca ttcacctatg ccacctcat ccgatgggcc | 480 |
| atcctggaag ctccagagaa gcagagaaca ctcaatgaaa tctaccactg gttcacacgc | 540 |
| atgtttgcct acttcagaaa ccacccggcc acctggaaga atgccatccg ccacaacctg | 600 |
| agctcgcaca agtgctttgt gcgag | 625 |

<210> SEQ ID NO 10
<211> LENGTH: 1191
<212> TYPE: DNA
<213> ORGANISM: Homo sapiens

<400> SEQUENCE: 10

-continued

| | |
|---|---|
| atgcccaacc ccaggcctgg caagccctcg gccccttcct tggcccttgg cccatcccca | 60 |
| ggagcctcgc ccagctggag ggctgcaccc aaagcctcag acctgctggg ggcccggggc | 120 |
| ccaggggaa ccttccaggg ccgagatctt cgaggcgggg cccatgcctc ctcttcttcc | 180 |
| ttgaacccca tgccaccatc gcagctgcag ctctcaacgg tggatgccca cgcccggacc | 240 |
| cctgtgctgc aggtgcaccc cctggagagc ccagccatga tcagcctcac accacccacc | 300 |
| accgccactg ggtcttctc cctcaaggcc cggcctggcc tcccacctgg gatcaacgtg | 360 |
| gccagcctgg aatgggtgtc cagggagccg gcactgctct gcaccttccc aaatcccagt | 420 |
| gcacccagga aggacagcac cctttcggct gtgcccagag ctcctaccc actgctggca | 480 |
| aatggtgtct gcaagtggcc cggatgtgag aaggtcttcg aagagccaga ggacttcctc | 540 |
| aagcactgcc aggcggacca tcttctggat gagaagggca gggcacaatg tctcctccag | 600 |
| agagagatgg tacagtctct ggagcagcag ctggtgctgg agaaggagaa gctgagtgcc | 660 |
| atgcaggccc acctggctgg gaaaatggca ctgaccaagg cttcatctgt ggcatcatcc | 720 |
| gacaagggct cctgctgcat cgtagctgct ggcagccaag gcctgtcgt cccagcctgg | 780 |
| tctggccccc gggaggcccc tgacagcctg tttgctgtcc ggaggcacct gtggggtagc | 840 |
| catggaaaca gcacattccc agagttcctc cacaacatgg actacttcaa gttccacaac | 900 |
| atgcgacccc ctttcaccta cgccacgctc atccgctggg ccatcctgga ggctccagag | 960 |
| aagcagcgga cactcaatga gatctaccac tggttcacac gcatgtttgc cttcttcaga | 1020 |
| aaccatcctg ccacctggaa gaacgccatc cgccacaacc tgagtctgca caagtgcttt | 1080 |
| gtgcgggtgg agagcgagaa gggggctgtg tggaccgtgg atgagctgga gttccgcaag | 1140 |
| aaacggagcc agaggcccag caggtgttcc aaccctacac ctggccctg a | 1191 |

<210> SEQ ID NO 11
<211> LENGTH: 1411
<212> TYPE: DNA
<213> ORGANISM: Mus musculus

<400> SEQUENCE: 11

| | |
|---|---|
| acagtcacat ctcagcagct cctctgccgt tatccagcct gcctctgaca agaacccaat | 60 |
| gcccaaccct aggccagcca agcctatggc tccttccttg gcccttggcc catcccagg | 120 |
| agtcttgcca agctggaaga ctgcacccaa gggctcagaa cttctaggga ccaggggctc | 180 |
| tgggggaccc ttccaaggtc gggacctgcg aagtggggcc cacacctctt cttccttgaa | 240 |
| cccctgcca ccatcccagc tgcagctgcc tacagtgccc ctagtcatgg tggcaccgtc | 300 |
| tggggcccga ctaggtccct caccccacct acaggccctt ctccaggaca gaccacactt | 360 |
| catgcatcag ctctccactg tggatgccca tgcccagacc cctgtgctcc aagtgcgtcc | 420 |
| actggacaac ccagccatga tcagcctccc accaccttct gctgccactg ggtcttctc | 480 |
| cctcaaggcc cggcctggcc tgccacctgg gatcaatgtg gccagtctgg aatgggtgtc | 540 |
| cagggagcca gctctactct gcaccttccc acgctcgggt acacccagga agacagcaa | 600 |
| cctttggct gcaccccaag gatcctaccc actgctggca aatggagtct gcaagtggcc | 660 |
| tggttgtgag aaggtcttcg aggagccaga agagtttctc aagcactgcc aagcagatca | 720 |
| tcctctggat gagaaaggca aggcccagtg cctcctccag agagaagtgg tgcagtctct | 780 |
| ggagcagcag ctggagctgg aaaaggagaa gctgggagct atgcaggccc acctggctgg | 840 |
| gaagatggcg ctggccaagg ctccatctgt ggcctcaatg gacaagagct cttgctgcat | 900 |
| cgtagccacc agtactcagg gcagtgtgct cccggcctgg tctgctcctc gggaggctcc | 960 |

| | |
|---|---|
| agacggcggc ctgtttgcag tgcggaggca cctctgggga agccatggca atagttcctt | 1020 |
| cccagagttc ttccacaaca tggactactt caagtaccac aatatgcgac cccctttcac | 1080 |
| ctatgccacc cttatccgat gggccatcct ggaagcccg gagaggcaga ggacactcaa | 1140 |
| tgaaatctac cattggttta ctcgcatgtt cgcctacttc agaaaccacc ccgccacctg | 1200 |
| gaagaatgcc atccgccaca acctgagcct gcacaagtgc tttgtgcgag tggagagcga | 1260 |
| gaagggagca gtgtggaccg tagatgaatt tgagtttcgc aagaagagga gccaacgccc | 1320 |
| caacaagtgc tccaatccct gcccttgacc tcaaaaccaa gaaaaggtgg gcggggagg | 1380 |
| gggccaaaac catgagactg aggctgtggg g | 1411 |

<210> SEQ ID NO 12
<211> LENGTH: 1411
<212> TYPE: DNA
<213> ORGANISM: Mus musculus

<400> SEQUENCE: 12

| | |
|---|---|
| acagtcacat ctcagcagct cctctgccgt tatccagcct gcctctgaca agaacccaat | 60 |
| gcccaaccct aggccagcca agcctatggc tccttccttg gccctggcc catccccagg | 120 |
| agtcttgcca agctggaaga ctgcacccaa gggctcagaa cttctaggga ccaggggctc | 180 |
| tgggggaccc ttccaaggtc gggacctgcg aagtggggcc cacacctctt cttccttgaa | 240 |
| cccctgcca ccatcccagc tgcagctgcc tacagtgccc ctagtcatgg tggcaccgtc | 300 |
| tggggcccga ctaggtccct caccccacct acaggccctt ctccaggaca gaccacactt | 360 |
| catgcatcag ctctccactg tggatgccca tgcccagacc cctgtgctcc aagtgcgtcc | 420 |
| actggacaac ccagccatga tcagcctccc accaccttct gctgccactg ggtcttctc | 480 |
| cctcaaggcc cggcctggcc tgccacctgg gatcaatgtg ccagtctgg aatgggtgtc | 540 |
| cagggagcca gctctactct gcaccttccc acgctcgggt acacccagga agacagcaa | 600 |
| ccttttggct gcaccccaag gatcctaccc actgctggca aatggagtct gcaagtggcc | 660 |
| tggttgtgag aaggtcttcg aggagccaga agagtttctc aagcactgcc aagcagatca | 720 |
| tctcctggat gagaaaggca aggcccagtg cctcctccag agagaagtgg tgcagtctct | 780 |
| ggagcagcag ctggagctgg aaaaggagaa gctgggagct atgcaggccc acctggctgg | 840 |
| gaagatggcg ctggccaagg ctccatctgt ggcctcaatg gacaagagct cttgctgcat | 900 |
| cgtagccacc agtactcagg gcagtgtgct cccggcctgg tctgctcctc gggaggctcc | 960 |
| agacggcggc ctgtttgcag tgcggaggca cctctgggga agccatggca atagttcctt | 1020 |
| cccagagttc ttccacaaca tggactactt caagtaccac aatatgcgac cccctttcac | 1080 |
| ctatgccacc cttatccgat gggccatcct ggaagcccg gagaggcaga ggacactcaa | 1140 |
| tgaaatctac cattggttta ctcgcatgtt cgcctacttc agaaaccacc ccgccacctg | 1200 |
| gaagaatgcc atccgccaca acctgagcct gcacaagtgc tttgtgcgag tggagagcga | 1260 |
| gaagggagca gtgtggaccg tagatgaatt tgagtttcgc aagaagagga gccaacgccc | 1320 |
| caacaagtgc tccaatccct gcccttgacc tcaaaaccaa gaaaaggtgg gcggggagg | 1380 |
| gggccaaaac catgagactg aggctgtggg g | 1411 |

<210> SEQ ID NO 13
<211> LENGTH: 1298
<212> TYPE: DNA
<213> ORGANISM: Macaca fascicularis

<400> SEQUENCE: 13

```
atgcccaacc ccaggccagg caagccctcg gcccttcct tggcccttgg cccatcccca      60
ggagcctcgc ccagctggag ggctgcgccc aaagcctcag acctgctggg ggcccggggc     120
cctgggggaa tcttccaggg ccgagatctt cgaggtgggg ctcatgcctc ctcttcctcc     180
ttgaacccta tgccaccatc gcagctgcag ctgcccacac tgcccctagt catggtggca     240
ccctccgggg cacggctggg cccttgccc cacttacagg cactcctcca ggacaggcca     300
catttcatgc accagctctc aacggtggat gcccacgccc ggacccctgt gctgcaggtg     360
caccccctgg agagcccagc catgatcagc ctcccaccac ccaccactgc cactggggtc     420
ttctccctca aggcccggcc tggcctccca cctgggatca acgtggccag cctggaatgg     480
gtgtccaggg agccagcact gctctgcacc ttcccaaatc ctggtgcacc caggaaggac     540
agcacccttt cggccatgcc ccagagctcc tacccactgc tggcaaatgg tgtctgcaag     600
tggcccggat gtgagaaagt cttcgaagag ccagaggact tcctcaagca ctgccaagca     660
gaccatcttc tggatgagaa gggcagggca caatgtctcc tccagagaga gatggtacag     720
tctctggagc agcagctggt gctggagaag gagaagctga gtgctatgca ggcccacctg     780
gctgggaaaa tggcactgac caaggcttca tctgtggcat catctgacaa gggctcctgc     840
tgcattgtag ctgctggcag ccaaggcagt gccgtcccag cctggtctgg cccccgggag     900
gcccctgaca gcctgtttgc tgtgcggagg cacctgtggg gtagccatgg aaacagcaca     960
ttcccagagt tccttcacaa catggactac ttcaagttcc acaatatgcg acccccttc    1020
acctatgcca cgctcatccg ctgggccatc ctggaggctc cagagaagca gcggacactc    1080
aatgagatct accactggtt cacacgcatg ttcgccttct tcagaaacca tcctgccacc    1140
tggaagaacg ccatccgcca caacctgagc ctgcacaagt gctttgtgcg ggtggagagc    1200
gagaaggggg ctgtgtggac cgtggatgag ttggagttcc gcaagaaacg gagccagagg    1260
ccaagcaggt gttccaaccc tacacctggc ccctgacc                          1298
```

<210> SEQ ID NO 14
<211> LENGTH: 30858
<212> TYPE: DNA
<213> ORGANISM: Mus musculus

<400> SEQUENCE: 14

```
gttaacagtt cttagaaaaa tggaaggaaa tcaagaacaa aactgtacat acggtgtgcc      60
tgttcatttt cgagaataaa accttttggc acctgtccca caaatgccat gcagtctctc     120
tgggggcag tgaacacaca gtgggccagg acacacagtg ctgggaatgt gttggcatgc     180
cttacttgag tacttgtgaa tgagtccagc ccatcttacc tagaatggac cactctactg     240
ggagtgaaag ttcttcccac cataaagaaa gtcaacagct acttgacttc agatagtacc     300
tggagaccaa gggataagac ttgagaaagt ggtggcagcg gccccagccc aggccagcca     360
agacagaaca gaaagatcag ttagcagaga taaagaatga gtgagtgaat gagggccaac     420
aagccccaa gagaaatgca agtagactc ataccacgg ccacaatcat cgtctgggtc         480
ctacgtgagc acgccaagtt tcaaagaact gtgcttgccc gaactgggtc atgtgctgag     540
ccccaaaggg aaacacgcac agcccagctc ccatggagac aatctgatga tgctgtctgg     600
gggggggggg gggggttttg gcttcaaaaa acttggaatt cgggtcacct aaagccgtgt     660
gcgtaggggg ggtgaggtga ggaggctgtg acatcatcaa gttatgtagg actctgccct     720
gctttctctg agtgtcagcc tcaactctag gacttgtgtg cattggaggg cagcttacca     780
tgcatgcttc aagcttcatc taactgacac tcccgtggcc acagcccagg gtgagaaaac     840
```

```
catttcacct cataagccag cacattcacg agtaaataca gacacagaca cactgagaac    900
tgaaacactt gctcttcaaa gtaatactca cctctactgc atgtcaaact gcgctgggct    960
atctcctata ccatttgcca atgtttgttg gaagccagca aactgatctt gcatctcaat   1020
aaatgcccag aaaatgcaat gttgaatagt cccagctcta ccacaaatca gctgtgaccc   1080
gggacaaatt tcctcatctc ttgtgcccta gtctcctcat ctataaggaa gaaatggtag   1140
taatacttca gggagctttt cgatggactg aggaaacatg caaagcacca ataaagtgct   1200
taaaactaag tcttttggaa tagcgctggg gctctgaaaa aaggaagcaa cttgtccggc   1260
cattcccagc tgtaggcccc atccagcagc ctagcgctgc agttctcaac tggagcacta   1320
gcagaactac acaggctcac atccctgctc tgccactttg ctgtgcagcc tccagcccac   1380
aaccttaacc atgatggcct accagttgtc tgtagaacaa agggacactt tctcatgaaa   1440
tcctctctcc agaccactta gatgattccc accccaccca tttcaactct attgttctca   1500
tttctgtgag gctgccaata gctacccatt cattcagtta caggtatacc taaaacctgt   1560
gcatcaggga tagtgacagg agacacactg gtgagcaaac ccagcaatga aatttagaat   1620
ttgatgtgga gacatttgaa aaaatactca aactcgttct ttcaacaaat atttattgag   1680
cacctactaa gtgccatgca ctaaggcagg cctgtgaaaa tacagtggtc accaatgcag   1740
agcatgtccc tacccctcac ggagcttaca gtctagcatt gcagtcaccc attaatcccc   1800
taataaaggc cttactacag acggaagcca gtgcctttag aaaaggaagg aacatgctag   1860
aacactaggc cctggcacag actagaatca gcagggcttt aaggatgctt agaaagcaag   1920
tgcatgggta tggaataaga ggttgtttgg gggcactgag tgggagacag ccaagcttga   1980
gaagactaag gattcagtca agcagacacc aagtttagta gttgaggctg acagaacagg   2040
agaaagggcc agagattttg aagaaagcaa gtagagggcg gtcccaaagc cagaggggac   2100
cgagtaggag cagttagccc tttcaagaag aaaacaacgg agcctttcag tgtggccaaa   2160
gccagggact aataaaactg cagacaaagc aagtgctgtt gactcttcag ggggagggga   2220
caagggtgat catcaagtac tgaccagagg caaaggggcaa ggtggctcag caattaagag   2280
agagaccctg gcctgaggct aggtcaacag aggaccaggt gagacagacc tggaaaaaaa   2340
gcctgatgaa agacaaatgg ggcttatggt tgcagcctct ggacaaatgg cagaaaatga   2400
agctctggag tcaagaacag aaactggcct gaaatgggaa caagggaccc cctcctcatg   2460
tacaatgtga ggggtgttgg tgttcagacg tgggggctct aaggagcagg cattccattc   2520
ttatggtttc tattgtgttt gaagaagcaa aaggcagagt gtaatgataa agaacacttg   2580
acgggatccc atgaaagagg agccgagggt ggatcaaagg acacacagga caatgggca   2640
ggatggaaga tggtccttaa cttgggggaa ggctcacatg ctggcctatg tggcattttc   2700
caacttgact tgctgatcag tgctatgaat aaaactgggg acttaaggag gctaagctgc   2760
gcaagcttcc ttccctaagg aaaccctctt agaactgagg agtctccatg aggagaatct   2820
gaggggtaaa cacattcttg gtgaagcaaa cagtatgagc gacaaccca aagcaggagt   2880
aacagaaggg atgtggcgac aagagctcgg gagcagaaac caatataaag ccagactaga   2940
tgctaacaga ggctgaagca ggcatcggtg agggtgtgta agggccagcc agatttttgt   3000
tggtctttat ttttaagagg aataggatac ttcctcagag tataaagcca agacacacca   3060
gaagggctcc ttcccatatc agtccaatca ctgaggactc aaaacctctg tgctcaccca   3120
gaagagggat ttaaaggaat ctagctcaca gaaaacgctg ttgagcacaa atgaaactat   3180
acaaaaatac tcagcaaagt gcccagcaag gaaagggggc ttggccacat atcacttggt   3240
```

```
agggtctcac ataacccttg cccoctggct ctaccccaag ctcctgggag tcttaggacc   3300
agtctgtgtc ttctctgctt gttcctagca ctgtgctcag cacataacag gctctaccaa   3360
aaatgctgct gatggattct ctctaaacct actgagtact gcaaacctgg tcctgcaagc   3420
tagggaaagc agccagctca gcctctggac tacatcctca tggctgccaa tcatctcttc   3480
tgaccctacc tgccaagggc cagctgcaca gtgggcctgt ggccaacgat tctgaagccc   3540
tctacagcag gcctcccaca gataagaaaa gggatcccct gaggtccacc accatttccc   3600
cagagggctg gatcacgggg ggtagctatt cttcaacagc acttcaaatc agcagcagca   3660
cacaggcctt aaaacaataa taagttgaaa tgtatttgct aggaaagtca ccgacctaca   3720
aagaaaacct tatcgctgat ctagcagcgc acaccagcct cccctttgca agagctgaga   3780
tcaaaagata aagaagctat caaaaagcca tctgccccact aaaataaca tctcaagtca   3840 cgttgggaac cacaaacatg gggccagcta ccaaaacaat tgtctaaatg aactacttca   3900
atttctcctt aaaaccaccc atgtatttta aagaaaaac ccctctcca cccaccttgg   3960 cacggcaagg ttttgatttg tctgttccct tcctttcaca ttcttgaaaa tgaccaaact   4020
tcagtactca actgtcttat cttccagaaa gggctcccac aactgccgat ggaataagaa   4080
gtgattgaaa tgcaggcgat tctggggggca ctggaactgg gtggcggcta catacacata   4140
catgtgcaat tcttccgagc catgccctcg ggggtcagta ccgtccactt gtgtatatct   4200
caataaaaca cgaagcacac gtaacaggta caggggggaa aggaagaact aagagcgcca   4260 aacagtgaaat gcggactttg ttttttaaact agcatcccta acatttcctc cctggcctgg   4320
ctatttacta gctgagtgac tctgagcaag ctcgagcacc tctccgagcc ccccacccca   4380
ccccatttcc catgaactag gactcaatat agtgcctaca gtcaacagca cattcagctg   4440
acctcaagag gagaatgtcc ctaccactct taacagagat taagaaatgc tgcccaccag   4500 acctttaca gctacaatta tgcctcagtt accttcccta cgggtactgc atccaattca   4560
accacacaat gggaaagcca ttcctctctg accaatgagg aaactgagac aagagtacac   4620
aacaaagctg agtttgggaa aggatacatg gactgtagtg agcatctaag cttcgatgct   4680
aattaccagc actatggcac tacttggaac taggctcgat cctgagtgct tctgctcatc   4740
ccgtgaggtc tgtgccataa cttcctgttt tacagatgag ggtgtttatc tacggcacga   4800
tgcagctaag aattggatac ggtcacacta aaaagtggca ggcttagggt ttgaacccag   4860
gtaatcgaat ggcagaatct aaatgcttca aggtccatcc acgaagagct aaacctttca   4920
cagcctaagc ccttaccaca accagcagat cccacagcac cctgctccat catgcagctt   4980
cgaagggaca aagggcaac ctccccttcc catttctcat aggagcagga aaatgtatgc   5040
atttcatagg ggctctaact gaccccgggc attaggccta gctggagccc ttgacaaacg   5100
tatagccctg gtaaagacct agaaaagcat tatatcagtc agtttacaag aggtgtgcaa   5160
aaaaaaaaaa aagaagagc gatgtgacct tcaagtccgc ttctcatctg tttccgcctc   5220
tgccaaggct aatgttttta tgtgagaata gagcctcgct ccctaaactc cactggaggc   5280
ctcagactac cagaggaaca gttttttaaaa aaaaggatgc atagacttca aagccagaaa   5340
tggttgaaac taaaaagcca agtaccacca cttcctcaac cagtttctct aactctggct   5400
tcctgctgtg gcagatagga atcagactga ctcccccacgc cgggagaccc ttagtccaca   5460
ccttcgcacg tcatgttctc tccactccag cacactggct gacagtcata cgaaacccag   5520
aaccacctca ggactttgct gtccccacta tctacatcta cctcccctgt atgtgcatca   5580
ctgctccgta ccactctgga ctcaagttta aatgccacct cctcagaaag agtcctacct   5640
```

-continued

```
ggtccaaact ctaccaactc gctcgtccat aactcttcgt tatcaccgtc tgggactctt    5700
cacaagagct caccctcaac acgtctgcag cagccactcc ctccagagcc ttacagtatt    5760
ttcctctcag cactaacctt agccctattt atcttatctg cttgtttgct tttgcattct    5820
gtttcccaga ggagcctttg cgggatggtt ggggacaggg aaggtgtctg tcttgttcag    5880
ggccttatag tggaactcaa taaatggatg ataccccaga atttaaaaca gtgcctagca    5940
catgtttggc ctgcactact cttttgaccga atgcaccctc ctgcctgtcc tggagagcag    6000
gcctggggga gggggaagtg ctgggatggg aggcttctac atccagccct gtgttggtgg    6060
aggtggcgct ggcagacatt acctgcgcct caccggcttc atgcagctct tcagctgcct    6120
ggcctcagcc tccacaggac cctggcactc aggctgtggc tccagctgct gcagctgctg    6180
ctgctggggc agcccttcgg catcagtggg tgtgggagcg ggtgcgatcc ggagcaggac    6240
agtgtagttg cggccatggt tgttggccca gaaagtgccc tcggggtct catagcgcac    6300 cacgaagtcg aggcgcgccc catcgctcgc gccctcagca aagggcagct ggaaggcaaa    6360
gcggtcagtg cagccaccgt cgtcgggtga ggaggctgac atctggccag ggcccaggcc    6420
tagcccggga tccaggaggg gatctcctgc tcctgttcct cccactcctg ccccaggcgg    6480
gctgcgtggg acatagcggg ctgggtggtc gcagaaggta gcccaaccgt cgtgtgaggc    6540
ccgcacgtgc accgccttct cgaaggagcg gttcagcacg cgcaccaacc cgcgcaccac    6600
tggcgggcgt ccccccaggca cccacacccc ggaaccccg ggaaccgctc caggaggcgg    6660
cagcagcgcc tccaactcca ccatcacgcg ccccaaccgc tccagacggc ccagcgcggg    6720
cggcaacgaa aatgtgggca ccaggtaaaa ccccccgcca gcgggaacgg ggcacggcgg    6780
agagggatcg ggaaaagcct cctcttcctc ctcccttca tccccatcct cgccatcgtc    6840
ttcctcatca gccccgccac cgccgccatc ttgcccggtc gccgccgcca tcttgcccgc    6900
cccgggcccg cccacggcc ggtagcggcg tactgcgcca gaggcagccc cagggcctcg    6960
tcagcgaaca gcaccctccg cggggccacc gccgcctcag ccgaggcgcg ggctctccc    7020 gcagccggcg acgggggcgc gggatgccgc agcggtggct ccacaggggc cgtgcgcgcc    7080
atatcggcgg cggcggcggc ggcaccgacg gcaccgcgg tgggaccggc ggggggcaggg    7140 cctgaaaagg cgggcagcca atgagaaagc cagaacaggg gggtgggct ccagtggagc    7200 gtaggcggtg agctagagac aggtacggcc aacagccaat ggcagccac gcgggagtga    7260 cgtacaggtg attgacaagc aggagaagct agcaaccaat gaggacgccc gcgcgtgggc    7320
gggatggaag gcgggatgat aacggaatca atggagaggc ctgagtaggg ttaatgcggg    7380
cccgaagatg tagcagcagg agtatgacaa ttagtgggaa agtctgagca cgaagggcat    7440
ggtaggcggc gggaagatga aatggctaca agcaatgggg gcaacgggga gcgaacccag    7500
aggtccaaaa actgggagat ccgcaggttg cgtaggcggt gagacgtaag acagataaaa    7560
tgaacagcca atgagaact gcacgcgaat gatgtagaga cagaatgacg ataatagttg    7620
caatgagcca atggaggagt ctagtgagcg cacactatgg cttcaagagg tggtaacaag    7680
gtagatctag ccaatacaga gactgaacag agacgggaag gctgtgtgtg agcagacatg    7740 gaggcgggc tgtagcgggc gggggggggg gagcactaag gcatgtgagg agtgaaggtg    7800
ggagcgagaa agaaatgggg atccaggggtg aaggctgtta tatctcaaag gacagtgcca    7860
gtatgggatt aaccaaagct gaaactagag aaatgtagcc agaaggaaac tttggaggca    7920
agatgggaac tcatacccac ggatggtagt gtaggtgctg tgaaggaaag catgagtagc    7980
caataaatag gctgagttgg aagaaggtgc ataggctgag cctgagctat tgagtgattg    8040
```

```
agcgcagaat cagaattcat tcaaccagta agatcggacc tctggggaat ggctttacct    8100
ttccctaatc ttccatgact ccccatggct ccacgaatac ccagagcccc taaaagccca    8160
gactgcaccg gattgtgaga ccaaagcaaa acagttctat cagttactgg gtgtgtcctg    8220
ctggccccac accaccacac acacctccca gccttattgt gaccaatgca actagccatg    8280
aacgttctta actgttcctt aaagtcccca gttgagcatt gatgttcttc aggacttggc    8340
actattgcat gaatcaatcg caaaatagga aatagaacct ttttggaaga attagctttt    8400
tccaactcac acttagcaca cattgactga tagtatgtca tcacaagctt atcagctaat    8460
gtacattcaa atcagagtcc tgcccttctt gctcattttg acactttgca ccccacagtg    8520
gctttcttct cccccccccc cactttccca atctcctctg cttagagtgc tgtcccatct    8580
gtttctttca tctagtgaat tctttccatt ctccctctga gatggcacct cctatgggaa    8640
tgacctggac tttgccatcg tgttcattca catatccccc actcccattt actaacttag    8700
taagacttag tgtttgccat atgccaggtt caggagtgc ttttatctaa ccctcataag     8760
acccctaaca ggaaggcccc cacagtctct ctgctcctcc tgtctgtgtc cagggtcatg    8820
aaaggaatat gtccagctac aagtagcaga agaataatgg cataatgaag gtagaacttt    8880
tttttctcat ctgaaagttc aaggcagcaa gtgctctcag gactccatcc tatctgccca    8940
ttttgggtat caactgtgcc ccggtcttgc ctcagagtct cattcttcag caaatcctgc    9000
aggttatcta cccaacgcat tttccaagca ggatatggtg atgtatgcct gtaatcccag    9060
cactcaaggg gctgaggcag gagaatcacg gaattccaag cctaggctac aagtgtgacc    9120
ttgtctaaaa aataaaaagg gttaagtgta gctcagcggt aaaaaccact tcctagaaag    9180
tgcatgggcc ccatctctag catcattttt tttaaatccc aaatccacct tttcactacc    9240
actccatcaa caggaccagc accagtccca gtccctgga ctactgtagt cacctccccc     9300
tggttggtct ccatcccatg ttctacccccc tattccatat tcagccatct aagacatcct   9360
cttaagtcct aacagcaatg tctctcctct gctcccaaca ccctctggct tcctctacac    9420
taagaggaag agccaacctt caccatgtcg taagcgcaca agccagctag ccccgtctga    9480
ccttcctcct gttctctccc ttccagtcat gtcactccaa ccacacaaga ctccttgctg    9540
accctgtaca tatccagcac actcacctca ggacacccac actgacccct ctctcctgga    9600
tctgcagatc tccccatcac tctcttcttc atctatgcct gctctttgtc aaagatccct    9660
ttccctggga atgctccccc tgacctgtta aatcctgccc cattcaccat caactcctag    9720
ccctcccagt ttgcttcccc aggaacctac atgagccaat atagtaatgg tggagaggaa    9780
ataccaccct ctgacaagca aaaccctagc caccatgctg caaagaccct agctttacac    9840
ttcagtaacc ttaacactcc cgcacccaca gccccattca aatagcctcc tggaaacctg    9900
tgtcacttac ccctcattta cttatcctgc cacctctctg accaagtttt cgcagaatgg    9960
caggaagatg gtgacgagga tataaaggaa gatgcagacc aaaccatgga ccctgagaaa   10020
atgagtacct attccaaaaa gagacaggtg acagggcagg ggactagaac tgtctcagag   10080
acatagaaga tacagggact agttgggccc aagtgtacag ggagcaggga ccattaactt   10140
tggggcatag ctacagtcag ctgcccatta cctgttaggt atgctcttca cccctcccct   10200
attccctccc acacacaacc acaactgtta agctcctaag atccatgcag acctccaaag   10260
taagaggacc tcatcccacc tctgcccctc cctccctctc aactcaggac ctccccggc    10320
ttccaggcac cacacaggcc atgtttggtc ttagatgtgt cccaccaact tagaagcccc   10380
aaccagtgaa agttttgctt tgaactaatg ataggaaggg ttgagggttt ttttttttta   10440
```

```
attgttgttg ttgttggctg gtattttttgg gtcttttttt tttctattca ctttgttttc    10500
ccctcttgtc tttataaagc caagccatca gttccagtct tgttatttcc aaaaaggtga    10560
gttaagatga ggaaagtcag tctctttttt gttgttgttg ttgggcgggg ggaggtgct    10620 cagaagatag ccgaaaggga caaaaagtgc aaatgaggga aagagcaaag gagtgtggga    10680 attgttttact aggttagcat catgtgaata aaaacgtatt tctactttct cttcctcagg    10740
cctgaagcca gtcttgcaaa gaggtggtgg tggccatgca gttggatacc tggaactctt    10800
agctctctgc aggatgccag ggcaccaaag gctggaagcc ttagccgtgc cttgtcagga    10860
aaaactctgt ggaggctcgt ctgtagtaaa cagtggttac agggagccgg tctgtgccaa    10920
atcgaggaca cgcagctgcc agatcttgaa tacaaacctt aaaacctcac aaacatcaag    10980
ttccagagga gtctccaagt cctagaactt ctatgacact gttggcttca ggaaaactgg    11040
tcacttcaga gcccaatgct aaggacccct atttcccaaa attgtgatct taagcaagct    11100
gcacctccat tttgcccatc ggtctaaaaa caatacagcc atgatgagat ggacctcaga    11160
gggtgagaag tgtttggctc tgtctggaat gtagaaaatt ctagttaaat gttggctacc    11220
aaaattatga cagctgttta gaatcctaaa ccttttgcaaa cgggagtgtt tcttttccttt    11280 tgtttgtggt tttggttttt tgttttttgtt tttttgtgtt ttttgttttt ttcttttttct    11340 ttttacacgg aatctggcta tatagcccca agcaaccttta aactcttgat tcttctgcct    11400
cagtttctgg ggtgctggga ttactggtat gtgatactgg atgaaactgg aacttttcag    11460
agtagactgt tacaaagttt agaatcatca ggctatggct atattgttcc tgacaggact    11520
aggaccctgg gccgctatgt gtatggtttt tttgtttgtt tgttttaaca acccagagcc    11580
ttgtgcgtgt taaacaagca ctctggcact gagctgcaat ggccagcctt tcttccccctt    11640 gcccttcttg gtgatgctgg ctgcattaac agccactggg gctgttccca ggtgggtggc    11700
tgctgggtca gggcactcag cacaaacatg atgtggggct cactcagaga ctcgcagcag    11760
cttctgggag ccagccattc tgagactctc tgattctgtg aatttgtggg gggagtacag    11820 cccactttttt tctccatgaa ttgctttcca tgcctcttgc cttctgtgga aagaaaggct    11880
acaggagtgg ccagctctgc caagccttgg caacatgatg gtggtgatca tatgcatgct    11940
tgctaaggaa atactgaggt ttggagcaga aggaagcctc tggagacaga gcactacccc    12000
acctctcccc tggctgcttc ccattcacat ggcaggcttc agatcccttc ttctgttcaa    12060
cccagcgatc ctccaacgtc tcacaaacac aatgctgtct ctacctgcct cgggatgcct    12120
ttgtgatttg acttatttttc cctcagtttt tttttttctga ctctacacac ttttgtttaa    12180
gaaattgtgg tttctcatga gccctgttat ctcattgata cctttacct ctgtggtgag    12240 gggaagaaat catattttca gatgacttgt aaagggcaaa gaaaaaaccc aaaatttcaa    12300
aatttccgtt taagtctcat aagaaaagaa taaacaaagt aagagagcaa agaaaaaaaa    12360
actacaagaa ccccccccccc accctgcaat tatcagcaca cacactcatc aaaaaaaaat    12420
tggattatta gaagagcgag gtctgcggct tccacgccgt ggttttttctt ctcggtataa    12480 aagcaaagtt gtttttgata atgtggcagt ttcccacaag ccaggctgat cccctctag    12540 cagtccactt caccaaggtg agcgagtgtc cctgctctcc cccaccagac acagctctgc    12600
tggcgaaagt ggcagagagg tattgagggt gggtgtcagg agcccaccag tacagctgga    12660
aacacccagc cactccaggt aaggactttg gaaactaata ccattcatcc taaatgccag    12720
ataggtggag cagttggtcc ttagacaggg gcaaaaagaa gtactttgat tgtttgatgc    12780
acagataaac aggatttttt tttaacatat gtctatcaac tgctggtctc caggaatgcc    12840
```

```
ggagctttag gcaactcaag atgctgtcca gctataacta gaaactagaa gtgcatctct    12900
tgtttctttt cctcctgctg tcttccattt cttctcctgt ctcccctgc ttctttgcct     12960 gtctctgcct tccatcagtg cccagtctct gtctctttcc caggctctga ctatatgcct    13020
gtctgtctct tccagcctgg ccagccacag tcccttcttt cctcccgct ctctgactct     13080 cggctcatct tccttcagct gcttttgcac ccggtattga gcgcagatat ttgtacacaa    13140
ctggcgctta ataataatgg cttaagagct ctgttttcca agaacgggca ttagttctgt    13200
gtgtcttagg tttgtgagct gtcaggtcag tcttagcatt taactgacct tctgcttgtg    13260
tcacgcaaga taacaccctc agtcagccac agtttagcaa aggactatat gactgtgagc    13320
agaatccatg tgcaaggaga gcaggcagtt caggacgagg gtgagctggt ctctgcaggt    13380
ttagtgctgt ggcactgtgc ctggtatatg gtgagttctc actgtttgct attagcattt    13440
ttaaacaaat tagaatcgtg ctatagattg gatttgtttc tgctctgttc aagcgatacc    13500 attttgtag catactaaaa taacgaacac gtgatctttt atgtctgccg tgactgtcct     13560
cacatcacca tgaatttgat tacctgaatt aagtgctgat ggtgggatat ttgggtttct    13620
tctgattcta aaactcccata cctgactcca tggatcctga aaatggagta gctggggaag   13680
aaggggtgta catcttaagg ggttttgccc tctctacaaa ttgcttttcc aaaacgttgt    13740 cttatttct gttgtttcta ttcaagttaa ttttaggtgt gtgttaccat ttttaatcct     13800
tccccatcat aagaaaaatg acaagtatta aaattttgca ttttggttac ttttaatgac    13860
cactgaccat ttgtgctctg taggctagag ttttatgatc acattcttca tcctactaaa    13920
ttgctcatga tttttcaaaa ttgctaatag ctcttaattt agaaaggata ataactattg    13980
gctatatgta tatgacacat atttccctga aattcatcat ttgtgtgtat gtgtatttta    14040
attgtattca tttacttagt ttatgagcat gcatgttctt cctgcatgtg caccatatgt    14100
gtgcctggtg cccacagagg ccagaagatg gtgtgggatc tcatgggact ggagttacag    14160
atggttacgt gggtgctggc gcttatgtgg cttctttcta tggttttgtg tttaaaagcc    14220
ttttaccact tgaaaatgag aagctacctc ctctacaaga gcagcagtgc tcttacccat    14280
ggagccatct ctccagccct atttgtatgg gggggggggg tcttctgaga caaggtctca    14340
ctctatagcc ctgactggcc taaaactcac tgtatagacc aggctgacct caaactcaca    14400
aagacccatc catctgcctc tgccttctga gaagtgggat agaagacata caccaccacg    14460
gcgggcaatc acttgctttt tttccctatt tattgtgctt tgtaatgcat gtgtctttta    14520
ggtctttaga ttactctttt cttgtggggc ttctgtgtat ggttttgtgt tttaagtctt    14580
ttgcacttga aaatgagata actgttcacc ccatgttggc ttccagtctc ctttatggct    14640 tcatttttc catttactgc agaggtcaaa agtgtgggta tgggagccag actgtctgga    14700
acaacctagc ctcaactcaa gtcatctgtg tgaattttac ccaggctctt aacctctctg    14760
tacctccatt tcctcgtatg tactgtgatg attataacag tacctacctc agaggatctt    14820
tctgaggatt attttattta atgatggtag gtgctcagca caaggccaaa caacaatgat    14880
agacattaaa acgtatctct ctagtgggtc tggaaattat tctagagcgt ctgatgacag    14940
cgacatttca agtgggcagg gaggtattgg tgggaaagtg ggctatctac ccagtcactt    15000
tattttcccc taattgtctc agaatcattt gttaatctgt cctgcactgt tcctcatgtt    15060
gaaatgttgt gttcatcaca aattccattc cctctgtgca tgggtctctg ccacggtttt    15120
ctactctaat ctgctcctta gtgtttattc ttgtacaaag cccacactat ttttctgatg    15180
ttgctttgca aaacaattca ataccagcca tgggtgtctc tggcacctag cagcatcagt    15240
```

```
cctccagcca gaggccagtg attattttca gtcctttctc tcactccctc tctctctgtc   15300
tctgcatgtc tgtctgtctg tatatgtctc tgtcttgttc attctttctc tgtcactttt   15360
cctctaaact gctctcactg tctctctcta tgagcttgat tcctattcca tctcatgttt   15420
ctctctatat atttctctat ctgtatctct tctatatctg tattcacaca catatgatat   15480
atatatatat atctcaatat atatatatat atatatatat atatatatat atatatatat   15540
atatatcaat atatatatct cataccatac catacataca tacggctata tagctccata   15600
agatttaccc cagccacgag acagaaagat gctggccttc ctccacctcg tactcttccc   15660
tccccagtct agaagggcaa actgggctca gagatgagca gccccaccc ccaggcctca    15720 cagagatgtt gtgtcagagt taaatccaag agcagatctc agaattctca gtgggacctt   15780
gactttggca attccacatt gcaggcctta gtttacctct caggacccag gaggccatta   15840
acaggagacc tgaggtgccc ttccctcttc tacatcctca tgagttggat ccagtccata   15900
accatagcat ggggccaaat ctcacaagct ctggtctatg tgaggttctg ggccccatga   15960
gtcagaagtc ctagcggacc aaagaacact agtaacgatg gagaaatatc agttaagtat   16020
gaaccctcag agttcatact gcattccttg ggacaaccat tctggggccc ttccaaaaag   16080
cctggtggtg tgctctttcc atgagggcca ggccaaatgt cttcttcctc ttgtccctgt   16140
atctggaaga atgttataat ttggggaaag ttgtcccagg agagcgggtc tggagccata   16200
tgtaagtgac catttatcag tcatagacac ttgctcagca ttctgtatgt acgaactttg   16260
caagatggct cctgttactg tcccaaatta gacaggagga cagaaagacc ccagccttcc   16320
tccatcacat actcttccca gtctagaagg gcaaactggg ctcagagatg gacaggaagg   16380
cccctttgtc ccaagagggc aaagcctgac cccagatcag gacagtagag gttttccaa    16440 tcctctgtca taatggagct caggagggag ggaggctgac attccagagc cagcaagagg   16500
ccttatggag ttttaagctt cctggcttta ggtggttccc atttctttgg gctctgggac   16560
atcaatacac acagtaagaa ggtggatcca tgcaccctac agagtctgtg ttcttgagat   16620
tctaaaatcc gttggctttg agaaatgata tcgtacagtt ctgagtttct gttactacag   16680
catttgaaga ctcaaggggg tctcaatatc catgaggcct gcctaatact caccaagcat   16740
ccaaccttgg gcccctctgg catccaagaa agacagaatc gatagaactt gggttttgca   16800
tggtagccag atggacgtca cctaccacat ccgctagcac ccacatcacc ctacctgggc   16860
ctatccggct acaggataga ctagccactt ctcggaacga aacctgtggg gtagattatc   16920 tgccccttc tcttcctcct tgttgccgat gaagcccaat gcatccggcc gccatgacgt    16980
caatggcaga aaaatctggc caagttcagg ttgtgacaac agggcccaga tgtagacccc   17040
gataggaaaa catattctat gtcccagaaa caacctccat acagcttcta agaaacagtc   17100
aaacaggaac gccccaacag acagtgcagg aagctggctg gccagcccag ccctccaggt   17160
ccctagtacc actagacaga ccatatccaa ttcaggtcct ctttctgaga atgtactgat   17220
gcatcacaca gtcacaccag ttccacaagt atttaaggag gagatttctt ataagttctg   17280
accaaacata aagagcactt caaaagtgac catggtccag ccatatgggt taagccaata   17340
tagtggaaaa ttctactcac caaacctgat ccgcatttgc ttgagctact gtaatgaagt   17400
atcacaaact gggggactta catagcatag aattatcatg ttagcgttct ggaggctata   17460
agaccaagat gaagacgtca gcagggttga ttcctcctgt aagtcctggc ctccttctca   17520
tctctgatgc tttcctttgc tgttctttct tggaggagca tcacctcatg gctgcctgcc   17580
tgcagtcttt cagctcatcg catcacggtt ctaggaagcc agtctcagct tccacagacc   17640
```

```
cagactcctc ttttcatgct aatgttttag cccgtgacac actagtctta atacctaggt    17700
tctcatataa atctctcaac tctgataagc cccagacatg atagcaaaga agatgcaatt    17760
gccttccaaa acccttccgt gcttccccca ggctgttctc agaagctaca tgcccaacac    17820
atgtagtata tagtagaacg gagaatgaca tattcacatg cacacacaaa cacagcaggg    17880
aaaatgtaca tatatatact tcctagagaa aaatgaggca gtatcagcct gaaatggtgg    17940
tttataatcc cagtactcag aatgcagaaa caaggagttc aaggacagcc tgggtatata    18000
aggagttcca gactacaaga aaccctatct aaaagaaaaa ggaggtccca ggccatgaga    18060
agactataga attctgaacc tggctatcct cttaattaaa atcagggtag aattctatag    18120
tcagttcaag atctggttcc ctctctgact ggaagtatag gatcctgaaa aacgaaagcc    18180 acactttaa gggactgtaa ggtagtgagg ctcagcacag ggacctgggt caccatgtag    18240
agctttgaag aggaaatcag aagactgcag tatggctaag ggaagaagtg gacttccaag    18300
cttggcagag attggagcta gtttgaggag cgcccaggga ccctcaatca agcaacccta    18360
tccctctttt tttcctggca cctgccacgc caattccaag acagaagaaa gcttagagaa    18420
gacagaccca tgctgtggcc ctgagctctg cagtactgaa ttcagctgca agtcttccct    18480
gcctctactg cttacctttg catttagcca catctgacta tcactgtata ctctgctcct    18540
ccatcctcta ccctccatct ccagtaatgc tcctgttgta gctgcttctg ccaaaaacct    18600
agacatcatc ttgacccttt ctctcatctc ctccatccaa gctcccggca acttctcctg    18660
actctgcctt cagacgagac ttggaagaca gtcacatctc agcagctcct ctgccgttat    18720
ccaggttggt agcagcaaca ccactcgcct cactattgca gtacacttcc cactagcaca    18780
gttccctgga gccttcctgc tcacagcatc caactgaatc ttgtgaggct atgcccaagt    18840
cattggaata aaaagatgag aagagagtcc aagacaagcc ccagtagaat cagcaaagac    18900
tatgtggcct gcacagagtg caggggggtac tggagggtcc cacaaaccaa ctccccatca    18960
ccccacattc acgacagagt ggtatggtgt atgtaagcaa gtgaggtgct ggacatgtgc    19020
atgtgtagaa tatatccatc aatctgtgtt cctgctgtca gggtagcata tatgtatgta    19080
agacagacca gaggtgtagt tatgaggcta tcttgcacca cccctggaat gcatgtgact    19140
ccattccact gttatccctg cagcctgcct ctgacaagaa cccaatgccc aaccctaggc    19200
cagccaagcc tatggctcct tccttggccc ttggcccatc cccaggagtc ttgccaagct    19260
ggaagactgc acccaagggc tcagaacttc tagggaccag gggctctggg ggacccttcc    19320
aaggtcggga cctgcgaagt ggggcccaca cctcttcttc cttgaacccc ctgccaccat    19380
cccagctgca ggtgaggccc ggggcccaga atggggtaag cagggtgggg tacttgggcc    19440
tataggtgtc gacctttact gtggcatttg ccggggggttg ggggggggtgc tgggaaacag    19500 gaagtggttt atgggtccca ggcaagtctg acttatgcag atattgcagg gccaagaaaa    19560
tccccactct ccaggcttca gagattcaag gctttcccca cccctcccaa tcctcatccc    19620
gataggagac cttatgattc catggacata gccatgtatc ctcatcccac tgtgacgaga    19680
tggctggggc ccaagaaggt aacagtgttg gggccagctc tacccccttga aactgttgga    19740 ccttgataca ttcactctcc acgagcctca gattccactg atgtgaactg gatagttcca    19800
ttgttgctac cgtgtgagac tttagtaaag agctaatgaa tgagcacag aactattaag    19860 atgaggctca tggcatctca tggcatctcc cttctctctc cagctgccta cagtgcccct    19920
agtcatggtg gcaccgtctg gggcccgact aggtccctca ccccacctac aggcccttct    19980
ccaggacaga ccacacttca tgcatcaggt atggaatcgg agcaggctgg gaggagggaa    20040
```

```
caaagaggac agctgtggag cagagcccca agcccgctg agccatggtc catgtgttcc   20100
ccagctctcc actgtggatg cccatgccca gaccctgtg ctccaagtgc gtccactgga   20160
caacccagcc atgatcagcc tcccaccacc ttctgctgcc actggggtct tctccctcaa   20220
ggcccggcct ggcctgccac ctggtaacac cttcacagta tctccaagtt ctctaatctt   20280
tgagcatgtg caatgtaaac ttttctgaat tatagcccta tggaggtata aagggtctt   20340 aagagtcacg gaaactccaa cctccaaaaa aaaaatatc agacttagaa ccttgaagac   20400
atagaatgca aaaaaaacca caaatcgcta ttatcagtca aaatgccatc acttaccaat   20460
gggcatcttt aggctgttat gtcagaagcc cttgactgtg gaacagcag agtactatga   20520 gacagagtct tcaaggctca ggaaggggag gggccttctg gaacaagctg tagagtctaa   20580
cctgcagctc cagaagtacc ctgtctctac ccacagggat caatgtggcc agtctggaat   20640
gggtgtccag ggagccagct ctactctgca ccttcccacg ctcgggtaca cccaggaaag   20700
acaggtgagt tggcagggct ggcaagaaac ggccctgcc cacacctcac cccaccctg    20760 cacctattcc tctgctgaca tcccatattc tcccatcccc agcaacctt tggctgcacc   20820 ccaaggatcc tacccactgc tggcaaatgg agtctgcaag tggcctggtt gtgagaaggt   20880
cttcgaggag ccagaagagt ttctcaagtg agtagcctga ccctacccac agagttctgc   20940
tgtctaggct tcacgtctca actcaccatc ctctcaatgg atgataataa gaatcataaa   21000
gattcagact ccatccctcc ctggctctgt gatcttgggc aagttatggg tctctaggcc   21060
cagtttacct cgcatgtatg aagagacata ataataaagg tatgtgctca tagttacctt   21120
cctgttacac gcagaaggat ctaaggccac agagaattaa gggtcaatca agctcacaca   21180
ggacctaagt gatgaatctt gaatatgaac acaggcagcc aggttccaga gcccacacgc   21240
ctaactgctt tgtcccgctt cccctcacac aaaacacatt cctgatcctc caatttctgt   21300
tcctctagat gactatagag ctcttgcctc tctgctctct atctgctgtc cctcccttc    21360 tgtatcttgc tagtcacccc taactttgg caatggtgcg tgtttgcgtg gccaggcctt   21420
tgcatgggct gtgcctgaca cctgaaatgc cataccctg catacctcct gtctaacgtc   21480
atcccagcat tttggccaga ctcaaagggt aaataagctc aggcctggca gcccagagtt   21540
gctgaagcac atgtgtttaa ggcaagcaag ggggtgggg ggggagcact gagcatagag   21600
aaatctccca aagggtctag gccgtcccta actgatacac taagccaaga ggcctgaccc   21660
accatggtca gctacatgga atcttctcct tactcaggca ctgccaagca gatcatctcc   21720
tggatgagaa aggcaaggcc cagtgcctcc tccagagaga agtggtgcag tctctggagc   21780
agcaggtaat gcctgcaggg tgtggctgcg gggtgtggct gcgggaaaga aggatgggag   21840
ggaggaccct gtgagggaag gcatgggcaa aagtgtgcct gagaacgacc aggtggaagc   21900
cccactttgg tgtacatccc cacagctgga gctggaaaag gagaagctgg gagctatgca   21960
ggcccacctg gctgggaaga tggcgctggc caaggctcca tctgtggtga gtaccccaag   22020
tccagaggca gcagacttca actgctgagg ggcaagacag gagcccataa ggaccaaatg   22080
tcttcttctc acatgcaagc cctgcccgtg cagaccatt cccacctaat taatatgcca    22140
gatccaaaga cacgcctact ctgcttacaa accttctgac ctccaaaaca ttatgattct   22200
gccttttcag ggcacataca gaaggcagtg aactcacagg gccactgcaa aaaaggaaaa   22260
tggagggcct tatgttcaaa tttcaagata agctcagaac atcgaacagt gtgtgaccac   22320
acatttcaca tacccagtct caggctgata tgagtcttat actataacag aggtagctac   22380
caccatcatc ctaatgcaca aatgaggaca acttaggtca ggaagattta gttgatgctc   22440
```

```
ccaggttcac agttggtgct aggggattcc aattctgccc ctgctcaccc cagccctagc   22500
atctatggct tcatcgcatg ctcatgcctg tactctaaga tgctgcttta cagagctcca   22560
ccagagcctg caattgacta tagggtggtg cccttctcaa aagcattgac cttactggac   22620
acagtggcat gcacctgtag tcctggctac tggagaggct gaaggaggag cacttgaacc   22680
ctcaagttca aaaccagcct ggtcaacaca gagacaccct gactcttcta aaacacaaag   22740
aaacacggtt ggggagaaac ttgagaggga aaagtgattg ccatacaagg ataaggacct   22800
gagttttgct gggtggtggt ggcggcggcg catgcctttg atcccagcac ttgggaggca   22860
gaggcaggtg gatctctgtg agttggaagc cagcctggtc tataaagcta gttccagaac   22920
agccagagct acacggagaa accctgtctt gaacacctct gacagaaaaa ggacctgagt   22980
ttagatgcca gcaccacac cagatgcagc actgtaaatc tgtaatccca gcatgtgtac   23040
acacaccaca catacaaatc agatagaaat atgaccaaat caggaaatgc aaattgtaaa   23100
ataaagtggg gttggggaac tggacagata gctcagggat taagagagct tgctgctctt   23160
tcaggggacc agagtttggt tcccagcacc ctcagagccg ctcacagcta tctctaactc   23220
cagttccagt ggatccaatg cacttttctg ccttccacag gtaccaggca cacatgcgat   23280
gcccagacat gcatgcaggc aaaactcccg tatacctaaa ataaaatgca agctgacttg   23340
gcagtaatct cagcccatcc tgtgctacat agtacatgtt agactagcct gtactacatg   23400
ctacatagta catgttagac tagcctgtac tacatgctac atagtacatg ttagactagc   23460
ctgtactaca gagcaagagc ccacctacat aaatatccaa ccaagcaagc aatcattttt   23520
taaagtaaaa tggaagactc agtgtggtgg cgcacgcacg cctttaatcc tagaactcgg   23580
gaggcagatg caggcagatc tctgtgagtt cgaagccagt ctggtctaca gagcctggtc   23640
tatacactga gctccaggac agccaagact acacagagaa accctgtctg gaagaaaaaa   23700
aaaatatata tatatatata tatatatata cataaaataa aaagtggaag ccagatgtgg   23760
tggcacacac ttataatcct agcactccag aggtagaact aggctagaag gtgcaaggcc   23820
aactagagat atatagtgag actgtctcag acaaaacgaa aatgaatagg caaacactca   23880
ggaggcagag gaagtgcatc tctgagagct gcaggccagt cagggctaca tagtaagacc   23940
ctgtcaataa taataataat ggcaataata atttttaagac caaaataaat agacatggat   24000 gaaggggga aagaatgaga agaaggaaga tcagcgatga gggaggagat acgctgaaat   24060
tggtctgtat gtagtacata catgtcacaa aattgtctgg aacacaagtt taactcataa   24120
gcaaatacac actaatgttt gaaaggctac atggcaatga caagcttaag tgtctcgatt   24180
accacacccc tcccaacccc tcaggcctca atggacaaga gctcttgctg catcgtagcc   24240
accagtactc agggcagtgt gctcccggcc tggtctgctc ctcgggaggc tccagacggc   24300
ggcctgtttg cagtgcggag gcacctctgg ggaagccatg gcaatagttc cttcccaggt   24360
cagtggagtc cacaccccag tgccagggg tacaaaggag ctcccccacc cccctcaccc   24420
ccactaagag ctgggaggaa actgcacctg agtttattag gcttagaagc cctcaactgt   24480
tataaatgca tagccttggg ccccgtgttt tggggattg gagccaggcc tgacctattt   24540
ggcatctgct acttcattca gtcaccatga gggaggagcc tggccaagtg agtccaaaga   24600
gccctctctt ccgtccccac ctccaggaag tcaggtgcac tcaaccaagc taaccaaccc   24660
tctcccacct gtcaggcctg ggttgtgagt ttaccaggga ccatagatat ttggtgtcag   24720
gctggctatg ccacttgagc tgcttacatg cctttgatgt acaaattact tgactccttt   24780
ttaaagtgag gagagctatt tggcaggagt actgcaaaga agacacagct tacggcgggt   24840
```

```
actcagtaaa cagtactatg tgtgagcata gactgtccct ccccccttgg tgctagtggt   24900
aggaattgag accttggatt cctgatgcag acaaaggtgg ggtaggggt gaggaggcca    24960 aaggctctga tctatgccaa ccttctgcag agttcttcca caacatggac tacttcaagt   25020
accacaatat gcgacccct ttcacctatg ccacccttat ccgatgggta agcagggcaa    25080
tagaggccca gcagctggtg ggcggcaggg ggggagttgt ggtggggagt gcttgcctcc   25140
tacattgcac caagagcaga attcacccat taacaaacct cagctctgag gagccccaag   25200
atgtgatcct tcttgatagc ttcacctcag atctagccct caacccaaaa ctactgcaag   25260
ccaggtcagt gcaaagcaaa ctgtaacact acaaactacc cttccttttg tccaccctat   25320
ctctaacatc accttgacc tcatgcctca ccctattctt tctccttccc cttgacccac     25380
aattacaaag ctatcatagc tcagagggcc gagagtaggc tgctccctca gccacaaccc    25440
tgaggaacat gccccttatt ccacctgact ccaacttcca ggccatcctg gaagcccgg    25500 agaggcagag gacactcaat gaaatctacc attggtttac tcgcatgttc gcctacttca   25560
gaaaccaccc cgccacctgg aaggtgagtt cctctgtaca cactggcagc tgggatggct   25620
ccaaggatgg ttagcctggg gctagacatg tgggaagga gcaggtcagt ctcagactca    25680
ggatgactgt caaccctgtc cctgactggg gtcccggtcc cccttccaca gaatgccatc   25740
cgccacaacc tgagcctgca caagtgcttt gtgcgagtgg agagcgagaa gggagcagtg   25800
tggaccgtag atgaatttga gtttcgcaag aagaggagcc aacgcccaa caagtgctcc     25860 aatccctgcc cttgacctca aaccaagaa aaggtgggcg gggagggg ccaaaaccat        25920 gagactgagg ctgtgggggc aaggaggcaa gtcctacgtg tacctatgga aaccgggcga   25980
tgatgtgcct gctatcaggg cctctgctcc ctatctagct gccctcctag atcatatcat   26040
ctgccttaca gctgagaggg gtgccaatcc cagcctagcc cctagttcca acctagcccc   26100
aagatgaact ttccagtcaa agagccctca caaccagcta tacatatctg ccttggccac   26160
tgccaagcag aaagatgaca gacaccatcc taatatttac tcaacccaaa ccctaaaaca   26220
tgaagagcct gccttggtac attcgtgaac tttcaaagtt agtcatgcag tcacacatga   26280
ctgcagtcct actgactcac accccaaagc actcacccac aacatctgga accacgggca   26340
ctatcacaca taggtgtata tacagaccct tacacagcaa cagcactgga accttcacaa   26400
ttacatcccc ccaaaccaca caggcataac tgatcatacg cagcctcaag caatgcccaa   26460
aatacaagtc agacacagct tgtcagaaca cgctcgtgtg cacgtacaca catgcagccc   26520
ctccactcta tctcctgagt tccatgaata cacaccgact ctccaagatg taccccacgt   26580
ctcacttgcc actgaccca gttccctacc cacaagcccc aatccatgcc taagcgtggc    26640
ccacagaaga acttctcttt tatttgggat ccaaggcccc tggccccag tgcccatcca    26700 ataaactgtg gtcagctgga caatcaccct gatcagatat gggaacatat aagcagacag   26760
ctgggtttaa gatcccagca ggagaaagcg gataccaaat gaaagagagt gctagaacag   26820
gtgcctcagc actgtctcca gcaccccaaa ttcctgcctg tggttaggag acatccatca   26880
gggctctagg cctctcggac ccggcccaag aggccagcat tctcctggcg aagggctcgg   26940
tagtcctcac agatcttctc caggttgctc aaagtcttct tgcccatctc tgtctcaatc   27000
taagaaaaca ggatgcacac ttcttcagcc cctgcaggct gccctctac tgaactcctc     27060 cctgctcctc ctattcccgt aacagcagcc tgttccttcc catcactggg cttctgggta   27120
tgtccttccc tccactccac ctaaagcagc aacttctgcc atgggctctg ggaggcatta   27180
ggagccgcaa gctaaaagcc agggctcaga gtaggctact ggctagcttc aggtcccagg   27240
```

```
cacagtgggc acgaaggcaa agcctctagc tgttagttgt ctggtttcaa agactctcag  27300
cgcaaaacaa ggaactatcc cctggcctgt ctccattccc cttaccagtc ccaggtctca  27360
cctgctcctc aagatctcga acttccctca tgatagtgcc tgtgtcctca atggtctgga  27420
tgagctgact gcaattctgg agacagcaag aatacaaggc ttgcacctat gctggccctc  27480
tccagccaac ccaccaggca catggctccc ctcacctcat gcagggcagc taggtacttg  27540 taggcttttcc gaacagcatc atccttctta gcatcctgat aagacaaagg ggatctccga  27600
gatatcagca agccattccc ccttttccac tactctatgc ccctataaga ccacccttta  27660
ctagtacttt gccttcatcc tccacagagc aaagctaggc cccaagcaac agtgcaccta  27720
aaggactcac agaggggcag gcaacaactc agtcccgcct ccaccctccc ggaggccagc  27780
ctgctccata ccttgaacac aagctcatca gtcactgcaa atgtccggtc gagcttccca  27840
gagagagagt tgatttcctt ctgcagttcc tttgtgtccg acaagatctg gtagaaacca  27900
gggtaactat cagtgcacat cttgggcaag gtagctgatc agtgataaca ctcacgtgcc  27960
tatacttaca tccagtcagg gcccatgtcg ctgtgttggg gtgactatta tgtgttggag  28020
tgtgcctgaa cagctctgcc tagtagtgag cataaagtcc ctgtgtgatc accctatgc  28080 ttgtctgcct acatgagcca tcaatcagag ccacagtgac atcataccttt agtgatctct  28140 tccttctgct tccggatgtt gcccacaatc tccaggatgc gctgagtata ggccagccgg  28200
gacacatctt ttggcagagt ctccagctct gacacctagg tgggaacatg gcaggcgtga  28260
gcccaagccc tataccacaa ccacccttac aacccagggc cctaaagtag gccttaccag  28320
ctgcttatag acctcctcct tccggcgagc ctcctctgca gctgctcgaa cactgtggtg  28380
cagctcctgg atttctgcca gccgtcgaga cgattccagc tagcaggaac ccataggcag  28440
aaggcagtga gcagagctca gaaacagccc cctccctcag cccccctccct atctatcagg  28500 gcagtccatc tacactcagc ccactgtgcc acttacctcc ctacagtcct ggagtcttct  28560
gaggtggcgg tactcagcaa gaagtgggac ccggtgtttc tcccactggc ttgctagatg  28620
gatgagcctc tgagcgctgc tctccaccac aagctggcag gagtcaagga tatgtcaaga  28680
tgggctggat ccatctaccc accccctctca gcccaacccc aaaccccagc ccacctgcag  28740
tttggcgagg ttggcagccc catcaggcag caattccacc gtcctgctct tcaggcgcag  28800
ggcctgctcc tgctcggcca cactgagttc actttgtcgg cactcggttt ccacctggta  28860
cactcacagc caagctccca gtcatacaca cagcccacga tcccagtgag cccattatgg  28920
ccctggccca gctcaagacc tcagagaact ccaaggcccc tacctactac aggctttggc  28980
atcttcagct ctgtactgac agccagaggc tctgagaagc cctgtaaggc cctgccccta  29040
cacatcctcc ttgatcccct gatgcccata gctcctatgt tccctacaa agcctgactg  29100 atgccagacc tataggccta tatagtctat atagacctat agtctagcaa gccatcaacc  29160
ctacatgttt ctttgcataa gttctcctta gccttcaaca ataccaaagg tctctaggat  29220
gctccataaa cgattatggc atctatagat ctctagatgt cagatcatct ctcaaggccc  29280
cagttctgac ctggtccagc ccaagtccct ctctaagccc ctcacctgca caaggttgat  29340
tcccagggtc ttcatgtcag cttcaacctc ttcaatgttg tggttcacac tcgccagctg  29400
ctcacgaagg gactctaact cctgctcttg agctgcccgt gtgtcctgag aaacacacgc  29460
cagtctaggt ggagctacca agtccagaag acaggcaata gcccagctga ctctatgtgt  29520
gtgtctgtct gtctgtctgt ctgtctgtct tggtctcctt acctgttcaa gcctttgaga  29580
ggtagctggt acatctgcca cctgagctgc ctggacctgg ggctcctatg ggtagaaaaa  29640
```

```
gcaacctgac tatcacacaa agttctatcc ctcccaggcc agcctcaaac ccccaaagca    29700
ccctcaagca ctgtacccat gtccactcaa ccactgacag ttttcagatt gttactacaa    29760
gagaataaag tgccatctgt aactgctgat tagagtgcct gaccacaagg aaacctccct    29820
gacaaccccg accctataac ctcatgattc tatacccacc ctgaccatcc tgactctaca    29880
actaccatga cactataacc acctgaccat ctggacccta tatccaccct gaccctacaa    29940
cctcttcatg attctatacc cacccctgacc accctgacct tacaaccgcc atgaccctat    30000
aatcacctga ccacccggac cctatgtcca ccctgaccct ataactactc tgactccata    30060
acgaccttgc ccaaaatgtc cacaagaaag atgagtgtct aaggagaaaa gatgtttcca    30120
aagggaaaaa atttccaaag gaaagcccaa ggaaagatgg actttgtact aggagcactt    30180
cacactctta cacaagtccc acctatctgc ctttcctcca ctaaagtctc aagaagctag    30240
gggagccatc tagacaccct gtcctagttg gagaggacct actcagtggg caccagatcc    30300
tctgtcagta acagtggtat ttataaagaa agcaatccgg acacgccctg tccactctag    30360
cctacccacc agatggaagg taaacttctc tgaatgggtg aagcgggagc ctttgggcac    30420
accagtcata gccctagcac cccaggtctg cagcatctct cctaggtctc ggacttgtgt    30480
cggggctcca agtgggcccc agctttgacg cagatgttca atcagctgct tgtgcagtct    30540
ctgctgtgga gcccgggaat cctcctggaa aggacagagg gcaagaggaa ggcatacctg    30600
ctggtcccta gggctggaac ttcccaccac tgtaggtccc agccctggcc taggagtgcc    30660
ctctctccac agctgcactt ctctacccag tcacccctga ccctggggaa gaaagtgact    30720
agagaggaaa ctgagcctgg agctttcaaa ttagaaagag acagaaagat atggacagca    30780
tagacacagg aaaaaaaaag taccaggcca aaaaaaatct agagttgggg acaggaagat    30840
aaagaaatta gagttaac                                                 30858

<210> SEQ ID NO 15
<211> LENGTH: 1869
<212> TYPE: DNA
<213> ORGANISM: Homo sapiens

<400> SEQUENCE: 15
gcacacactc atcgaaaaaa atttggatta ttagaagaga gaggtctgcg gcttccacac      60
cgtacagcgt ggttttctt ctcggtataa agcaaagtt gttttgata cgtgacagtt       120 tcccacaagc caggctgatc ctttctgtc agtccacttc accaagcctg cccttggaca      180
aggacccgat gccaacccc aggcctgca agccctcggc ccttccttg gcccttggcc        240 catccccagg agcctcgccc agctggaggg ctgcacccaa agcctcagac tgctgggggg     300
cccggggccc aggggaacc ttccaggcc gagatcttcg aggcggggcc catgcctcct      360
cttcttcctt gaaccccatg ccaccatcgc agctgcagct gcccacactg ccctagtca     420 tggtggcacc ctccggggca cggctgggcc ccttgcccca cttacaggca ctcctccagg     480
acaggccaca tttcatgcac cagctctcaa cggtggatgc ccacgcccgg accctgtgc      540 tgcaggtgca cccctggag agcccagcca tgatcagcct cacaccaccc accaccgcca     600 ctgggtctt ctccctcaag gccggcctg gcctcccacc tgggatcaac gtggccagcc      660
tggaatgggt gtcagggag ccggcactgc tctgcacctt cccaaatccc agtgcaccca     720
ggaaggacag caccctttcg gctgtgcccc agagctccta cccactgctg gcaaatggtg     780
tctgcaagtg gccggatgt gagaaggtct tcgaagagcc agaggactcc ctcaagcact     840
gccaggcgga ccatcttctg gatgagaagg gcagggcaca atgtctcctc cagagagaga     900
```

```
tggtacagtc tctggagcag cagctggtgc tggagaagga gaagctgagt gccatgcagg      960
cccacctggc tgggaaaatg gcactgacca aggcttcatc tgtggcatca tccgacaagg     1020
gctcctgctg catcgtagct gctggcagcc aaggccctgt cgtcccagcc tggtctggcc     1080
cccgggaggc ccctgacagc ctgtttgctg tccggaggca cctgtggggt agccatggaa     1140
acagcacatt cccagagttc ctccacaaca tggactactt caagttccac aacatgcgac     1200
cccctttcac ctacgccacg ctcatccgct gggccatcct ggaggctcca gagaagcagc     1260
ggacactcaa tgagatctac cactggttca cacgcatgtt tgccttcttc agaaaccatc     1320
ctgccacctg gaagaacgcc atccgccaca acctgagtct gcacaagtgc tttgtgcggg     1380
tggagagcga agggggct gtgtggaccg tggatgagct ggagttccgc aagaaacgga      1440
gccagaggcc cagcaggtgt ccaaccccta cacctggccc ctgacctcaa gatcaaggaa     1500
aggaggatgg acgaacaggg gccaaactgg tgggaggcag aggtggtggg ggcagggatg     1560
ataggccctg gatgtgccca cagggaccaa gaagtgaggt ttccactgtc ttgcctgcca     1620
gggcccctgt tccccgctg gcagccaccc cctcccccat catatccttt gccccaaggc      1680
tgctcagagg ggccccggtc ctggcccag ccccacctc cgcccagac acacccccca       1740
gtcgagccct gcagccaaac agagccttca caaccagcca cacagagcct gcctcagctg     1800
ctcgcacaga ttacttcagg gctggaaaag tcacacagac acacaaaatg tcacaatcct     1860
gtccctcac                                                            1869

<210> SEQ ID NO 16
<211> LENGTH: 3739
<212> TYPE: DNA
<213> ORGANISM: Mus musculus

<400> SEQUENCE: 16
gctgatcccc ctctagcagt ccacttcacc aaggtgagcg agtgtccctg ctctccccca      60
ccagacacag ctctgctggc gaaagtggca gagaggtatt gagggtgggt gtcaggagcc     120
caccagtaca gctggaaaca cccagccact ccagctcccg gcaacttctc ctgactctgc     180
cttcagacga gacttggaag acagtcacat ctcagcagct cctctgccgt tatccagcct     240
gcctctgaca agaacccaat gcccaaccct aggccagcca agcctatggc tccttccttg     300
gcccttggcc catccccagg agtcttgcca agctggaaga ctgcacccaa gggctcagaa     360
cttctaggga ccaggggctc tgggggaccc ttccaaggtc gggacctgcg aagtggggcc     420
cacacctctt cttccttgaa cccctgcca ccatcccagc tgcagctgcc tacagtgccc      480
ctagtcatgg tggcaccgtc tggggcccga ctaggtccct caccccacct acaggccctt     540
ctccaggaca gaccacactt catgcatcag ctctccactg tggatgccca tgcccagacc     600
cctgtgctcc aagtgcgtcc actggacaac ccagccatga tcagcctccc accaccttct     660
gctgccactg ggtcttctc cctcaaggcc cggcctggcc tgccacctgg gatcaatgtg      720
gccagtctgg aatgggtgtc cagggagcca gctctactct gcaccttccc acgctcgggt     780
acacccagga aagacagcaa ccttttggct gcacccaag gatcctaccc actgctggca      840
aatggagtct gcaagtggcc tggttgtgag aaggtcttcg aggagccaga agagtttctc     900
aagcactgcc aagcagatca tctcctggat gagaaaggca aggcccagtg cctcctccag     960
agagaagtgg tgcagtctct ggagcagcag ctggagctgg aaaaggagaa gctgggagct    1020
atgcaggccc acctgctgg gaagatgcg ctggccaagg ctccatctgt ggcctcaatg      1080
gacaagagct cttgctgcat cgtagccacc agtactcagg gcagtgtgct cccggcctgg    1140
```

```
tctgctcctc gggaggctcc agacggcggc ctgtttgcag tgcggaggca cctctgggga    1200
agccatggca atagttcctt cccagagttc ttccacaaca tggactactt caagtaccac    1260
aatatgcgac ccccttttcac ctatgccacc cttatccgat gggccatcct ggaagccccg   1320
gagaggcaga ggacactcaa tgaaatctac cattggttta ctcgcatgtt cgcctacttc    1380
agaaaccacc ccgccacctg gaagaatgcc atccgccaca acctgagcct gcacaagtgc    1440
tttgtgcgag tggagagcga aagggagca gtgtggaccg tagatgaatt tgagtttcgc     1500
aagaagagga gccaacgccc caacaagtgc tccaatccct gcccttgacc tcaaaaccaa    1560
gaaaaggtgg gcggggagg gggccaaaac catgagactg aggctgtggg ggcaaggagg     1620
caagtcctac gtgtacctat ggaaaccggg cgatgatgtg cctgctatca gggcctctgc    1680
tccctatcta gctgccctcc tagatcatat catctgcctt acagctgaga ggggtgccaa    1740
tcccagccta gccctagtt ccaacctagc cccaagatga actttccagt caaagagccc     1800
tcacaaccag ctatacatat ctgccttggc cactgccaag cagaaagatg acagacacca    1860
tcctaatatt tactcaaccc aaaccctaaa acatgaagag cctgccttgg tacattcgtg    1920
aactttcaaa gttagtcatg cagtcacaca tgactgcagt cctactgact cacaccccaa    1980
agcactcacc cacaacatct ggaaccacgg gcactatcac acataggtgt atatacagac    2040
ccttacacag caacagcact ggaaccttca caattcatc ccccaaacc acacaggcat      2100 aactgatcat acgcagcctc aagcaatgcc caaaatacaa gtcagacaca gcttgtcaga   2160
acacgctcgt gtgcacgtac acacatgcag cccctccact ctatctcctg agttccatga    2220
atacacaccg actctccaag atgtacccca cgtctcactt gccactgacc ccagttccct    2280
acccacaagc cccaatccat gcctaagcgt ggcccacaga agaacttctc ttttatttgg    2340
gatccaaggc ccctggcccc cagtgcccat ccaataaact gtggtcagct ggacaatcac    2400
cctgatcaga tatgggaaca tataagcaga cagctgggtt taagatccca gcaggagaaa    2460
gcggatacca aatgaaagag agtgctagaa caggtgcctc agcactgtct ccagcacccc    2520
aaattcctgc ctgtggttag gagacatcca tcagggctct aggcctctcg gacccggccc    2580
aagaggccag cattctcctg gcgaagggct cggtagtcct cacagatctt ctccaggttg    2640
ctcaaagtct tcttgcccat ctctgtctca atctaagaaa acaggatgca cacttcttca    2700
gcccctgcag gctgccctc tactgaactc ctccctgctc ctcctattcc cgtaacagca     2760
gcctgttcct tcccatcact gggcttctgg gtatgtcctt ccctccactc cacctaaagc    2820
agcaacttct gccatgggct ctgggaggca ttaggagccg caagctaaaa gccagggctc    2880
agagtaggct actggctagc ttcaggtccc aggcacagtg ggcacgaagg caaagcctct    2940
agctgttagt tgtctggttt caaagactct cagcgcaaaa caaggaacta tcccctggcc    3000
tgtctccatt ccccttacca gtcccaggtc tcacctgctc ctcaagatct cgaacttccc    3060
tcatgatagt gcctgtgtcc tcaatggtct ggatgagctg actgcaattc tggagacagc    3120
aagaatacaa ggcttgcacc tatgctggcc ctctccagcc aacccaccag gcacatggct    3180
cccctcacct catgcagggc agctaggtac ttgtaggctt tccgaacagc atcatccttc    3240
ttagcatcct gataagacaa aggggatctc cgagatatca gcaagccatt ccccctttc     3300 cactactcta tgcccctata agaccaccct ttactagtac tttgccttca tcctccacag    3360
agcaaagcta ggcccaagc aacagtgcac ctaaaggact cacagagggg caggcaacaa     3420
ctcagtcccg cctccaccct cccggaggcc agcctgctcc atccttgaa cacaagctca     3480 tcagtcactg caaatgtccg gtcgagcttc ccagagagag agttgatttc cttctgcagt    3540
```

| | |
|---|---|
| tcctttgtgt ccgacaagat ctggtagaaa ccagggtaac tatcagtgca catcttgggc | 3600 |
| aaggtagctg atcagtgata acactcacgt gcctatactt acatccagtc agggcccatg | 3660 |
| tcgctgtgtt ggggtgacta ttatgtgttg gagtgtgcct gaacagctct gcctagtagt | 3720 |
| gagcataaag tccctgtgt | 3739 |

<210> SEQ ID NO 17
<211> LENGTH: 3681
<212> TYPE: DNA
<213> ORGANISM: Mus musculus

<400> SEQUENCE: 17

| | |
|---|---|
| gtgagcagaa tccatgtgca aggagagcag gcagttcagg acgagggtga gctggtctct | 60 |
| gcaggtttag tgctgtggca ctgtgcctgg tatatgctcc cggcaacttc tcctgactct | 120 |
| gccttcagac gagacttgga agacagtcac atctcagcag ctcctctgcc gttatccagc | 180 |
| ctgcctctga caagaaccca atgcccaacc ctaggccagc caagcctatg gctccttcct | 240 |
| tggcccttgg cccatcccca ggagtcttgc caagctggaa gactgcaccc aagggctcag | 300 |
| aacttctagg gaccaggggc tctggggac ccttccaagg tcgggacctg cgaagtgggg | 360 |
| cccacacctc ttcttccttg aaccccctgc caccatccca gctgcagctg cctacagtgc | 420 |
| ccctagtcat ggtggcaccg tctggggccc gactaggtcc ctcacccac ctacaggccc | 480 |
| ttctccagga cagaccacac ttcatgcatc agctctccac tgtggatgcc catgcccaga | 540 |
| cccctgtgct ccaagtgcgt ccactggaca acccagccat gatcagcctc ccaccacctt | 600 |
| ctgctgccac tggggtcttc tccctcaagg cccggcctgg cctgccacct gggatcaatg | 660 |
| tggccagtct ggaatgggtg tccagggagc cagctctact ctgcaccttc ccacgctcgg | 720 |
| gtacacccag gaaagacagc aaccttttgg ctgcacccca aggatcctac ccactgctgg | 780 |
| caaatggagt ctgcaagtgg cctggttgtg agaaggtctt cgaggagcca aaagagtttc | 840 |
| tcaagcactg ccaagcagat catcctcctgg atgagaaagg caaggcccag tgcctcctcc | 900 |
| agagagaagt ggtgcagtct ctggagcagc agctggagct ggaaaaggag aagctgggag | 960 |
| ctatgcaggc ccacctggct gggaagatgg cgctggccaa ggctccatct gtggcctcaa | 1020 |
| tggacaagag ctcttgctgc atcgtagcca ccagtactca gggcagtgtg ctcccggcct | 1080 |
| ggtctgctcc tcgggaggct ccagacgcg gcctgtttgc agtgcggagg cacctctggg | 1140 |
| gaagccatgg caatagttcc ttcccagagt tcttccacaa catggactac ttcaagtacc | 1200 |
| acaatatgcg accccctttc acctatgcca cccttatccg atgggccatc ctggaagccc | 1260 |
| cggagaggca gaggacactc aatgaaatct accattggtt tactcgcatg ttcgcctact | 1320 |
| tcagaaacca ccccgccacc tggaagaatg ccatccgcca caacctgagc ctgcacaagt | 1380 |
| gctttgtgcg agtggagagc gagaagggag cagtgtggac cgtagatgaa tttgagtttc | 1440 |
| gcaagaagag gagccaacgc cccaacaagt gctccaatcc ctgcccttga cctcaaaacc | 1500 |
| aagaaaaggt gggcggggga gggggccaaa accatgagac tgaggctgtg ggggcaagga | 1560 |
| ggcaagtcct acgtgtacct atggaaaccg ggcgatgatg tgcctgctat cagggcctct | 1620 |
| gctccctatc tagctgccct cctagatcat atcatctgcc ttacagctga gaggggtgcc | 1680 |
| aatcccagcc tagcccctag ttccaaccta gccccaagat gaactttcca gtcaaagagc | 1740 |
| cctcacaacc agctatacat atctgccttg gccactgcca agcagaaaga tgacagacac | 1800 |
| catcctaata tttactcaac ccaaacccta aacatgaag agcctgcctt ggtacattcg | 1860 |
| tgaactttca aagttagtca tgcagtcaca catgactgca gtcctactga ctcacacccc | 1920 |

-continued

```
aaagcactca cccacaacat ctggaaccac gggcactatc acacataggt gtatatacag    1980 accettacac agcaacagca ctggaacctt cacaattaca tcccccaaa ccacacaggc    2040 ataactgatc atacgcagcc tcaagcaatg cccaaaatac aagtcagaca cagcttgtca    2100
gaacacgctc gtgtgcacgt acacatgc agcccctcca ctctatctcc tgagttccat    2160
gaatacacac cgactctcca agatgtaccc cacgtctcac ttgccactga ccccagttcc    2220
ctacccacaa gccccaatcc atgcctaagc gtggcccaca gaagaacttc tcttttattt    2280
gggatccaag gcccctggcc cccagtgccc atccaataaa ctgtggtcag ctggacaatc    2340
accctgatca gatatgggaa catataagca gacagctggg tttaagatcc cagcaggaga    2400
aagcggatac caaatgaaag agagtgctag aacaggtgcc tcagcactgt ctccagcacc    2460
ccaaattcct gcctgtggtt aggagacatc catcagggct ctaggcctct cggacccggc    2520
ccaagaggcc agcattctcc tggcgaaggg ctcggtagtc ctcacagatc ttctccaggt    2580
tgctcaaagt cttcttgccc atctctgtct caatctaaga aaacaggatg cacacttctt    2640
cagcccctgc aggctgcccc tctactgaac tcctccctgc tcctcctatt cccgtaacag    2700
cagcctgttc cttcccatca ctgggcttct gggtatgtcc ttccctccac tccacctaaa    2760
gcagcaactt ctgccatggg ctctgggagg cattaggagc cgcaagctaa aagccagggc    2820
tcagagtagg ctactggcta gcttcaggtc ccaggcacag tgggcacgaa ggcaaagcct    2880
ctagctgtta gttgtctggt ttcaaagact ctcagcgcaa acaaggaac tatccctgg    2940 cctgtctcca ttcccttac cagtcccagg tctcacctgc tcctcaagat ctcgaacttc    3000
cctcatgata gtgcctgtgt cctcaatggt ctggatgagc tgactgcaat tctggagaca    3060
gcaagaatac aaggcttgca cctatgctgg ccctctccag ccaacccacc aggcacatgg    3120
ctcccctcac ctcatgcagg gcagctaggt acttgtaggc tttccgaaca gcatcatcct    3180
tcttagcatc ctgataagac aaaggggatc tccgagatat cagcaagcca ttccccttt    3240 tccactactc tatgcccta taagaccacc ctttactagt actttgcctt catcctccac    3300
agagcaaagc taggccccaa gcaacagtgc acctaaagga ctcacagagg ggcaggcaac    3360
aactcagtcc cgcctccacc ctccggagg ccagcctgct ccatacctg aacacaagct    3420 catcagtcac tgcaaatgtc cggtcgagct tcccagagag agagttgatt tccttctgca    3480
gttcctttgt gtccgacaag atctggtaga aaccagggta actatcagtg cacatcttgg    3540
gcaaggtagc tgatcagtga taacactcac gtgcctatac ttacatccag tcagggccca    3600
tgtcgctgtg ttggggtgac tattatgtgt tggagtgtgc ctgaacagct ctgcctagta    3660
gtgagcataa agtccctgtg t                                              3681
```

<210> SEQ ID NO 18
<211> LENGTH: 1269
<212> TYPE: DNA
<213> ORGANISM: Pan troglodytes
<220> FEATURE:
<221> NAME/KEY: misc_feature
<222> LOCATION: (184)..(520)
<223> OTHER INFORMATION: n is a, c, g, or t
<220> FEATURE:
<221> NAME/KEY: misc_feature
<222> LOCATION: (709)..(789)
<223> OTHER INFORMATION: n is a, c, g, or t
<220> FEATURE:
<221> NAME/KEY: misc_feature
<222> LOCATION: (941)..(1047)
<223> OTHER INFORMATION: n is a, c, g, or t

<400> SEQUENCE: 18

```
tcggcccctt ccttggccct tggcccatcc ccaggagcct cgcccagctg gagggctgca      60
cccaaagcct cagacctgct gggggcccgg ggcccagggg gaaccttcca gggccgagat     120
cttcgaggcg gggcccatgc ctcctcttcc tccttgaacc ccatgccacc atcgcagctg     180
cagnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn tttcggctgt gccccagagc     540
tcctacccac tgctggcaaa tggtgtctgc aagtggcctg gatgtgagaa ggtcttcgaa     600
gagccagagg acttcctcaa gcactgccag gcggaccatc ttctggatga aagggcagg      660 gcacaatgtc tcctccagag agagatggta cagtctctgg agcagcagnn nnnnnnnnnn     720
nnnnnnnnnn nnnnnnnnnn nnnnnnnnnn nnnnnnnnnn nnnnnnnnnn nnnnnnnnnn     780
nnnnnnnnng catcatccga caagggctcc tgctgcatcg tagctgctgg cagccaaggc     840
cctgtcgtcc cagcctggtc tggccccggg gaggcccctg acagcctgtt tgctgtccgg     900
aggcacctgt ggggtagcca tggaaacagc acattcccag nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnaca ctcaatgaga tctaccactg gttcacacgc    1080
atgtttgcct tcttcagaaa ccatcctgcc acctggaaga acgccatccg ccacaacctg    1140
agtctgcaca agtgctttgt gcgggtggaa agcgagaagg gggctgtgtg gaccgtggat    1200
gagctggagt tccgcaagaa acggagccag aggcccagca ggtgttccaa ccctacacct    1260
ggcccctga                                                            1269

<210> SEQ ID NO 19
<211> LENGTH: 1296
<212> TYPE: DNA
<213> ORGANISM: Homo sapiens
<220> FEATURE:
<221> NAME/KEY: misc_feature
<222> LOCATION: (211)..(315)
<223> OTHER INFORMATION: n is a, c, g, or t
<220> FEATURE:
<221> NAME/KEY: misc_feature
<222> LOCATION: (455)..(542)
<223> OTHER INFORMATION: n is a, c, g, or t

<400> SEQUENCE: 19
atgcccaacc ccaggcctgg caagccctcg gcccttcct tggcccttgg cccatcccca      60
ggagcctcgc ccagctggag ggctgcaccc aaagcctcag acctgctggg ggcccggggc    120 ccaggggaa ccttcaggg ccgagatctt cgaggcgggg cccatgcctc ctcttcttcc      180
ttgaacccca tgccaccatc gcagctgcag nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnctctc aacggtggat gcccacgccc ggaccctgt gctgcaggtg     360 cacccctgg agagcccagc catgatcagc ctcacaccac ccaccaccgc cactgggtc      420 ttctccctca aggcccggcc tggcctccca cctgnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nncacccttt cggctgtgcc ccagagctcc taccccactgc tggcaaatgg tgtctgcaag   600
```

```
tggcccggat gtgagaaggt cttcgaagag ccagaggact tcctcaagca ctgccaggcg    660
gaccatcttc tggatgagaa gggcagggca caatgtctcc tccagagaga gatggtacag    720
tctctggagc agcagctggt gctggagaag gagaagctga gtgccatgca ggcccacctg    780
gctgggaaaa tggcactgac caaggcttca tctgtggcat catccgacaa gggctcctgc    840
tgcatcgtag ctgctggcag ccaaggccct gtcgtcccag cctggtctgg ccccgggag     900
gcccctgaca gcctgtttgc tgtccggagg cacctgtggg gtagccatgg aaacagcaca    960
ttcccagagt cctccacaa catggactac ttcaagttcc acaacatgcg acccccttc    1020
acctacgcca cgctcatccg ctgggccatc ctggaggctc agagaagca gcggacactc   1080
aatgagatct accactggtt cacacgcatg tttgccttct tcagaaacca tcctgccacc   1140
tggaagaacg ccatccgcca caacctgagt ctgcacaagt gctttgtgcg ggtgagagc   1200
gagaagggg ctgtgtggac cgtggatgag ctggagttcc gcaagaaacg gagccagagg    1260
cccagcaggt gttccaaccc tacacctggc ccctga                             1296
```

<210> SEQ ID NO 20
<211> LENGTH: 431
<212> TYPE: PRT
<213> ORGANISM: Homo sapiens

<400> SEQUENCE: 20

```
Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255
```

-continued

Gln Ala His Leu Ala Gly Lys Met Ala Leu Thr Lys Ala Ser Ser Val
                260                 265                 270

Ala Ser Ser Asp Lys Gly Ser Cys Cys Ile Val Ala Ala Gly Ser Gln
            275                 280                 285

Gly Pro Val Val Pro Ala Trp Ser Gly Pro Arg Glu Ala Pro Asp Ser
290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
                340                 345                 350

Ala Pro Glu Lys Gln Arg Thr Leu Asn Glu Ile Tyr His Trp Phe Thr
            355                 360                 365

Arg Met Phe Ala Phe Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
                420                 425                 430

<210> SEQ ID NO 21
<211> LENGTH: 429
<212> TYPE: PRT
<213> ORGANISM: Mus musculus

<400> SEQUENCE: 21

Met Pro Asn Pro Arg Pro Ala Lys Pro Met Ala Pro Ser Leu Ala Leu
1               5                   10                  15

Gly Pro Ser Pro Gly Val Leu Pro Ser Trp Lys Thr Ala Pro Lys Gly
            20                  25                  30

Ser Glu Leu Leu Gly Thr Arg Gly Ser Gly Pro Phe Gln Gly Arg
                35                  40                  45

Asp Leu Arg Ser Gly Ala His Thr Ser Ser Leu Asn Pro Leu Pro
50                  55                  60

Pro Ser Gln Leu Gln Leu Pro Thr Val Pro Leu Val Met Val Ala Pro
65                  70                  75                  80

Ser Gly Ala Arg Leu Gly Pro Ser Pro His Leu Gln Ala Leu Leu Gln
                85                  90                  95

Asp Arg Pro His Phe Met His Gln Leu Ser Thr Val Asp Ala His Ala
            100                 105                 110

Gln Thr Pro Val Leu Gln Val Arg Pro Leu Asp Asn Pro Ala Met Ile
        115                 120                 125

Ser Leu Pro Pro Pro Ser Ala Ala Thr Gly Val Phe Ser Leu Lys Ala
        130                 135                 140

Arg Pro Gly Leu Pro Pro Gly Ile Asn Val Ala Ser Leu Glu Trp Val
145                 150                 155                 160

Ser Arg Glu Pro Ala Leu Leu Cys Thr Phe Pro Arg Ser Gly Thr Pro
                165                 170                 175

Arg Lys Asp Ser Asn Leu Leu Ala Ala Pro Gln Gly Ser Tyr Pro Leu
            180                 185                 190

Leu Ala Asn Gly Val Cys Lys Trp Pro Gly Cys Glu Lys Val Phe Glu
                195                 200                 205

-continued

Glu Pro Glu Glu Phe Leu Lys His Cys Gln Ala Asp His Leu Leu Asp
    210                 215                 220

Glu Lys Gly Lys Ala Gln Cys Leu Leu Gln Arg Glu Val Val Gln Ser
225                 230                 235                 240

Leu Glu Gln Gln Leu Glu Leu Glu Lys Glu Lys Leu Gly Ala Met Gln
                245                 250                 255

Ala His Leu Ala Gly Lys Met Ala Leu Ala Lys Ala Pro Ser Val Ala
            260                 265                 270

Ser Met Asp Lys Ser Ser Cys Cys Ile Val Ala Thr Ser Thr Gln Gly
        275                 280                 285

Ser Val Leu Pro Ala Trp Ser Ala Pro Arg Glu Ala Pro Asp Gly Gly
    290                 295                 300

Leu Phe Ala Val Arg Arg His Leu Trp Gly Ser His Gly Asn Ser Ser
305                 310                 315                 320

Phe Pro Glu Phe Phe His Asn Met Asp Tyr Phe Lys Tyr His Asn Met
                325                 330                 335

Arg Pro Pro Phe Thr Tyr Ala Thr Leu Ile Arg Trp Ala Ile Leu Glu
            340                 345                 350

Ala Pro Glu Arg Gln Arg Thr Leu Asn Glu Ile Tyr His Trp Phe Thr
        355                 360                 365

Arg Met Phe Ala Tyr Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Phe Glu Phe Arg Lys Lys
                405                 410                 415

Arg Ser Gln Arg Pro Asn Lys Cys Ser Asn Pro Cys Pro
            420                 425

<210> SEQ ID NO 22
<211> LENGTH: 430
<212> TYPE: PRT
<213> ORGANISM: Felis catus
<220> FEATURE:
<221> NAME/KEY: misc_feature
<222> LOCATION: (185)..(185)
<223> OTHER INFORMATION: Xaa can be any naturally occurring amino acid

<400> SEQUENCE: 22

Met Pro Asn Pro Arg Pro Ala Lys Pro Ser Ala Pro Ser Leu Ala Leu
1               5                   10                  15

Gly Pro Ser Pro Gly Ala Ser Pro Ser Trp Arg Ala Gly Pro Lys Thr
            20                  25                  30

Ser Asp Pro Leu Gly Ala Lys Gly Pro Gly Ala Thr Phe Gln Gly Arg
        35                  40                  45

Asp Leu Arg Gly Gly Thr His Ala Ser Ser Leu Asn Pro Met Pro
    50                  55                  60

Pro Ser Gln Leu Gln Leu Pro Thr Val Pro Leu Val Met Val Ala Pro
65                  70                  75                  80

Ser Gly Thr Arg Leu Gly Pro Ser Pro His Leu Gln Ala Leu Leu Gln
                85                  90                  95

Asp Arg Pro His Phe Met His Gln Leu Ser Thr Val Asp Thr His Ala
            100                 105                 110

Arg Thr Pro Val Leu Gln Val Arg Pro Leu Asp Ser Pro Ala Met Ile
        115                 120                 125

Ser Leu Pro Pro Pro Thr Ala Ala Thr Gly Val Phe Ser Leu Lys Ala
    130                 135                 140

```
Arg Pro Gly Leu Pro Pro Gly Ile Asn Val Ala Ser Leu Glu Trp Val
145                 150                 155                 160

Ser Arg Glu Pro Ala Leu Leu Cys Thr Phe Pro Ser Pro Ser Thr Pro
                165                 170                 175

Arg Lys Asp Ser Thr Leu Ser Thr Xaa Pro Gln Gly Ser Tyr Ser Leu
            180                 185                 190

Leu Ala Asn Gly Val Cys Lys Trp Pro Gly Cys Glu Lys Val Phe Glu
        195                 200                 205

Glu Pro Glu Asp Phe Leu Lys His Cys Gln Ala Asp His Leu Leu Asp
    210                 215                 220

Glu Lys Gly Arg Ala Gln Cys Leu Leu Gln Arg Glu Val Val Gln Ser
225                 230                 235                 240

Leu Glu Gln Gln Leu Val Leu Glu Lys Glu Lys Leu Gly Ala Met Gln
                245                 250                 255

Ala His Leu Ala Gly Lys Met Ala Leu Thr Lys Ala Pro Ser Thr Ala
                260                 265                 270

Ser Ser Asp Lys Gly Ser Cys Cys Ile Val Ala Thr Gly Thr Pro Ala
            275                 280                 285

Ala Thr Gly Pro Ala Trp Pro Ser Pro Gln Glu Ala Pro Asp Gly Leu
        290                 295                 300

Phe Ala Val Arg Arg His Leu Trp Gly Ser His Gly Asn Ser Thr Phe
305                 310                 315                 320

Pro Glu Phe Phe His Asn Met Asp Tyr Phe Lys Phe His Asp Met Arg
                325                 330                 335

Pro Pro Phe Thr Tyr Ala Thr Leu Ile Arg Trp Ala Ile Leu Glu Ala
                340                 345                 350

Pro Glu Lys Gln Arg Thr Leu Asn Glu Ile Tyr His Trp Phe Thr Arg
            355                 360                 365

Met Phe Ala Phe Phe Arg Asn His Pro Ala Thr Trp Lys Asn Ala Ile
        370                 375                 380

Arg His Asn Leu Ser Leu His Lys Cys Phe Val Arg Val Glu Ser Glu
385                 390                 395                 400

Lys Gly Ala Val Trp Thr Val Asp Glu Phe Glu Phe Arg Lys Lys Arg
                405                 410                 415

Ser Gln Arg Pro Ser Arg Cys Ser Asn Pro Thr Pro Gly Pro
            420                 425                 430

<210> SEQ ID NO 23
<211> LENGTH: 429
<212> TYPE: PRT
<213> ORGANISM: Mus musculus

<400> SEQUENCE: 23

Met Pro Asn Pro Arg Pro Ala Lys Pro Met Ala Pro Ser Leu Ala Leu
1               5                   10                  15

Gly Pro Ser Pro Gly Val Leu Pro Ser Trp Lys Thr Ala Pro Lys Gly
                20                  25                  30

Ser Glu Leu Leu Gly Thr Arg Gly Ser Gly Pro Phe Gln Gly Arg
            35                  40                  45

Asp Leu Arg Ser Gly Ala His Thr Ser Ser Leu Asn Pro Leu Pro
    50                  55                  60

Pro Ser Gln Leu Gln Leu Pro Thr Val Pro Leu Val Met Val Ala Pro
65                  70                  75                  80

Ser Gly Ala Arg Leu Gly Pro Ser Pro His Leu Gln Ala Leu Leu Gln
                85                  90                  95
```

```
Asp Arg Pro His Phe Met His Gln Leu Ser Thr Val Asp Ala His Ala
            100                 105                 110

Gln Thr Pro Val Leu Gln Val Arg Pro Leu Asp Asn Pro Ala Met Ile
        115                 120                 125

Ser Leu Pro Pro Pro Ser Ala Ala Thr Gly Val Phe Ser Leu Lys Ala
130                 135                 140

Arg Pro Gly Leu Pro Pro Gly Ile Asn Val Ala Ser Leu Glu Trp Val
145                 150                 155                 160

Ser Arg Glu Pro Ala Leu Leu Cys Thr Phe Pro Arg Ser Gly Thr Pro
                165                 170                 175

Arg Lys Asp Ser Asn Leu Leu Ala Ala Pro Gln Gly Ser Tyr Pro Leu
            180                 185                 190

Leu Ala Asn Gly Val Cys Lys Trp Pro Gly Cys Glu Lys Val Phe Glu
        195                 200                 205

Glu Pro Glu Glu Phe Leu Lys His Cys Gln Ala Asp His Leu Leu Asp
210                 215                 220

Glu Lys Gly Lys Ala Gln Cys Leu Leu Gln Arg Glu Val Val Gln Ser
225                 230                 235                 240

Leu Glu Gln Gln Leu Glu Leu Glu Lys Glu Lys Leu Gly Ala Met Gln
                245                 250                 255

Ala His Leu Ala Gly Lys Met Ala Leu Ala Lys Ala Pro Ser Val Ala
            260                 265                 270

Ser Met Asp Lys Ser Ser Cys Cys Ile Val Ala Thr Ser Thr Gln Gly
        275                 280                 285

Ser Val Leu Pro Ala Trp Ser Ala Pro Arg Glu Ala Pro Asp Gly Gly
290                 295                 300

Leu Phe Ala Val Arg Arg His Leu Trp Gly Ser His Gly Asn Ser Ser
305                 310                 315                 320

Phe Pro Glu Phe Phe His Asn Met Asp Tyr Phe Lys Tyr His Asn Met
                325                 330                 335

Arg Pro Pro Phe Thr Tyr Ala Thr Leu Ile Arg Trp Ala Ile Leu Glu
            340                 345                 350

Ala Pro Glu Arg Gln Arg Thr Leu Asn Glu Ile Tyr His Trp Phe Thr
        355                 360                 365

Arg Met Phe Ala Tyr Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Phe Glu Phe Arg Lys Lys
                405                 410                 415

Arg Ser Gln Arg Pro Asn Lys Cys Ser Asn Pro Cys Pro
            420                 425

<210> SEQ ID NO 24
<211> LENGTH: 431
<212> TYPE: PRT
<213> ORGANISM: Bos taurus

<400> SEQUENCE: 24

Met Pro Asn Pro Arg Pro Ala Lys Pro Leu Ala Pro Ser Leu Val Leu
1               5                   10                  15

Ser Pro Ser Pro Gly Ala Ser Pro Ser Trp Arg Ala Ala Pro Lys Ala
            20                  25                  30

Ser Asp Gln Leu Gly Thr Lys Ser Pro Gly Thr Thr Phe Gln Gly Arg
        35                  40                  45
```

```
Asp Leu Arg Ser Gly Ala His Thr Ser Ser Ser Leu Asn Pro Met
 50                  55                  60

Pro Pro Ser Gln Leu Gln Met Pro Thr Val Pro Leu Val Met Val Ala
 65                  70                  75                  80

Pro Ser Gly Ala Arg Leu Gly Pro Ser Pro His Leu Gln Ala Leu Leu
                 85                  90                  95

Gln Asp Arg Pro His Phe Val His Gln Leu Ser Thr Val Asp Ala His
                100                 105                 110

Ala Arg Thr Pro Val Leu Gln Val Arg Pro Leu Asp Ser Pro Ala Met
            115                 120                 125

Ile Ser Leu Pro Pro Thr Ala Ala Thr Gly Leu Phe Ser Leu Lys
130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Ser Pro Gly Met
                165                 170                 175

Pro Arg Lys Asp Ser Thr Leu Ser Thr Val Pro Gln Gly Ser Tyr Ser
                180                 185                 190

Leu Leu Ala Asn Gly Val Cys Lys Trp Pro Gly Cys Glu Lys Val Phe
                195                 200                 205

Lys Glu Pro Glu Asp Phe Leu Lys His Cys Gln Ala Asp His Leu Leu
210                 215                 220

Asp Glu Lys Gly Arg Ala Gln Cys Leu Leu Gln Arg Glu Val Val Gln
225                 230                 235                 240

Ser Leu Glu Gln Gln Leu Val Leu Glu Lys Glu Lys Leu Gly Ala Met
                245                 250                 255

Gln Ala His Leu Ala Gly Lys Met Ala Gln Thr Lys Ala Pro Ser Ala
                260                 265                 270

Ala Ser Ser Asp Lys Gly Ser Cys Cys Ile Val Ala Thr Gly Thr Pro
                275                 280                 285

Gly Thr Thr Val Pro Ala Trp Pro Gly Pro Gln Glu Ala Pro Asp Gly
                290                 295                 300

Leu Phe Ala Val Arg Arg His Leu Trp Gly Ser His Gly Asn Ser Thr
305                 310                 315                 320

Phe Pro Glu Phe Phe His Asn Met Asp Tyr Phe Lys Phe His Asn Met
                325                 330                 335

Arg Pro Pro Phe Thr Tyr Ala Thr Leu Ile Arg Trp Ala Ile Leu Glu
                340                 345                 350

Ala Pro Glu Lys Gln Arg Thr Leu Asn Glu Ile Tyr His Trp Phe Thr
                355                 360                 365

Arg Met Phe Ala Phe Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Val Val Trp Thr Val Asp Glu Phe Glu Phe Arg Lys Lys
                405                 410                 415

Arg Ser Gln Arg Pro Ser Arg Cys Ser Asn Pro Thr Pro Gly Pro
                420                 425                 430
```

<210> SEQ ID NO 25
<211> LENGTH: 431
<212> TYPE: PRT
<213> ORGANISM: Macaca mulatta

<400> SEQUENCE: 25

```
Met Pro Asn Pro Arg Pro Gly Lys Pro Ser Ala Pro Ser Leu Ala Leu
1               5                   10                  15
Gly Pro Ser Pro Gly Ala Ser Pro Ser Trp Arg Ala Ala Pro Lys Ala
            20                  25                  30
Ser Asp Leu Leu Gly Ala Arg Gly Pro Gly Gly Ile Phe Gln Gly Arg
            35                  40                  45
Asp Leu Arg Gly Gly Ala His Ala Ser Ser Ser Leu Asn Pro Met
    50                  55                  60
Pro Pro Ser Gln Leu Gln Leu Pro Thr Leu Pro Leu Val Met Val Ala
65                  70                  75                  80
Pro Ser Gly Ala Arg Leu Gly Pro Leu Pro His Leu Gln Ala Leu Leu
                85                  90                  95
Gln Asp Arg Pro His Phe Met His Gln Leu Ser Thr Val Asp Ala His
            100                 105                 110
Ala Arg Thr Pro Val Leu Gln Val His Pro Leu Glu Ser Pro Ala Met
            115                 120                 125
Ile Ser Leu Pro Pro Pro Thr Thr Ala Thr Gly Val Phe Ser Leu Lys
            130                 135                 140
Ala Arg Pro Gly Leu Pro Pro Gly Ile Asn Val Ala Ser Pro Glu Trp
145                 150                 155                 160
Val Ser Arg Glu Leu Ala Leu Leu Cys Thr Phe Pro Asn Pro Gly Ala
            165                 170                 175
Pro Arg Lys Asp Ser Thr Leu Ser Ala Met Pro Gln Ser Ser Tyr Pro
            180                 185                 190
Leu Leu Ala Asn Gly Val Cys Lys Trp Pro Gly Cys Glu Lys Val Phe
            195                 200                 205
Glu Glu Pro Glu Asp Phe Leu Lys His Cys Gln Ala Asp His Leu Leu
210                 215                 220
Asp Glu Lys Gly Arg Ala Gln Cys Leu Leu Gln Arg Glu Met Val Gln
225                 230                 235                 240
Ser Leu Lys Gln Gln Leu Val Leu Glu Lys Glu Lys Leu Ser Ala Met
            245                 250                 255
Gln Ala His Leu Ala Gly Lys Met Ala Leu Thr Lys Ala Ser Ser Val
            260                 265                 270
Ala Ser Ser Asp Lys Gly Ser Cys Cys Ile Val Ala Ala Gly Ser Gln
            275                 280                 285
Gly Ser Ala Val Pro Ala Trp Ser Gly Pro Arg Glu Ala Pro Asp Ser
290                 295                 300
Leu Phe Ala Val Arg Arg His Leu Trp Gly Ser His Gly Asn Ser Thr
305                 310                 315                 320
Phe Pro Glu Phe Leu His Asn Met Asp Tyr Phe Lys Phe His Asn Met
            325                 330                 335
Arg Pro Pro Phe Thr Tyr Ala Thr Leu Ile Arg Trp Ala Ile Leu Glu
            340                 345                 350
Ala Pro Glu Lys Gln Arg Thr Leu Asn Glu Ile Tyr His Trp Phe Thr
            355                 360                 365
Arg Met Phe Ala Phe Phe Arg Asn His Pro Ala Thr Trp Lys Asn Ala
            370                 375                 380
Ile Arg His Asn Leu Ser Leu His Lys Cys Phe Val Arg Val Glu Ser
385                 390                 395                 400
Glu Lys Gly Ala Val Trp Thr Val Asp Glu Leu Glu Phe Arg Lys Lys
            405                 410                 415
Arg Ser Gln Arg Pro Ser Arg Cys Ser Asn Pro Thr Pro Gly Pro
```

```
                420              425              430
```

<210> SEQ ID NO 26
<211> LENGTH: 431
<212> TYPE: PRT
<213> ORGANISM: Bos taurus

<400> SEQUENCE: 26

```
Met Pro Asn Pro Arg Pro Ala Lys Pro Leu Ala Pro Ser Leu Val Leu
1               5                   10                  15

Ser Pro Ser Pro Gly Ala Ser Pro Ser Trp Arg Ala Ala Pro Lys Ala
            20                  25                  30

Ser Asp Gln Leu Gly Thr Lys Ser Pro Gly Thr Thr Phe Gln Gly Arg
        35                  40                  45

Asp Leu Arg Ser Gly Ala His Thr Ser Ser Ser Leu Asn Pro Met
50                  55                  60

Pro Pro Ser Gln Leu Gln Met Pro Thr Val Pro Leu Val Met Val Ala
65                  70                  75                  80

Pro Ser Gly Ala Arg Leu Gly Pro Ser Pro His Leu Gln Ala Leu Leu
                85                  90                  95

Gln Asp Arg Pro His Phe Val His Gln Leu Ser Thr Val Asp Ala His
            100                 105                 110

Ala Arg Thr Pro Val Leu Gln Val Arg Pro Leu Asp Ser Pro Ala Met
        115                 120                 125

Ile Ser Leu Pro Pro Thr Ala Ala Thr Gly Leu Phe Ser Leu Lys
130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Ser Pro Gly Met
                165                 170                 175

Pro Arg Lys Asp Ser Thr Leu Ser Thr Val Pro Gln Gly Ser Tyr Ser
            180                 185                 190

Leu Leu Ala Asn Gly Val Cys Lys Trp Pro Gly Cys Glu Lys Val Phe
        195                 200                 205

Lys Glu Pro Glu Asp Phe Leu Lys His Cys Gln Ala Asp His Leu Leu
210                 215                 220

Asp Glu Lys Gly Arg Ala Gln Cys Leu Leu Gln Arg Glu Val Val Gln
225                 230                 235                 240

Ser Leu Glu Gln Gln Leu Val Leu Glu Lys Glu Lys Leu Gly Ala Met
                245                 250                 255

Gln Ala His Leu Ala Gly Lys Met Ala Gln Thr Lys Ala Pro Ser Ala
            260                 265                 270

Ala Ser Ser Asp Lys Gly Ser Cys Cys Ile Val Ala Thr Gly Thr Pro
        275                 280                 285

Gly Thr Thr Val Pro Ala Trp Pro Gly Pro Gln Glu Ala Pro Asp Gly
290                 295                 300

Leu Phe Ala Val Arg Arg His Leu Trp Gly Ser His Gly Asn Ser Thr
305                 310                 315                 320

Phe Pro Glu Phe Phe His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
```

-continued

```
                    370                 375                 380
Ile Arg His Asn Leu Ser Leu His Lys Cys Phe Val Arg Val Glu Ser
385                 390                 395                 400

Glu Lys Gly Val Val Trp Thr Val Asp Glu Phe Glu Phe Arg Lys Lys
                    405                 410                 415

Arg Ser Gln Arg Pro Ser Arg Cys Ser Asn Pro Thr Pro Gly Pro
                420                 425                 430

<210> SEQ ID NO 27
<211> LENGTH: 167
<212> TYPE: PRT
<213> ORGANISM: Pan troglodytes

<400> SEQUENCE: 27

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
                20                  25                  30

Ser Asp Leu Leu Gly Ala Arg Gly Pro Gly Gly Thr Phe Gln Gly Arg
            35                  40                  45

Asp Leu Arg Gly Gly Ala His Ala Ser Ser Ser Leu Asn Pro Met
50                  55                  60

Pro Pro Ser Gln Leu Gln Val His Pro Leu Glu Ser Pro Ala Met Ile
65                  70                  75                  80

Ser Leu Pro Pro Pro Thr Thr Ala Thr Gly Val Phe Ser Leu Lys Ala
                85                  90                  95

Arg Pro Gly Leu Pro Pro Gly Ile Asn Val Ala Ser Leu Glu Trp Val
            100                 105                 110

Ser Arg Glu Pro Ala Leu Leu Cys Thr Phe Pro Asn Pro Gly Ala Pro
        115                 120                 125

Arg Lys Asp Ser Thr Leu Ser Ala Val Pro Gln Ser Ser Tyr Pro Leu
    130                 135                 140

Leu Ala Asn Gly Val Cys Lys Trp Pro Gly Cys Glu Lys Val Phe Glu
145                 150                 155                 160

Glu Pro Glu Asp Phe Leu Lys
                165

<210> SEQ ID NO 28
<211> LENGTH: 208
<212> TYPE: PRT
<213> ORGANISM: Peromyscus maniculatus

<400> SEQUENCE: 28

Tyr Pro Leu Leu Ala Asn Gly Val Cys Lys Trp Pro Gly Cys Glu Lys
1               5                   10                  15

Val Phe Glu Glu Pro Glu Glu Phe Leu Lys His Cys Gln Ala Asp His
                20                  25                  30

Leu Leu Asp Glu Lys Gly Lys Ala Gln Cys Leu Leu Gln Arg Glu
            35                  40                  45

Val Val Gln Ser Leu Glu Gln Gln Leu Glu Leu Glu Lys Glu Lys Leu
    50                  55                  60

Gly Ala Met Gln Ala His Leu Ala Gly Lys Met Ala Leu Ser Lys Ala
65                  70                  75                  80

Pro Ala Met Ala Ser Val Asp Lys Ser Ser Cys Cys Ile Val Ala Ala
                85                  90                  95

Ser Ser Gln Gly Ser Val Leu Pro Ala Trp Pro Ala Pro Arg Glu Pro
            100                 105                 110
```

```
Ser Asp Ser Leu Phe Ala Val Arg Arg His Leu Trp Gly Ser His Gly
        115                 120                 125
Asn Gly Thr Phe Pro Glu Phe His Asn Met Asp Tyr Phe Lys Phe
    130                 135                 140
His Asn Met Arg Pro Pro Phe Thr Tyr Ala Thr Leu Ile Arg Trp Ala
145                 150                 155                 160
Ile Leu Glu Ala Pro Glu Lys Gln Arg Thr Leu Asn Glu Ile Tyr His
                165                 170                 175
Trp Phe Thr Arg Met Phe Ala Tyr Phe Arg Asn His Pro Ala Thr Trp
            180                 185                 190
Lys Asn Ala Ile Arg His Asn Leu Ser Ser His Lys Cys Phe Val Arg
        195                 200                 205

<210> SEQ ID NO 29
<211> LENGTH: 396
<212> TYPE: PRT
<213> ORGANISM: Homo sapiens

<400> SEQUENCE: 29

Met Pro Asn Pro Arg Pro Gly Lys Pro Ser Ala Pro Ser Leu Ala Leu
1               5                   10                  15
Gly Pro Ser Pro Gly Ala Ser Pro Ser Trp Arg Ala Ala Pro Lys Ala
            20                  25                  30
Ser Asp Leu Leu Gly Ala Arg Gly Pro Gly Gly Thr Phe Gln Gly Arg
        35                  40                  45
Asp Leu Arg Gly Gly Ala His Ala Ser Ser Ser Leu Asn Pro Met
    50                  55                  60
Pro Pro Ser Gln Leu Gln Leu Ser Thr Val Asp Ala His Ala Arg Thr
65                  70                  75                  80
Pro Val Leu Gln Val His Pro Leu Glu Ser Pro Ala Met Ile Ser Leu
                85                  90                  95
Thr Pro Pro Thr Thr Ala Thr Gly Val Phe Ser Leu Lys Ala Arg Pro
            100                 105                 110
Gly Leu Pro Pro Gly Ile Asn Val Ala Ser Leu Glu Trp Val Ser Arg
        115                 120                 125
Glu Pro Ala Leu Leu Cys Thr Phe Pro Asn Pro Ser Ala Pro Arg Lys
    130                 135                 140
Asp Ser Thr Leu Ser Ala Val Pro Gln Ser Ser Tyr Pro Leu Leu Ala
145                 150                 155                 160
Asn Gly Val Cys Lys Trp Pro Gly Cys Glu Lys Val Phe Glu Glu Pro
                165                 170                 175
Glu Asp Phe Leu Lys His Cys Gln Ala Asp His Leu Leu Asp Glu Lys
            180                 185                 190
Gly Arg Ala Gln Cys Leu Leu Gln Arg Glu Met Val Gln Ser Leu Glu
        195                 200                 205
Gln Gln Leu Val Leu Glu Lys Glu Lys Leu Ser Ala Met Gln Ala His
    210                 215                 220
Leu Ala Gly Lys Met Ala Leu Thr Lys Ala Ser Ser Val Ala Ser Ser
225                 230                 235                 240
Asp Lys Gly Ser Cys Cys Ile Val Ala Ala Gly Ser Gln Gly Pro Val
                245                 250                 255
Val Pro Ala Trp Ser Gly Pro Arg Glu Ala Pro Asp Ser Leu Phe Ala
            260                 265                 270
Val Arg Arg His Leu Trp Gly Ser His Gly Asn Ser Thr Phe Pro Glu
        275                 280                 285
```

```
Phe Leu His Asn Met Asp Tyr Phe Lys Phe His Asn Met Arg Pro Pro
    290                 295                 300

Phe Thr Tyr Ala Thr Leu Ile Arg Trp Ala Ile Leu Glu Ala Pro Glu
305                 310                 315                 320

Lys Gln Arg Thr Leu Asn Glu Ile Tyr His Trp Phe Thr Arg Met Phe
                325                 330                 335

Ala Phe Phe Arg Asn His Pro Ala Thr Trp Lys Asn Ala Ile Arg His
            340                 345                 350

Asn Leu Ser Leu His Lys Cys Phe Val Arg Val Glu Ser Glu Lys Gly
        355                 360                 365

Ala Val Trp Thr Val Asp Glu Leu Glu Phe Arg Lys Lys Arg Ser Gln
    370                 375                 380

Arg Pro Ser Arg Cys Ser Asn Pro Thr Pro Gly Pro
385                 390                 395

<210> SEQ ID NO 30
<211> LENGTH: 429
<212> TYPE: PRT
<213> ORGANISM: Mus musculus

<400> SEQUENCE: 30

Met Pro Asn Pro Arg Pro Ala Lys Pro Met Ala Pro Ser Leu Ala Leu
1               5                   10                  15

Gly Pro Ser Pro Gly Val Leu Pro Ser Trp Lys Thr Ala Pro Lys Gly
            20                  25                  30

Ser Glu Leu Leu Gly Thr Arg Gly Ser Gly Pro Phe Gln Gly Arg
        35                  40                  45

Asp Leu Arg Ser Gly Ala His Thr Ser Ser Ser Leu Asn Pro Leu Pro
50                  55                  60

Pro Ser Gln Leu Gln Leu Pro Thr Val Pro Leu Val Met Val Ala Pro
65                  70                  75                  80

Ser Gly Ala Arg Leu Gly Pro Ser Pro His Leu Gln Ala Leu Leu Gln
                85                  90                  95

Asp Arg Pro His Phe Met His Gln Leu Ser Thr Val Asp Ala His Ala
            100                 105                 110

Gln Thr Pro Val Leu Gln Val Arg Pro Leu Asp Asn Pro Ala Met Ile
        115                 120                 125

Ser Leu Pro Pro Pro Ser Ala Ala Thr Gly Val Phe Ser Leu Lys Ala
    130                 135                 140

Arg Pro Gly Leu Pro Pro Gly Ile Asn Val Ala Ser Leu Glu Trp Val
145                 150                 155                 160

Ser Arg Glu Pro Ala Leu Leu Cys Thr Phe Pro Arg Ser Gly Thr Pro
                165                 170                 175

Arg Lys Asp Ser Asn Leu Leu Ala Ala Pro Gln Gly Ser Tyr Pro Leu
            180                 185                 190

Leu Ala Asn Gly Val Cys Lys Trp Pro Gly Cys Glu Lys Val Phe Glu
        195                 200                 205

Glu Pro Glu Glu Phe Leu Lys His Cys Gln Ala Asp His Leu Leu Asp
    210                 215                 220

Glu Lys Gly Lys Ala Gln Cys Leu Leu Gln Arg Glu Val Val Gln Ser
225                 230                 235                 240

Leu Glu Gln Gln Leu Glu Leu Glu Lys Glu Lys Leu Gly Ala Met Gln
                245                 250                 255

Ala His Leu Ala Gly Lys Met Ala Leu Ala Lys Ala Pro Ser Val Ala
            260                 265                 270
```

```
Ser Met Asp Lys Ser Ser Cys Cys Ile Val Ala Thr Ser Thr Gln Gly
            275                 280                 285

Ser Val Leu Pro Ala Trp Ser Ala Pro Arg Glu Ala Pro Asp Gly Gly
        290                 295                 300

Leu Phe Ala Val Arg Arg His Leu Trp Gly Ser His Gly Asn Ser Ser
305                 310                 315                 320

Phe Pro Glu Phe Phe His Asn Met Asp Tyr Phe Lys Tyr His Asn Met
                325                 330                 335

Arg Pro Pro Phe Thr Tyr Ala Thr Leu Ile Arg Trp Ala Ile Leu Glu
            340                 345                 350

Ala Pro Glu Arg Gln Arg Thr Leu Asn Glu Ile Tyr His Trp Phe Thr
        355                 360                 365

Arg Met Phe Ala Tyr Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Phe Glu Phe Arg Lys Lys
                405                 410                 415

Arg Ser Gln Arg Pro Asn Lys Cys Ser Asn Pro Cys Pro
            420                 425

<210> SEQ ID NO 31
<211> LENGTH: 429
<212> TYPE: PRT
<213> ORGANISM: Mus musculus

<400> SEQUENCE: 31

Met Pro Asn Pro Arg Pro Ala Lys Pro Met Ala Pro Ser Leu Ala Leu
1               5                   10                  15

Gly Pro Ser Pro Gly Val Leu Pro Ser Trp Lys Thr Ala Pro Lys Gly
            20                  25                  30

Ser Glu Leu Leu Gly Thr Arg Gly Ser Gly Gly Pro Phe Gln Gly Arg
        35                  40                  45

Asp Leu Arg Ser Gly Ala His Thr Ser Ser Ser Leu Asn Pro Leu Pro
    50                  55                  60

Pro Ser Gln Leu Gln Leu Pro Thr Val Pro Leu Val Met Val Ala Pro
65                  70                  75                  80

Ser Gly Ala Arg Leu Gly Pro Ser Pro His Leu Gln Ala Leu Leu Gln
                85                  90                  95

Asp Arg Pro His Phe Met His Gln Leu Ser Thr Val Asp Ala His Ala
            100                 105                 110

Gln Thr Pro Val Leu Gln Val Arg Pro Leu Asp Asn Pro Ala Met Ile
        115                 120                 125

Ser Leu Pro Pro Pro Ser Ala Ala Thr Gly Val Phe Ser Leu Lys Ala
    130                 135                 140

Arg Pro Gly Leu Pro Pro Gly Ile Asn Val Ala Ser Leu Glu Trp Val
145                 150                 155                 160

Ser Arg Glu Pro Ala Leu Leu Cys Thr Phe Pro Arg Ser Gly Thr Pro
                165                 170                 175

Arg Lys Asp Ser Asn Leu Leu Ala Ala Pro Gln Gly Ser Tyr Pro Leu
            180                 185                 190

Leu Ala Asn Gly Val Cys Lys Trp Pro Gly Cys Glu Lys Val Phe Glu
        195                 200                 205

Glu Pro Glu Glu Phe Leu Lys His Cys Gln Ala Asp His Leu Leu Asp
    210                 215                 220
```

```
Glu Lys Gly Lys Ala Gln Cys Leu Leu Gln Arg Glu Val Val Gln Ser
225                 230                 235                 240

Leu Glu Gln Gln Leu Glu Leu Lys Glu Lys Leu Gly Ala Met Gln
        245                 250                 255

Ala His Leu Ala Gly Lys Met Ala Leu Ala Lys Ala Pro Ser Val Ala
            260                 265                 270

Ser Met Asp Lys Ser Ser Cys Cys Ile Val Ala Thr Ser Thr Gln Gly
        275                 280                 285

Ser Val Leu Pro Ala Trp Ser Ala Pro Arg Glu Ala Pro Asp Gly Gly
        290                 295                 300

Leu Phe Ala Val Arg Arg His Leu Trp Gly Ser His Gly Asn Ser Ser
305                 310                 315                 320

Phe Pro Glu Phe Phe His Asn Met Asp Tyr Phe Lys Tyr His Asn Met
                325                 330                 335

Arg Pro Pro Phe Thr Tyr Ala Thr Leu Ile Arg Trp Ala Ile Leu Glu
                340                 345                 350

Ala Pro Glu Arg Gln Arg Thr Leu Asn Glu Ile Tyr His Trp Phe Thr
        355                 360                 365

Arg Met Phe Ala Tyr Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Phe Glu Phe Arg Lys Lys
                405                 410                 415

Arg Ser Gln Arg Pro Asn Lys Cys Ser Asn Pro Cys Pro
                420                 425

<210> SEQ ID NO 32
<211> LENGTH: 431
<212> TYPE: PRT
<213> ORGANISM: Macaca fascicularis

<400> SEQUENCE: 32

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Ile Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Pro Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Gly Ala
                165                 170                 175
```

```
Pro Arg Lys Asp Ser Thr Leu Ser Ala Met Pro Gln Ser Ser Tyr Pro
            180                 185                 190

Leu Leu Ala Asn Gly Val Cys Lys Trp Pro Gly Cys Glu Lys Val Phe
            195                 200                 205

Glu Glu Pro Glu Asp Phe Leu Lys His Cys Gln Ala Asp His Leu Leu
            210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
            245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
            275                 280                 285

Gly Ser Ala Val Pro Ala Trp Ser Gly Pro Arg Glu Ala Pro Asp Ser
            290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
            325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
            355                 360                 365

Arg Met Phe Ala Phe Phe Arg Asn His Pro Ala Thr Trp Lys Asn Ala
            370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
            405                 410                 415

Arg Ser Gln Arg Pro Ser Arg Cys Ser Asn Pro Thr Pro Gly Pro
            420                 425                 430

<210> SEQ ID NO 33
<211> LENGTH: 429
<212> TYPE: PRT
<213> ORGANISM: Mus musculus

<400> SEQUENCE: 33

Met Pro Asn Pro Arg Pro Ala Lys Pro Met Ala Pro Ser Leu Ala Leu
1               5                   10                  15

Gly Pro Ser Pro Gly Val Leu Pro Ser Trp Lys Thr Ala Pro Lys Gly
            20                  25                  30

Ser Glu Leu Leu Gly Thr Arg Gly Ser Gly Gly Pro Phe Gln Gly Arg
            35                  40                  45

Asp Leu Arg Ser Gly Ala His Thr Ser Ser Leu Asn Pro Leu Pro
50                  55                  60

Pro Ser Gln Leu Gln Leu Pro Thr Val Pro Leu Val Met Val Ala Pro
65                  70                  75                  80

Ser Gly Ala Arg Leu Gly Pro Ser Pro His Leu Gln Ala Leu Leu Gln
            85                  90                  95

Asp Arg Pro His Phe Met His Gln Leu Ser Thr Val Asp Ala His Ala
            100                 105                 110

Gln Thr Pro Val Leu Gln Val Arg Pro Leu Asp Asn Pro Ala Met Ile
            115                 120                 125
```

```
Ser Leu Pro Pro Pro Ser Ala Ala Thr Gly Val Phe Ser Leu Lys Ala
    130                 135                 140

Arg Pro Gly Leu Pro Gly Ile Asn Val Ala Ser Leu Glu Trp Val
145                 150                 155                 160

Ser Arg Glu Pro Ala Leu Leu Cys Thr Phe Pro Arg Ser Gly Thr Pro
                165                 170                 175

Arg Lys Asp Ser Asn Leu Leu Ala Ala Pro Gln Gly Ser Tyr Pro Leu
            180                 185                 190

Leu Ala Asn Gly Val Cys Lys Trp Pro Gly Cys Glu Lys Val Phe Glu
        195                 200                 205

Glu Pro Glu Glu Phe Leu Lys His Cys Gln Ala Asp His Leu Leu Asp
210                 215                 220

Glu Lys Gly Lys Ala Gln Cys Leu Leu Gln Arg Glu Val Val Gln Ser
225                 230                 235                 240

Leu Glu Gln Gln Leu Glu Leu Glu Lys Glu Lys Leu Gly Ala Met Gln
                245                 250                 255

Ala His Leu Ala Gly Lys Met Ala Leu Ala Lys Ala Pro Ser Val Ala
            260                 265                 270

Ser Met Asp Lys Ser Ser Cys Cys Ile Val Ala Thr Ser Thr Gln Gly
        275                 280                 285

Ser Val Leu Pro Ala Trp Ser Ala Pro Arg Glu Ala Pro Asp Gly Gly
290                 295                 300

Leu Phe Ala Val Arg Arg His Leu Trp Gly Ser His Gly Asn Ser Ser
305                 310                 315                 320

Phe Pro Glu Phe Phe His Asn Met Asp Tyr Phe Lys Tyr His Asn Met
                325                 330                 335

Arg Pro Pro Phe Thr Tyr Ala Thr Leu Ile Arg Trp Ala Ile Leu Glu
            340                 345                 350

Ala Pro Glu Arg Gln Arg Thr Leu Asn Glu Ile Tyr His Trp Phe Thr
        355                 360                 365

Arg Met Phe Ala Tyr Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Phe Glu Phe Arg Lys Lys
                405                 410                 415

Arg Ser Gln Arg Pro Asn Lys Cys Ser Asn Pro Cys Pro
            420                 425

<210> SEQ ID NO 34
<211> LENGTH: 431
<212> TYPE: PRT
<213> ORGANISM: Homo sapiens

<400> SEQUENCE: 34

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Ser Leu Asn Pro Met
    50                  55                  60

Pro Pro Ser Gln Leu Gln Leu Pro Thr Leu Pro Leu Val Met Val Ala
65                  70                  75                  80
```

Pro Ser Gly Ala Arg Leu Gly Pro Leu Pro His Leu Gln Ala Leu Leu
            85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
            115                 120                 125

Ile Ser Leu Thr Pro Pro Thr Thr Ala Thr Gly Val Phe Ser Leu Lys
130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
            165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
            195                 200                 205

Glu Glu Pro Glu Asp Phe Leu Lys His Cys Gln Ala Asp His Leu Leu
            210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
            245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
            275                 280                 285

Gly Pro Val Val Pro Ala Trp Ser Gly Pro Arg Glu Ala Pro Asp Ser
            290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
            325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
            355                 360                 365

Arg Met Phe Ala Phe Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
            405                 410                 415

Arg Ser Gln Arg Pro Ser Arg Cys Ser Asn Pro Thr Pro Gly Pro
            420                 425                 430

<210> SEQ ID NO 35
<211> LENGTH: 429
<212> TYPE: PRT
<213> ORGANISM: Mus musculus

<400> SEQUENCE: 35

Met Pro Asn Pro Arg Pro Ala Lys Pro Met Ala Pro Ser Leu Ala Leu
1               5                   10                  15

Gly Pro Ser Pro Gly Val Leu Pro Ser Trp Lys Thr Ala Pro Lys Gly
            20                  25                  30

Ser Glu Leu Leu Gly Thr Arg Gly Ser Gly Pro Phe Gln Gly Arg
       35                  40                  45

Asp Leu Arg Ser Gly Ala His Thr Ser Ser Leu Asn Pro Leu Pro
 50                  55                  60

Pro Ser Gln Leu Gln Leu Pro Thr Val Pro Leu Val Met Val Ala Pro
 65                  70                  75                  80

Ser Gly Ala Arg Leu Gly Pro Ser Pro His Leu Gln Ala Leu Leu Gln
                 85                  90                  95

Asp Arg Pro His Phe Met His Gln Leu Ser Thr Val Asp Ala His Ala
                100                 105                 110

Gln Thr Pro Val Leu Gln Val Arg Pro Leu Asp Asn Pro Ala Met Ile
            115                 120                 125

Ser Leu Pro Pro Pro Ser Ala Ala Thr Gly Val Phe Ser Leu Lys Ala
            130                 135                 140

Arg Pro Gly Leu Pro Pro Gly Ile Asn Val Ala Ser Leu Glu Trp Val
145                 150                 155                 160

Ser Arg Glu Pro Ala Leu Leu Cys Thr Phe Pro Arg Ser Gly Thr Pro
                165                 170                 175

Arg Lys Asp Ser Asn Leu Leu Ala Ala Pro Gln Gly Ser Tyr Pro Leu
                180                 185                 190

Leu Ala Asn Gly Val Cys Lys Trp Pro Gly Cys Glu Lys Val Phe Glu
            195                 200                 205

Glu Pro Glu Glu Phe Leu Lys His Cys Gln Ala Asp His Leu Leu Asp
210                 215                 220

Glu Lys Gly Lys Ala Gln Cys Leu Leu Gln Arg Glu Val Val Gln Ser
225                 230                 235                 240

Leu Glu Gln Gln Leu Glu Leu Glu Lys Glu Lys Leu Gly Ala Met Gln
                245                 250                 255

Ala His Leu Ala Gly Lys Met Ala Leu Ala Lys Ala Pro Ser Val Ala
                260                 265                 270

Ser Met Asp Lys Ser Ser Cys Cys Ile Val Ala Thr Ser Thr Gln Gly
            275                 280                 285

Ser Val Leu Pro Ala Trp Ser Ala Pro Arg Glu Ala Pro Asp Gly Gly
            290                 295                 300

Leu Phe Ala Val Arg Arg His Leu Trp Gly Ser His Gly Asn Ser Ser
305                 310                 315                 320

Phe Pro Glu Phe Phe His Asn Met Asp Tyr Phe Lys Tyr His Asn Met
                325                 330                 335

Arg Pro Pro Phe Thr Tyr Ala Thr Leu Ile Arg Trp Ala Ile Leu Glu
                340                 345                 350

Ala Pro Glu Arg Gln Arg Thr Leu Asn Glu Ile Tyr His Trp Phe Thr
            355                 360                 365

Arg Met Phe Ala Tyr Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Phe Glu Phe Arg Lys Lys
                405                 410                 415

Arg Ser Gln Arg Pro Asn Lys Cys Ser Asn Pro Cys Pro
            420                 425

<210> SEQ ID NO 36
<211> LENGTH: 429
<212> TYPE: PRT

<213> ORGANISM: Mus musculus

<400> SEQUENCE: 36

Met Pro Asn Pro Arg Pro Ala Lys Pro Met Ala Pro Ser Leu Ala Leu
1               5                   10                  15

Gly Pro Ser Pro Gly Val Leu Pro Ser Trp Lys Thr Ala Pro Lys Gly
            20                  25                  30

Ser Glu Leu Leu Gly Thr Arg Gly Ser Gly Pro Phe Gln Gly Arg
        35                  40                  45

Asp Leu Arg Ser Gly Ala His Thr Ser Ser Leu Asn Pro Leu Pro
    50                  55                  60

Pro Ser Gln Leu Gln Leu Pro Thr Val Pro Leu Val Met Val Ala Pro
65                  70                  75                  80

Ser Gly Ala Arg Leu Gly Pro Ser Pro His Leu Gln Ala Leu Leu Gln
                85                  90                  95

Asp Arg Pro His Phe Met His Gln Leu Ser Thr Val Asp Ala His Ala
            100                 105                 110

Gln Thr Pro Val Leu Gln Val Arg Pro Leu Asp Asn Pro Ala Met Ile
        115                 120                 125

Ser Leu Pro Pro Pro Ser Ala Ala Thr Gly Val Phe Ser Leu Lys Ala
130                 135                 140

Arg Pro Gly Leu Pro Pro Gly Ile Asn Val Ala Ser Leu Glu Trp Val
145                 150                 155                 160

Ser Arg Glu Pro Ala Leu Leu Cys Thr Phe Pro Arg Ser Gly Thr Pro
                165                 170                 175

Arg Lys Asp Ser Asn Leu Leu Ala Ala Pro Gln Gly Ser Tyr Pro Leu
            180                 185                 190

Leu Ala Asn Gly Val Cys Lys Trp Pro Gly Cys Glu Lys Val Phe Glu
        195                 200                 205

Glu Pro Glu Glu Phe Leu Lys His Cys Gln Ala Asp His Leu Leu Asp
210                 215                 220

Glu Lys Gly Lys Ala Gln Cys Leu Leu Gln Arg Glu Val Val Gln Ser
225                 230                 235                 240

Leu Glu Gln Gln Leu Glu Leu Glu Lys Glu Lys Leu Gly Ala Met Gln
                245                 250                 255

Ala His Leu Ala Gly Lys Met Ala Leu Ala Lys Ala Pro Ser Val Ala
            260                 265                 270

Ser Met Asp Lys Ser Ser Cys Cys Ile Val Ala Thr Ser Thr Gln Gly
        275                 280                 285

Ser Val Leu Pro Ala Trp Ser Ala Pro Arg Glu Ala Pro Asp Gly Gly
290                 295                 300

Leu Phe Ala Val Arg Arg His Leu Trp Gly Ser His Gly Asn Ser Ser
305                 310                 315                 320

Phe Pro Glu Phe Phe His Asn Met Asp Tyr Phe Lys Tyr His Asn Met
                325                 330                 335

Arg Pro Pro Phe Thr Tyr Ala Thr Leu Ile Arg Trp Ala Ile Leu Glu
            340                 345                 350

Ala Pro Glu Arg Gln Arg Thr Leu Asn Glu Ile Tyr His Trp Phe Thr
        355                 360                 365

Arg Met Phe Ala Tyr Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Phe Glu Phe Arg Lys Lys

```
                        405                 410                 415
Arg Ser Gln Arg Pro Asn Lys Cys Ser Asn Pro Cys Pro
            420                 425

<210> SEQ ID NO 37
<211> LENGTH: 24
<212> TYPE: DNA
<213> ORGANISM: Artificial sequence
<220> FEATURE:
<223> OTHER INFORMATION: Synthetic primer

<400> SEQUENCE: 37
atctcctgga tgagaaaggc aagg                                              24

<210> SEQ ID NO 38
<211> LENGTH: 24
<212> TYPE: DNA
<213> ORGANISM: Artificial sequence
<220> FEATURE:
<223> OTHER INFORMATION: Synthetic primer

<400> SEQUENCE: 38
tgttgtggaa gaactctggg aagg                                              24

<210> SEQ ID NO 39
<211> LENGTH: 20
<212> TYPE: DNA
<213> ORGANISM: Artificial sequence
<220> FEATURE:
<223> OTHER INFORMATION: Synthetic primer

<400> SEQUENCE: 39
agcctaagat gagcgcaagt                                                   20

<210> SEQ ID NO 40
<211> LENGTH: 20
<212> TYPE: DNA
<213> ORGANISM: Artificial sequence
<220> FEATURE:
<223> OTHER INFORMATION: Synthetic primer

<400> SEQUENCE: 40
ttactaggca gatggccaca                                                   20

<210> SEQ ID NO 41
<211> LENGTH: 23
<212> TYPE: DNA
<213> ORGANISM: Artificial sequence
<220> FEATURE:
<223> OTHER INFORMATION: Synthetic primer

<400> SEQUENCE: 41
aaacctggaa ctcacctacc tgc                                               23

<210> SEQ ID NO 42
<211> LENGTH: 24
<212> TYPE: DNA
<213> ORGANISM: Artificial sequence
<220> FEATURE:
<223> OTHER INFORMATION: Synthetic primer

<400> SEQUENCE: 42
ggtattgttc agcgggtctc catt                                              24

<210> SEQ ID NO 43
<211> LENGTH: 20
```

-continued

```
<212> TYPE: DNA
<213> ORGANISM: Artificial sequence
<220> FEATURE:
<223> OTHER INFORMATION: Synthetic primer

<400> SEQUENCE: 43
accctcccga gattacaacc                                              20

<210> SEQ ID NO 44
<211> LENGTH: 20
<212> TYPE: DNA
<213> ORGANISM: Artificial sequence
<220> FEATURE:
<223> OTHER INFORMATION: Synthetic primer

<400> SEQUENCE: 44
caaggcgtgt tctgtctcaa                                              20

<210> SEQ ID NO 45
<211> LENGTH: 20
<212> TYPE: DNA
<213> ORGANISM: Artificial sequence
<220> FEATURE:
<223> OTHER INFORMATION: Synthetic primer

<400> SEQUENCE: 45
tctgctggat cccaaactct                                              20

<210> SEQ ID NO 46
<211> LENGTH: 20
<212> TYPE: DNA
<213> ORGANISM: Artificial sequence
<220> FEATURE:
<223> OTHER INFORMATION: Synthetic primer

<400> SEQUENCE: 46
tgcactcctg ctgaattttg                                              20

<210> SEQ ID NO 47
<211> LENGTH: 20
<212> TYPE: DNA
<213> ORGANISM: Artificial sequence
<220> FEATURE:
<223> OTHER INFORMATION: Synthetic primer

<400> SEQUENCE: 47
accggcacag acatgaagct                                              20

<210> SEQ ID NO 48
<211> LENGTH: 20
<212> TYPE: DNA
<213> ORGANISM: Artificial sequence
<220> FEATURE:
<223> OTHER INFORMATION: Synthetic primer

<400> SEQUENCE: 48
aggaaggaca ggctggcatt                                              20

<210> SEQ ID NO 49
<211> LENGTH: 26
<212> TYPE: DNA
<213> ORGANISM: Artificial sequence
<220> FEATURE:
<223> OTHER INFORMATION: Synthetic primer

<400> SEQUENCE: 49
tacttcaagt tccacaacat gcgacc                                       26
```

<210> SEQ ID NO 50
<211> LENGTH: 26
<212> TYPE: DNA
<213> ORGANISM: Artificial sequence
<220> FEATURE:
<223> OTHER INFORMATION: Synthetic primer

<400> SEQUENCE: 50
cgcacaaagc acttgtgcag actcag        26

<210> SEQ ID NO 51
<211> LENGTH: 20
<212> TYPE: DNA
<213> ORGANISM: Artificial sequence
<220> FEATURE:
<223> OTHER INFORMATION: Synthetic primer

<400> SEQUENCE: 51
caacgcaccg aatagttacg        20

<210> SEQ ID NO 52
<211> LENGTH: 18
<212> TYPE: DNA
<213> ORGANISM: Artificial sequence
<220> FEATURE:
<223> OTHER INFORMATION: Synthetic primer

<400> SEQUENCE: 52
accagcgtgt ccaggaag        18

<210> SEQ ID NO 53
<211> LENGTH: 33
<212> TYPE: DNA
<213> ORGANISM: Artificial sequence
<220> FEATURE:
<223> OTHER INFORMATION: Synthetic primer

<400> SEQUENCE: 53
cccggatccg ccaccatgcc caaccccagg cct        33

<210> SEQ ID NO 54
<211> LENGTH: 34
<212> TYPE: DNA
<213> ORGANISM: Artificial sequence
<220> FEATURE:
<223> OTHER INFORMATION: Synthetic primer

<400> SEQUENCE: 54
ctctctagag gggccaggtg tagggttgga acac        34

<210> SEQ ID NO 55
<211> LENGTH: 32
<212> TYPE: DNA
<213> ORGANISM: Artificial sequence
<220> FEATURE:
<223> OTHER INFORMATION: Synthetic primer

<400> SEQUENCE: 55
aagaattcgc caccatgccc aaccctaggc ca        32

<210> SEQ ID NO 56
<211> LENGTH: 32
<212> TYPE: DNA
<213> ORGANISM: Artificial sequence
<220> FEATURE:
<223> OTHER INFORMATION: Synthetic primer

```
<400> SEQUENCE: 56
aagaattcgc caccatgccc aaccctaggc ca                                    32

<210> SEQ ID NO 57
<211> LENGTH: 32
<212> TYPE: DNA
<213> ORGANISM: Artificial sequence
<220> FEATURE:
<223> OTHER INFORMATION: Synthetic primer

<400> SEQUENCE: 57
ggggagctct tgtcacatg tatgtgttga ac                                     32

<210> SEQ ID NO 58
<211> LENGTH: 32
<212> TYPE: DNA
<213> ORGANISM: Artificial sequence
<220> FEATURE:
<223> OTHER INFORMATION: Synthetic primer

<400> SEQUENCE: 58
ggggagctcg agggaagata cgaactcagg tc                                    32

<210> SEQ ID NO 59
<211> LENGTH: 30
<212> TYPE: DNA
<213> ORGANISM: Artificial sequence
<220> FEATURE:
<223> OTHER INFORMATION: Synthetic primer

<400> SEQUENCE: 59
ggggagctct gagaactggg taaagtcaga                                       30

<210> SEQ ID NO 60
<211> LENGTH: 32
<212> TYPE: DNA
<213> ORGANISM: Artificial sequence
<220> FEATURE:
<223> OTHER INFORMATION: Synthetic primer

<400> SEQUENCE: 60
gggagatctc aatctcagct ccacaacttc ac                                    32

<210> SEQ ID NO 61
<211> LENGTH: 20
<212> TYPE: DNA
<213> ORGANISM: Artificial sequence
<220> FEATURE:
<223> OTHER INFORMATION: Synthetic primer

<400> SEQUENCE: 61
acaggccact ggtttcagac                                                  20

<210> SEQ ID NO 62
<211> LENGTH: 21
<212> TYPE: DNA
<213> ORGANISM: Artificial sequence
<220> FEATURE:
<223> OTHER INFORMATION: Synthetic primer

<400> SEQUENCE: 62
tgagggaact tcgaagacag a                                                21

<210> SEQ ID NO 63
<211> LENGTH: 22
```

```
<212> TYPE: DNA
<213> ORGANISM: Artificial sequence
<220> FEATURE:
<223> OTHER INFORMATION: Synthetic primer

<400> SEQUENCE: 63
ggagaaggga cacctttgat ct                                              22

<210> SEQ ID NO 64
<211> LENGTH: 22
<212> TYPE: DNA
<213> ORGANISM: Artificial sequence
<220> FEATURE:
<223> OTHER INFORMATION: Synthetic primer

<400> SEQUENCE: 64
gggaatatct gagccctagc aa                                              22

<210> SEQ ID NO 65
<211> LENGTH: 22
<212> TYPE: DNA
<213> ORGANISM: Artificial sequence
<220> FEATURE:
<223> OTHER INFORMATION: Synthetic primer

<400> SEQUENCE: 65
agccctcttg ttctacttct gg                                              22

<210> SEQ ID NO 66
<211> LENGTH: 22
<212> TYPE: DNA
<213> ORGANISM: Artificial sequence
<220> FEATURE:
<223> OTHER INFORMATION: Synthetic primer

<400> SEQUENCE: 66
gacactctag aagcactcag ca                                              22

<210> SEQ ID NO 67
<211> LENGTH: 22
<212> TYPE: DNA
<213> ORGANISM: Artificial sequence
<220> FEATURE:
<223> OTHER INFORMATION: Synthetic primer

<400> SEQUENCE: 67
cgggcaattc atcctggtaa ac                                              22

<210> SEQ ID NO 68
<211> LENGTH: 22
<212> TYPE: DNA
<213> ORGANISM: Artificial sequence
<220> FEATURE:
<223> OTHER INFORMATION: Synthetic primer

<400> SEQUENCE: 68
gatatcactc ctgaagcctg gt                                              22

<210> SEQ ID NO 69
<211> LENGTH: 22
<212> TYPE: DNA
<213> ORGANISM: Artificial sequence
<220> FEATURE:
<223> OTHER INFORMATION: Synthetic primer

<400> SEQUENCE: 69
gagagtcttg gaagtcacca gt                                              22
```

<210> SEQ ID NO 70
<211> LENGTH: 22
<212> TYPE: DNA
<213> ORGANISM: Artificial sequence
<220> FEATURE:
<223> OTHER INFORMATION: Synthetic primer

<400> SEQUENCE: 70
gcagttctca cccacttcct aa                                              22

<210> SEQ ID NO 71
<211> LENGTH: 22
<212> TYPE: DNA
<213> ORGANISM: Artificial sequence
<220> FEATURE:
<223> OTHER INFORMATION: Synthetic primer

<400> SEQUENCE: 71
gggaactcct tgggaaagtt ct                                              22

<210> SEQ ID NO 72
<211> LENGTH: 22
<212> TYPE: DNA
<213> ORGANISM: Artificial sequence
<220> FEATURE:
<223> OTHER INFORMATION: Synthetic primer

<400> SEQUENCE: 72
actggaagag ctctgagaaa gc                                              22

<210> SEQ ID NO 73
<211> LENGTH: 20
<212> TYPE: DNA
<213> ORGANISM: Artificial sequence
<220> FEATURE:
<223> OTHER INFORMATION: Synthetic primer

<400> SEQUENCE: 73
cgtgttaggc aagccctcta                                                 20

<210> SEQ ID NO 74
<211> LENGTH: 20
<212> TYPE: DNA
<213> ORGANISM: Artificial sequence
<220> FEATURE:
<223> OTHER INFORMATION: Synthetic primer

<400> SEQUENCE: 74
ggaatcccaa agcacacagt                                                 20

<210> SEQ ID NO 75
<211> LENGTH: 20
<212> TYPE: DNA
<213> ORGANISM: Artificial sequence
<220> FEATURE:
<223> OTHER INFORMATION: Synthetic primer

<400> SEQUENCE: 75
tgttgccaaa cagcagtctc                                                 20

<210> SEQ ID NO 76
<211> LENGTH: 20
<212> TYPE: DNA
<213> ORGANISM: Artificial sequence
<220> FEATURE:
<223> OTHER INFORMATION: Synthetic primer

```
<400> SEQUENCE: 76
tccatcctga agaaggcaag                                              20

<210> SEQ ID NO 77
<211> LENGTH: 22
<212> TYPE: DNA
<213> ORGANISM: Artificial sequence
<220> FEATURE:
<223> OTHER INFORMATION: Synthetic primer

<400> SEQUENCE: 77
ttgtgctctc tctctgcact gt                                           22

<210> SEQ ID NO 78
<211> LENGTH: 22
<212> TYPE: DNA
<213> ORGANISM: Artificial sequence
<220> FEATURE:
<223> OTHER INFORMATION: Synthetic primer

<400> SEQUENCE: 78
agtccgttcc tgtttgacaa ct                                           22

<210> SEQ ID NO 79
<211> LENGTH: 23
<212> TYPE: DNA
<213> ORGANISM: Artificial sequence
<220> FEATURE:
<223> OTHER INFORMATION: Synthetic primer

<400> SEQUENCE: 79
acatccagga agtccaggga tac                                          23

<210> SEQ ID NO 80
<211> LENGTH: 21
<212> TYPE: DNA
<213> ORGANISM: Artificial sequence
<220> FEATURE:
<223> OTHER INFORMATION: Synthetic primer

<400> SEQUENCE: 80
gcggtggtga cgttgtccaa a                                            21

<210> SEQ ID NO 81
<211> LENGTH: 22
<212> TYPE: DNA
<213> ORGANISM: Artificial sequence
<220> FEATURE:
<223> OTHER INFORMATION: Synthetic primer

<400> SEQUENCE: 81
ccaccatccg ggttcctata aa                                           22

<210> SEQ ID NO 82
<211> LENGTH: 21
<212> TYPE: DNA
<213> ORGANISM: Artificial sequence
<220> FEATURE:
<223> OTHER INFORMATION: Synthetic primer

<400> SEQUENCE: 82
ttgcacactt cgcaccagca t                                            21

<210> SEQ ID NO 83
<211> LENGTH: 21
```

```
<212> TYPE: DNA
<213> ORGANISM: Artificial sequence
<220> FEATURE:
<223> OTHER INFORMATION: Synthetic primer

<400> SEQUENCE: 83
gcacacactc atcgaaaaaa a                                                    21

<210> SEQ ID NO 84
<211> LENGTH: 20
<212> TYPE: DNA
<213> ORGANISM: Artificial sequence
<220> FEATURE:
<223> OTHER INFORMATION: Synthetic primer

<400> SEQUENCE: 84
aatggggccc acatctggta                                                     20

<210> SEQ ID NO 85
<211> LENGTH: 21
<212> TYPE: DNA
<213> ORGANISM: Artificial sequence
<220> FEATURE:
<223> OTHER INFORMATION: Synthetic primer

<400> SEQUENCE: 85
tattgtctac gcagcctgcc c                                                   21

<210> SEQ ID NO 86
<211> LENGTH: 19
<212> TYPE: DNA
<213> ORGANISM: Artificial sequence
<220> FEATURE:
<223> OTHER INFORMATION: Synthetic primer

<400> SEQUENCE: 86
atggtggcat ggggttcaa                                                      19

<210> SEQ ID NO 87
<211> LENGTH: 20
<212> TYPE: DNA
<213> ORGANISM: Artificial sequence
<220> FEATURE:
<223> OTHER INFORMATION: Synthetic primer

<400> SEQUENCE: 87
tgaggatcag gatggcctct                                                     20

<210> SEQ ID NO 88
<211> LENGTH: 19
<212> TYPE: DNA
<213> ORGANISM: Artificial sequence
<220> FEATURE:
<223> OTHER INFORMATION: Synthetic primer

<400> SEQUENCE: 88
gcacatgtgg gctgtggtt                                                      19

<210> SEQ ID NO 89
<211> LENGTH: 19
<212> TYPE: DNA
<213> ORGANISM: Artificial sequence
<220> FEATURE:
<223> OTHER INFORMATION: Synthetic primer

<400> SEQUENCE: 89
aaccacagcc cacatgtgc                                                      19
```

```
<210> SEQ ID NO 90
<211> LENGTH: 21
<212> TYPE: DNA
<213> ORGANISM: Artificial sequence
<220> FEATURE:
<223> OTHER INFORMATION: Synthetic primer

<400> SEQUENCE: 90 tgaccccag agtactgcaa t                                              21

<210> SEQ ID NO 91
<211> LENGTH: 20
<212> TYPE: DNA
<213> ORGANISM: Artificial sequence
<220> FEATURE:
<223> OTHER INFORMATION: Synthetic primer

<400> SEQUENCE: 91
ttttcgaggc tcaggagggt                                               20

<210> SEQ ID NO 92
<211> LENGTH: 21
<212> TYPE: DNA
<213> ORGANISM: Artificial sequence
<220> FEATURE:
<223> OTHER INFORMATION: Synthetic primer

<400> SEQUENCE: 92
tgtccactga cctgtccttc c                                             21

<210> SEQ ID NO 93
<211> LENGTH: 21
<212> TYPE: DNA
<213> ORGANISM: Artificial sequence
<220> FEATURE:
<223> OTHER INFORMATION: Synthetic primer

<400> SEQUENCE: 93
caggaaggac aggtcagtgg a                                             21

<210> SEQ ID NO 94
<211> LENGTH: 20
<212> TYPE: DNA
<213> ORGANISM: Artificial sequence
<220> FEATURE:
<223> OTHER INFORMATION: Synthetic primer

<400> SEQUENCE: 94
tgggccactc acttgaggaa                                               20

<210> SEQ ID NO 95
<211> LENGTH: 18
<212> TYPE: DNA
<213> ORGANISM: Artificial sequence
<220> FEATURE:
<223> OTHER INFORMATION: Synthetic primer

<400> SEQUENCE: 95
tgtcgtggtc acctgcat                                                 18

<210> SEQ ID NO 96
<211> LENGTH: 21
<212> TYPE: DNA
<213> ORGANISM: Artificial sequence
<220> FEATURE:
<223> OTHER INFORMATION: Synthetic primer
```

<400> SEQUENCE: 96
cattacctgc tgctccagag a                                              21

<210> SEQ ID NO 97
<211> LENGTH: 19
<212> TYPE: DNA
<213> ORGANISM: Artificial sequence
<220> FEATURE:
<223> OTHER INFORMATION: Synthetic primer

<400> SEQUENCE: 97
tagcctgggc aaagatgtg                                                 19

<210> SEQ ID NO 98
<211> LENGTH: 21
<212> TYPE: DNA
<213> ORGANISM: Artificial sequence
<220> FEATURE:
<223> OTHER INFORMATION: Synthetic primer

<400> SEQUENCE: 98
agtctgagtc tgccaccacc a                                              21

<210> SEQ ID NO 99
<211> LENGTH: 20
<212> TYPE: DNA
<213> ORGANISM: Artificial sequence
<220> FEATURE:
<223> OTHER INFORMATION: Synthetic primer

<400> SEQUENCE: 99
tttaagcctc tgggtcacca                                                20

<210> SEQ ID NO 100
<211> LENGTH: 20
<212> TYPE: DNA
<213> ORGANISM: Artificial sequence
<220> FEATURE:
<223> OTHER INFORMATION: Synthetic primer

<400> SEQUENCE: 100
tgggaatgtg ctgtttccat                                                20

<210> SEQ ID NO 101
<211> LENGTH: 19
<212> TYPE: DNA
<213> ORGANISM: Artificial sequence
<220> FEATURE:
<223> OTHER INFORMATION: Synthetic primer

<400> SEQUENCE: 101 tgcatgggc ttgattcat                                                  19

<210> SEQ ID NO 102
<211> LENGTH: 19
<212> TYPE: DNA
<213> ORGANISM: Artificial sequence
<220> FEATURE:
<223> OTHER INFORMATION: Synthetic primer

<400> SEQUENCE: 102
aacccactct gagggcact                                                 19

<210> SEQ ID NO 103
<211> LENGTH: 20

```
<212> TYPE: DNA
<213> ORGANISM: Artificial sequence
<220> FEATURE:
<223> OTHER INFORMATION: Synthetic primer

<400> SEQUENCE: 103
tttggggaat gtgcccctta                                         20

<210> SEQ ID NO 104
<211> LENGTH: 20
<212> TYPE: DNA
<213> ORGANISM: Artificial sequence
<220> FEATURE:
<223> OTHER INFORMATION: Synthetic primer

<400> SEQUENCE: 104
aatgtgccta tgagcccaga                                         20

<210> SEQ ID NO 105
<211> LENGTH: 20
<212> TYPE: DNA
<213> ORGANISM: Artificial sequence
<220> FEATURE:
<223> OTHER INFORMATION: Synthetic primer

<400> SEQUENCE: 105
ataggcacat tggggaggaa                                         20

<210> SEQ ID NO 106
<211> LENGTH: 20
<212> TYPE: DNA
<213> ORGANISM: Artificial sequence
<220> FEATURE:
<223> OTHER INFORMATION: Synthetic primer

<400> SEQUENCE: 106
tgttcgtcca tcctcctttc                                         20

<210> SEQ ID NO 107
<211> LENGTH: 26
<212> TYPE: DNA
<213> ORGANISM: Artificial sequence
<220> FEATURE:
<223> OTHER INFORMATION: Synthetic primer

<400> SEQUENCE: 107
agttcaattt gaatttcaga taaacg                                  26

<210> SEQ ID NO 108
<211> LENGTH: 26
<212> TYPE: DNA
<213> ORGANISM: Artificial sequence
<220> FEATURE:
<223> OTHER INFORMATION: Synthetic primer

<400> SEQUENCE: 108
agttcagcgc gagcgccaga gcgccg                                  26

<210> SEQ ID NO 109
<211> LENGTH: 19
<212> TYPE: DNA
<213> ORGANISM: Artificial sequence
<220> FEATURE:
<223> OTHER INFORMATION: Synthetic primer

<400> SEQUENCE: 109
gcagcggaca ctcaatgag                                          19
```

-continued

<210> SEQ ID NO 110
<211> LENGTH: 21
<212> TYPE: DNA
<213> ORGANISM: Artificial sequence
<220> FEATURE:
<223> OTHER INFORMATION: Synthetic primer

<400> SEQUENCE: 110
tcagaaggca acttccatgg t                                              21

<210> SEQ ID NO 111
<211> LENGTH: 21
<212> TYPE: DNA
<213> ORGANISM: Artificial sequence
<220> FEATURE:
<223> OTHER INFORMATION: Synthetic primer

<400> SEQUENCE: 111
agatggagtt acaggcgtga a                                              21

<210> SEQ ID NO 112
<211> LENGTH: 21
<212> TYPE: DNA
<213> ORGANISM: Artificial sequence
<220> FEATURE:
<223> OTHER INFORMATION: Synthetic primer

<400> SEQUENCE: 112
tgaaacctgg ctgagaaatt g                                              21

<210> SEQ ID NO 113
<211> LENGTH: 19
<212> TYPE: DNA
<213> ORGANISM: Artificial sequence
<220> FEATURE:
<223> OTHER INFORMATION: Synthetic primer

<400> SEQUENCE: 113
tgcgggaggc gtctgttta                                                 19

<210> SEQ ID NO 114
<211> LENGTH: 21
<212> TYPE: DNA
<213> ORGANISM: Artificial sequence
<220> FEATURE:
<223> OTHER INFORMATION: Synthetic primer

<400> SEQUENCE: 114
tcatcacctc tgaaaccttg g                                              21

<210> SEQ ID NO 115
<211> LENGTH: 21
<212> TYPE: DNA
<213> ORGANISM: Artificial sequence
<220> FEATURE:
<223> OTHER INFORMATION: Synthetic primer

<400> SEQUENCE: 115
cgggaggtaa gaagaagtgg a                                              21

<210> SEQ ID NO 116
<211> LENGTH: 20
<212> TYPE: DNA
<213> ORGANISM: Artificial sequence
<220> FEATURE:
<223> OTHER INFORMATION: Synthetic primer

```
<400> SEQUENCE: 116
ggtgactcac ttgggaatcg                                              20

<210> SEQ ID NO 117
<211> LENGTH: 21
<212> TYPE: DNA
<213> ORGANISM: Artificial sequence
<220> FEATURE:
<223> OTHER INFORMATION: Synthetic primer

<400> SEQUENCE: 117
tattcccata gccaagctcc a                                            21

<210> SEQ ID NO 118
<211> LENGTH: 21
<212> TYPE: DNA
<213> ORGANISM: Artificial sequence
<220> FEATURE:
<223> OTHER INFORMATION: Synthetic primer

<400> SEQUENCE: 118
tgtgtcactc agagtggctg t                                            21

<210> SEQ ID NO 119
<211> LENGTH: 19
<212> TYPE: DNA
<213> ORGANISM: Artificial sequence
<220> FEATURE:
<223> OTHER INFORMATION: Synthetic primer

<400> SEQUENCE: 119
aattccaagc cctcatgca                                               19

<210> SEQ ID NO 120
<211> LENGTH: 20
<212> TYPE: DNA
<213> ORGANISM: Artificial sequence
<220> FEATURE:
<223> OTHER INFORMATION: Synthetic primer

<400> SEQUENCE: 120
ttccaaaagc ctgacagcaa                                              20

<210> SEQ ID NO 121
<211> LENGTH: 20
<212> TYPE: DNA
<213> ORGANISM: Artificial sequence
<220> FEATURE:
<223> OTHER INFORMATION: Synthetic primer

<400> SEQUENCE: 121
tcacccttgg ttgttttcac                                              20

<210> SEQ ID NO 122
<211> LENGTH: 20
<212> TYPE: DNA
<213> ORGANISM: Artificial sequence
<220> FEATURE:
<223> OTHER INFORMATION: Synthetic primer

<400> SEQUENCE: 122
tccgccatct ttagcaactt                                              20

<210> SEQ ID NO 123
<211> LENGTH: 21
```

```
<212> TYPE: DNA
<213> ORGANISM: Artificial sequence
<220> FEATURE:
<223> OTHER INFORMATION: Synthetic primer

<400> SEQUENCE: 123
aaatgagtgc tctccacagg g                                              21

<210> SEQ ID NO 124
<211> LENGTH: 21
<212> TYPE: DNA
<213> ORGANISM: Artificial sequence
<220> FEATURE:
<223> OTHER INFORMATION: Synthetic primer

<400> SEQUENCE: 124
caaaataaaa aatcccgagg g                                              21

<210> SEQ ID NO 125
<211> LENGTH: 20
<212> TYPE: DNA
<213> ORGANISM: Artificial sequence
<220> FEATURE:
<223> OTHER INFORMATION: Synthetic primer

<400> SEQUENCE: 125
aacccgcaaa cgtgtattca                                                20

<210> SEQ ID NO 126
<211> LENGTH: 20
<212> TYPE: DNA
<213> ORGANISM: Artificial sequence
<220> FEATURE:
<223> OTHER INFORMATION: Synthetic primer

<400> SEQUENCE: 126
cgtagttaat tcatgcggct                                                20

<210> SEQ ID NO 127
<211> LENGTH: 18
<212> TYPE: DNA
<213> ORGANISM: Artificial sequence
<220> FEATURE:
<223> OTHER INFORMATION: Synthetic primer

<400> SEQUENCE: 127
tttcttttcc cccacgcc                                                  18

<210> SEQ ID NO 128
<211> LENGTH: 21
<212> TYPE: DNA
<213> ORGANISM: Artificial sequence
<220> FEATURE:
<223> OTHER INFORMATION: Synthetic primer

<400> SEQUENCE: 128
atgctgagat gagtcgaatg c                                              21

<210> SEQ ID NO 129
<211> LENGTH: 21
<212> TYPE: DNA
<213> ORGANISM: Artificial sequence
<220> FEATURE:
<223> OTHER INFORMATION: Synthetic primer

<400> SEQUENCE: 129
ttgacaagtc actttacccc g                                              21
```

<210> SEQ ID NO 130
<211> LENGTH: 21
<212> TYPE: DNA
<213> ORGANISM: Artificial sequence
<220> FEATURE:
<223> OTHER INFORMATION: Synthetic primer

<400> SEQUENCE: 130
caccaagacc cctttaactc a                                              21

<210> SEQ ID NO 131
<211> LENGTH: 20
<212> TYPE: DNA
<213> ORGANISM: Artificial sequence
<220> FEATURE:
<223> OTHER INFORMATION: Synthetic primer

<400> SEQUENCE: 131
aagttctcct cctcgtcgca                                                20

<210> SEQ ID NO 132
<211> LENGTH: 27
<212> TYPE: DNA
<213> ORGANISM: Artificial sequence
<220> FEATURE:
<223> OTHER INFORMATION: Synthetic primer

<400> SEQUENCE: 132
cgtttatagc agttacacag aatttca                                        27

<210> SEQ ID NO 133
<211> LENGTH: 23
<212> TYPE: DNA
<213> ORGANISM: Artificial sequence
<220> FEATURE:
<223> OTHER INFORMATION: Synthetic primer

<400> SEQUENCE: 133
ggctcaatga tatatttgcc agt                                            23

<210> SEQ ID NO 134
<211> LENGTH: 21
<212> TYPE: DNA
<213> ORGANISM: Artificial sequence
<220> FEATURE:
<223> OTHER INFORMATION: Synthetic primer

<400> SEQUENCE: 134
cctgggcaac agaatgagac t                                              21

<210> SEQ ID NO 135
<211> LENGTH: 21
<212> TYPE: DNA
<213> ORGANISM: Artificial sequence
<220> FEATURE:
<223> OTHER INFORMATION: Synthetic primer

<400> SEQUENCE: 135
ttcacctcct aactgctgct t                                              21

<210> SEQ ID NO 136
<211> LENGTH: 21
<212> TYPE: DNA
<213> ORGANISM: Artificial sequence
<220> FEATURE:
<223> OTHER INFORMATION: Synthetic primer

```
<400> SEQUENCE: 136
agcctgggtg acaaagtgaa a                                              21

<210> SEQ ID NO 137
<211> LENGTH: 20
<212> TYPE: DNA
<213> ORGANISM: Artificial sequence
<220> FEATURE:
<223> OTHER INFORMATION: Synthetic primer

<400> SEQUENCE: 137
gcacagccag attgaaacaa                                                20

<210> SEQ ID NO 138
<211> LENGTH: 26
<212> TYPE: DNA
<213> ORGANISM: Artificial sequence
<220> FEATURE:
<223> OTHER INFORMATION: Synthetic primer

<400> SEQUENCE: 138
tacttcaagt tccacaacat gcgacc                                         26

<210> SEQ ID NO 139
<211> LENGTH: 26
<212> TYPE: DNA
<213> ORGANISM: Artificial sequence
<220> FEATURE:
<223> OTHER INFORMATION: Synthetic primer

<400> SEQUENCE: 139
cgcacaaagc acttgtgcag actcag                                         26

<210> SEQ ID NO 140
<211> LENGTH: 20
<212> TYPE: DNA
<213> ORGANISM: Artificial sequence
<220> FEATURE:
<223> OTHER INFORMATION: Synthetic primer

<400> SEQUENCE: 140
attctctgct ctcctcgacg                                                20

<210> SEQ ID NO 141
<211> LENGTH: 21
<212> TYPE: DNA
<213> ORGANISM: Artificial sequence
<220> FEATURE:
<223> OTHER INFORMATION: Synthetic primer

<400> SEQUENCE: 141
tgcctctttt ccacagaaac a                                              21

<210> SEQ ID NO 142
<211> LENGTH: 24
<212> TYPE: DNA
<213> ORGANISM: Artificial sequence
<220> FEATURE:
<223> OTHER INFORMATION: Synthetic primer

<400> SEQUENCE: 142
ccccttcatt gacctcaact acat                                           24

<210> SEQ ID NO 143
<211> LENGTH: 19
```

```
<212> TYPE: DNA
<213> ORGANISM: Artificial sequence
<220> FEATURE:
<223> OTHER INFORMATION: Synthetic primer

<400> SEQUENCE: 143
cgctcctgga agatggtga                                              19

<210> SEQ ID NO 144
<211> LENGTH: 21
<212> TYPE: DNA
<213> ORGANISM: Artificial sequence
<220> FEATURE:
<223> OTHER INFORMATION: Synthetic primer

<400> SEQUENCE: 144
aagccaggct gatcctttc t                                            21

<210> SEQ ID NO 145
<211> LENGTH: 19
<212> TYPE: DNA
<213> ORGANISM: Artificial sequence
<220> FEATURE:
<223> OTHER INFORMATION: Synthetic primer

<400> SEQUENCE: 145
tctgcctccc accagtttg                                              19

<210> SEQ ID NO 146
<211> LENGTH: 31
<212> TYPE: DNA
<213> ORGANISM: Artificial sequence
<220> FEATURE:
<223> OTHER INFORMATION: Synthetic primer

<400> SEQUENCE: 146
ttcatgcggc tctcttactc atcctagagc t                                31

<210> SEQ ID NO 147
<211> LENGTH: 30
<212> TYPE: DNA
<213> ORGANISM: Artificial sequence
<220> FEATURE:
<223> OTHER INFORMATION: Synthetic primer

<400> SEQUENCE: 147
gagtaagaga gccgcatgaa ttaactacgc                                  30

<210> SEQ ID NO 148
<211> LENGTH: 32
<212> TYPE: DNA
<213> ORGANISM: Artificial sequence
<220> FEATURE:
<223> OTHER INFORMATION: Synthetic primer

<400> SEQUENCE: 148
ttcatgcggc tctcttactc aaaagggatc ct                               32

<210> SEQ ID NO 149
<211> LENGTH: 30
<212> TYPE: DNA
<213> ORGANISM: Artificial sequence
<220> FEATURE:
<223> OTHER INFORMATION: Synthetic primer

<400> SEQUENCE: 149
gagtaagaga gccgcatgaa ttaactacgc                                  30
```

<210> SEQ ID NO 150
<211> LENGTH: 21
<212> TYPE: DNA
<213> ORGANISM: Artificial sequence
<220> FEATURE:
<223> OTHER INFORMATION: Synthetic primer

<400> SEQUENCE: 150
aaaaggagaa gctgggagct a                                              21

<210> SEQ ID NO 151
<211> LENGTH: 21
<212> TYPE: DNA
<213> ORGANISM: Artificial sequence
<220> FEATURE:
<223> OTHER INFORMATION: Synthetic primer

<400> SEQUENCE: 151
tgagtactgg tggctacgat g                                              21

<210> SEQ ID NO 152
<211> LENGTH: 21
<212> TYPE: DNA
<213> ORGANISM: Artificial sequence
<220> FEATURE:
<223> OTHER INFORMATION: Synthetic primer

<400> SEQUENCE: 152
ctagtgctgc atgaggagac a                                              21

<210> SEQ ID NO 153
<211> LENGTH: 18
<212> TYPE: DNA
<213> ORGANISM: Artificial sequence
<220> FEATURE:
<223> OTHER INFORMATION: Synthetic primer

<400> SEQUENCE: 153
tgtgcggagg tttgctgt                                                  18

<210> SEQ ID NO 154
<211> LENGTH: 20
<212> TYPE: DNA
<213> ORGANISM: Artificial sequence
<220> FEATURE:
<223> OTHER INFORMATION: Synthetic primer

<400> SEQUENCE: 154
caggccagac tttgttggat                                                20

<210> SEQ ID NO 155
<211> LENGTH: 20
<212> TYPE: DNA
<213> ORGANISM: Artificial sequence
<220> FEATURE:
<223> OTHER INFORMATION: Synthetic primer

<400> SEQUENCE: 155
gcgctcatct taggctttgt                                                20

<210> SEQ ID NO 156
<211> LENGTH: 20
<212> TYPE: DNA
<213> ORGANISM: Artificial sequence
<220> FEATURE:
<223> OTHER INFORMATION: Synthetic primer

<400> SEQUENCE: 156
accctcccga gattacaacc                                              20

<210> SEQ ID NO 157
<211> LENGTH: 20
<212> TYPE: DNA
<213> ORGANISM: Artificial sequence
<220> FEATURE:
<223> OTHER INFORMATION: Synthetic primer

<400> SEQUENCE: 157
caaggcgtgt tctgtctcaa                                              20

<210> SEQ ID NO 158
<211> LENGTH: 21
<212> TYPE: DNA
<213> ORGANISM: Artificial sequence
<220> FEATURE:
<223> OTHER INFORMATION: Synthetic primer

<400> SEQUENCE: 158
aacttctagg gaccaggggc t                                            21

<210> SEQ ID NO 159
<211> LENGTH: 20
<212> TYPE: DNA
<213> ORGANISM: Artificial sequence
<220> FEATURE:
<223> OTHER INFORMATION: Synthetic primer

<400> SEQUENCE: 159
caagtacccc accctgctta                                              20

<210> SEQ ID NO 160
<211> LENGTH: 21
<212> TYPE: DNA
<213> ORGANISM: Artificial sequence
<220> FEATURE:
<223> OTHER INFORMATION: Synthetic primer

<400> SEQUENCE: 160
tgctccataa acgattatgg c                                            21

<210> SEQ ID NO 161
<211> LENGTH: 20
<212> TYPE: DNA
<213> ORGANISM: Artificial sequence
<220> FEATURE:
<223> OTHER INFORMATION: Synthetic primer

<400> SEQUENCE: 161
atgaagaccc tgggaatcaa                                              20

<210> SEQ ID NO 162
<211> LENGTH: 21
<212> TYPE: DNA
<213> ORGANISM: Artificial sequence
<220> FEATURE:
<223> OTHER INFORMATION: Synthetic primer

<400> SEQUENCE: 162
aagccccagt agaatcagca a                                            21

<210> SEQ ID NO 163
<211> LENGTH: 20

```
<212> TYPE: DNA
<213> ORGANISM: Artificial sequence
<220> FEATURE:
<223> OTHER INFORMATION: Synthetic primer

<400> SEQUENCE: 163
tgtcgtgaat gtggggtgat                                           20

<210> SEQ ID NO 164
<211> LENGTH: 20
<212> TYPE: DNA
<213> ORGANISM: Artificial sequence
<220> FEATURE:
<223> OTHER INFORMATION: Synthetic primer

<400> SEQUENCE: 164
accagccagc tatcaactcg                                           20

<210> SEQ ID NO 165
<211> LENGTH: 19
<212> TYPE: DNA
<213> ORGANISM: Artificial sequence'
<220> FEATURE:
<223> OTHER INFORMATION: Synthetic primer

<400> SEQUENCE: 165
ttacattggt ccagccacc                                            19

<210> SEQ ID NO 166
<211> LENGTH: 24
<212> TYPE: DNA
<213> ORGANISM: Artificial sequence
<220> FEATURE:
<223> OTHER INFORMATION: Synthetic primer

<400> SEQUENCE: 166
ctaggccaca gaattgaaag atct                                      24

<210> SEQ ID NO 167
<211> LENGTH: 25
<212> TYPE: DNA
<213> ORGANISM: Artificial sequence
<220> FEATURE:
<223> OTHER INFORMATION: Synthetic primer

<400> SEQUENCE: 167
gtaggtggaa attctagcat catcc                                     25

<210> SEQ ID NO 168
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 168
aagccatggc aatagttcct t                                         21

<210> SEQ ID NO 169
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 169
gcagcggaca ctcaatgag                                            19
```

```
<210> SEQ ID NO 170
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 170
agaaggtagg acattcctt                                                19

<210> SEQ ID NO 171
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 171
aataccgaga gttgcgtctg c                                             21

<210> SEQ ID NO 172
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 172
cttctgttgt agaaacaac                                                19

<210> SEQ ID NO 173
<211> LENGTH: 27
<212> TYPE: DNA
<213> ORGANISM: Artificial sequence
<220> FEATURE:
<223> OTHER INFORMATION: Synthetic probe

<400> SEQUENCE: 173
agatggacgt cacctaccac atcacgg                                       27

<210> SEQ ID NO 174
<211> LENGTH: 27
<212> TYPE: DNA
<213> ORGANISM: Artificial sequence
<220> FEATURE:
<223> OTHER INFORMATION: Synthetic probe

<400> SEQUENCE: 174
agatggacgt ctgcgcccac atcacgg                                       27

<210> SEQ ID NO 175
<211> LENGTH: 27
<212> TYPE: DNA
<213> ORGANISM: Artificial sequence
<220> FEATURE:
<223> OTHER INFORMATION: Synthetic probe

<400> SEQUENCE: 175
agatggacgt cgacgcccac atcacgg                                       27

<210> SEQ ID NO 176
<211> LENGTH: 25
<212> TYPE: DNA
<213> ORGANISM: Artificial sequence
<220> FEATURE:
<223> OTHER INFORMATION: Synthetic primer
```

-continued

```
<400> SEQUENCE: 176
agtaaagggt agttggaagg taaag                                          25

<210> SEQ ID NO 177
<211> LENGTH: 25
<212> TYPE: DNA
<213> ORGANISM: Artificial sequence
<220> FEATURE:
<223> OTHER INFORMATION: Synthetic primer

<400> SEQUENCE: 177
aaaaacaaaa aatcccatcc taaat                                          25

<210> SEQ ID NO 178
<211> LENGTH: 25
<212> TYPE: DNA
<213> ORGANISM: Artificial sequence
<220> FEATURE:
<223> OTHER INFORMATION: Synthetic primer

<400> SEQUENCE: 178
ttgggttaag tttgttgtag gatag                                          25

<210> SEQ ID NO 179
<211> LENGTH: 25
<212> TYPE: DNA
<213> ORGANISM: Artificial sequence
<220> FEATURE:
<223> OTHER INFORMATION: Synthetic primer

<400> SEQUENCE: 179
atctaaaccc tattatcaca acccc                                          25

<210> SEQ ID NO 180
<211> LENGTH: 7
<212> TYPE: DNA
<213> ORGANISM: Artificial sequence
<220> FEATURE:
<223> OTHER INFORMATION: Synthetic polynucleotide

<400> SEQUENCE: 180 tgtttac                                                               7

<210> SEQ ID NO 181
<211> LENGTH: 7
<212> TYPE: DNA
<213> ORGANISM: Artificial sequence
<220> FEATURE:
<223> OTHER INFORMATION: Synthetic polynucleotide

<400> SEQUENCE: 181 aaaaggg                                                               7
```